(12) United States Patent
Breaux et al.

(10) Patent No.: US 8,445,689 B2
(45) Date of Patent: *May 21, 2013

(54) PESTICIDES

(75) Inventors: Nneka T. Breaux, Indianapolis, IN (US); Michael R. Loso, Carmel, IN (US); Timothy C. Johnson, Indianapolis, IN (US); Jonathan M. Babcock, Carmel, IN (US); Benjamin M. Nugent, Brownsburg, IN (US); Timothy P. Martin, Noblesville, IN (US); Annette Vitale Brown, Lafayette, IN (US); Ronald Ross, Jr., Zionsville, IN (US); William C. Lo, Fishers, IN (US); Matthias S. Ober, Midland, MI (US)

(73) Assignee: Dow AgroSciences, LLC., Indianapolis, IN (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/444,286

(22) Filed: Apr. 11, 2012

(65) Prior Publication Data

US 2012/0225782 A1  Sep. 6, 2012

Related U.S. Application Data

(60) Division of application No. 12/962,114, filed on Dec. 7, 2010, now Pat. No. 8,178,685, which is a continuation of application No. 12/394,905, filed on Feb. 27, 2009, now abandoned.

(60) Provisional application No. 61/067,874, filed on Mar. 3, 2008.

(51) Int. Cl.
*C07D 213/56* (2006.01)
*A61K 31/44* (2006.01)

(52) U.S. Cl.
USPC .......................................... 546/338; 514/357

(58) Field of Classification Search
None
See application file for complete search history.

(56) References Cited

U.S. PATENT DOCUMENTS

| | | | |
|---|---|---|---|
| 3,711,486 A | 1/1973 | Torba et al. | |
| 3,787,420 A | 1/1974 | Torba et al. | |
| 3,852,279 A | 12/1974 | Krapcho et al. | |
| 4,556,413 A | 12/1985 | Frater et al. | |
| 4,577,028 A | 3/1986 | Martin et al. | |
| 4,692,184 A | 9/1987 | Lee | |
| 4,747,871 A | 5/1988 | Ruminski et al. | |
| 4,833,158 A | 5/1989 | Twydell et al. | |
| 4,948,896 A | 8/1990 | Nagao | |
| 4,973,695 A | 11/1990 | Yamashita et al. | |
| 5,053,516 A | 10/1991 | Hartmann et al. | |
| 5,099,023 A | 3/1992 | Miller et al. | |
| 5,099,024 A | 3/1992 | Pulwer et al. | |
| 5,118,809 A | 6/1992 | Cevasco et al. | |
| 5,124,458 A | 6/1992 | Cevasco et al. | |
| 5,169,432 A | 12/1992 | Auinbauh et al. | |
| 5,225,560 A | 7/1993 | Cevasco et al. | |
| 5,227,491 A | 7/1993 | Doehner, Jr. | |
| 5,229,519 A | 7/1993 | Zhang et al. | |
| 6,060,502 A | 5/2000 | Louder et al. | |
| 7,511,149 B2 | 3/2009 | Arndt et al. | |
| 7,541,469 B2 | 6/2009 | Renga et al. | |
| 7,604,815 B2 | 10/2009 | Loso et al. | |
| 7,678,920 B2 | 3/2010 | Zhu et al. | |
| 2002/0032328 A1 | 3/2002 | Shermolovich et al. | |
| 2003/0078430 A1 | 4/2003 | Satake et al. | |
| 2004/0158067 A1 | 8/2004 | Hutchison et al. | |
| 2006/0199964 A1 | 9/2006 | Jackson et al. | |
| 2007/0203191 A1 | 8/2007 | Loso et al. | |
| 2007/0249837 A1 | 10/2007 | Gebhardt et al. | |
| 2007/0299264 A1 | 12/2007 | Huang et al. | |
| 2008/0108665 A1 | 5/2008 | Huang et al. | |
| 2008/0108666 A1 | 5/2008 | Loso et al. | |
| 2008/0108667 A1 | 5/2008 | Zhu et al. | |
| 2008/0132705 A1 | 6/2008 | Heller et al. | |
| 2008/0194830 A1 | 8/2008 | Meyer et al. | |
| 2008/0280915 A1 | 11/2008 | Loso et al. | |
| 2009/0029863 A1* | 1/2009 | Nugent et al. ................ 504/358 |

FOREIGN PATENT DOCUMENTS

| | | |
|---|---|---|
| DE | 19523658 A1 | 6/1995 |
| WO | WO98/02492 | 1/1998 |
| WO | WO01/07430 | 2/2001 |
| WO | WO/2006/000333 | 1/2006 |
| WO | WO/2006/037945 | 4/2006 |
| WO | WO2007/075459 A2 | 7/2007 |
| WO | WO2007/149134 | 8/2007 |

(Continued)

OTHER PUBLICATIONS

Silverman, R. "The Organic Chemistry of Drug Design and Drug Action," 2004, Elsevier, pp. 29-32.*

Kagabu, Shinzo and Medej, Somporn; "Stability Comparison of Imidacloprid and Related Compounds under Simulated Sunlight, Hydrolysis Conditions, and to Oxygen;" Biosci. Biotech. Biochem., 59 (6), 980-985, (1995).

Kagabu, Shinzo; Murata, Natsue; Hibino, Rika; Hanzawa, Madoka and Nishimura, Keiichiro; "Insecticidal and Neuroblocking Activities of Thiamethoxam-Type Compounds in the American Cockroach (Periplaneta americana L.);" J. Pesticide Sci. 30(2), 111-115 (2005).

(Continued)

*Primary Examiner* — Janet Andres
*Assistant Examiner* — Heidi Reese
(74) *Attorney, Agent, or Firm* — Carl D. Corvin

(57) ABSTRACT

Compounds having the following generic formula are disclosed.

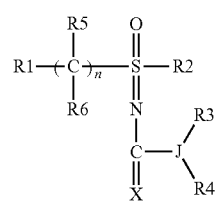

7 Claims, No Drawings

FOREIGN PATENT DOCUMENTS

| | | |
|---|---|---|
| WO | WO2007/003781 | 9/2007 |
| WO | WO2007/003787 | 2/2008 |
| WO | WO2008/018917 | 2/2008 |
| WO | WO/2008/027539 | 3/2008 |
| WO | WO/2008/057129 | 5/2008 |
| WO | WO2008/057129 | 5/2008 |
| WO | WO/2008/057131 | 5/2008 |
| WO | WO2008/018917 | 12/2008 |
| WO | WO/2008/155140 | 12/2008 |
| WO | WO2007003779 | 1/2009 |
| WO | PCT/US2009/035475 | 2/2009 |

OTHER PUBLICATIONS

Sparks, Thomas C.; Crouse, Gary D. and Durst, Gregory; "Natural products as insecticides: the biology, biochemistry and quantitative structure-activity relationships of spinosyns and spinosoids;" Pest Management Science, 57:896-905 (2001).

Wakita, Takeo; Kinoshita, Katsutoshi; Kodaka, Kenji; Yasui, Naoko; Naoi, Atsuko and Banba, Sinichi; "Synthesis and Structure-Activity Relationships of Dinotefuran Derivatives: Modification in the Tetrahydro-3-furylmethyl Part;" J. Pesticide Sci. 29 (4), 356-363 (2004).

Kollmeyer, Willy D.; Flattum, Roger F.; Foster, James P.; Powell, James E.; Schroeder, Mark E. and Soloway, S. Barney; "Discovery of the Nitromethylene Heterocycle Insecticides;" Nicotinoid Insecticides and the Nicotinic Acetylcholine Receptor [Eds.: Yamamoto, I. and Casida, J.E.]; 1999, pp. 71-89, Springer-Verlag, Tokyo.

Shiga, Yasushi; Okada, Itaru and Fukuchi, Toshiki; "Synthesis and Acaricidal Activity of N-(1,3,4-Thiadiazol-2-yl)cyclopropanecarboxamides;" J. Pesticide Sci. 28, 61-63 (2003).

Singer, Alvin; McElvain, S.M. 2,6-Dimethylpyridine. Organic Syntheses, 1934, 14, 30.

Haibo Yu, Zhenfang Qin, Hong Dai, Xin Zhang, Xue Qin, Tingting Wang and Jianxin Fang, Synthesis and Insecticidal Activity of N-Substituted (1,3-Thiazole)alkyl Sulfoximine Derivatives, J. Agric. Food Chem. 2008, 56, 11356-11360.

Haibo Yu, Zhenfang Qin, Hong Dai, Xin Zhang, Xue Qin, Tingting Wang, and Jianxin Fang, Synthesis and insecticidal activity of N-cyano 2-(substituted amino) ethyl methyl sulfoximine derivatives, General Papers, ARKIVCC 2008 (xvi) 99-109.

Kawanshi, Hiroyuki; Morimoto, Hiroshi; Nakano, Takao; Watanabe, Tatsuya; Oda, Kuniyuki; and Tsujihara, Kenji; "Steroselective Synthesis of Antifungal Sulfoximines, Novel Trizaoles II;" Heterocycles, vol. 49, 1998, pp. 181-189.

Reichert, Anja; Frohlich, Roland; Ferguson, Roderick; Kraft, Arno; "Binding Interactions Between 3-aryl-1,2,4-oxadiazol-5-ones and a trisimidazoline base;" J. Chem. Soc., Perkin Trans. 1, 2001, pp. 1321-1328.

Garcia Mancheno, Olga; Bistri, Olivia; and Bolm, Carsten; "Iodinane- and Metal-Free Synthesis of N-Cyano Sulfilimines: Novel and Easy Access of NH-Sulfoximines;" Organic Letters, 2007, vol. 9, No. 19, pp. 3809-3811.

Kiriyama K et al: Insecticidal and neuroblocking activities of acetamiprid and related compounds Journal of Pesticide Sciences, Pesticide Science Society, Tokyo, JP, vol. 28, No. 1, 2003, pp. 80-117.

F Zaragoza Dorwald Side Reactions in Organic Synthesis 2005, Wiley-VCH.

Tetrahedron Letters, vol. 19, No. 6, 1978, pp. 503-506 , p. 504; compounds 7,8.

Organic Mass Spectrometry, vol. 9, 1974, pp. 422-434, table 1 p. 431.

Yoshida H et al: "The Cycloaddition reaction of N-Imidoyl Sulfoximides with Diphenylcyclopropenone to yield Pyrimidinone or Pyrrolinone derivatives" Bulletin of the Chemical Society of Japan, Chemical Society of Japan, Tokyo, JP, vol. 56, No. 8, Aug. 1, 1983, pp. 2438-2441.

Wehr R: "Dimethylsulphoxylideneureas and Dimethylsulphoxylidenethioureas" Journal of the Chemical Society, Chemical Society, Letchworth., GB, Jan. 1, 1965, pp. 3004-3005.

Garapon et al: "n DEG 500.- Reactions D'Eliminations Sur Les O-Chlorobenzoates D'Anilide -Oximes Formation Des Aryliminonitrenes Sous L'Action Des Bases Azotees", Bulletin De La Societe Chimique De France, Societe Francaise De Chimie. Paris, France, Jan. 1, 1975, pp. 2677-2681.

Journal of Organic Chemistry, vol. 44, 1979, pp. 2510-2513.

Ortho-Lithiation of S-tert-butyl-S-phenylsulfoximines. New route to enantiopure sulfinemides via a de-tert-butylation reaction, Stephane Gaillard, Jun. 15, 2005.

Silverman, R. "The Organic Chemistry of Drug Design and Drug Addiction," 2004, Elsevier, pp. 29-32.

\* cited by examiner

PESTICIDES

CROSS REFERENCE TO RELATED APPLICATION

This application claims the benefit of U.S. Provisional Application Ser. No. 61/067,874 filed on Mar. 3, 2008. This application claims the benefit of U.S. Non-Provisional application Ser. No. 12/394,905 filed on 27 Feb. 2009. This application claims the benefit of U.S. Non-Provisional application Ser. No. 12/962,114 filed on 7 Dec. 2010.

FIELD OF THE INVENTION

The invention disclosed in this document is related to the field of pesticides and their use in controlling pests.

BACKGROUND OF THE INVENTION

Pests cause millions of human deaths around the world each year. Furthermore, there are more than ten thousand species of pests that cause losses in agriculture. These agricultural losses amount to billions of U.S. dollars each year. Termites cause damage to various structures such as homes. These termite damage losses amount to billions of U.S. dollars each year. As a final note, many stored food pests eat and adulterate stored food. These stored food losses amount to billions of U.S. dollars each year, but more importantly, deprive people of needed food.

There is an acute need for new pesticides. Insects are developing resistance to pesticides in current use. Hundreds of insect species are resistant to one or more pesticides. The development of resistance to some of the older pesticides, such as DDT, the carbonates, and the organophosphates, is well known. But resistance has even developed to some of the newer pesticides. Therefore, a need exists for new pesticides and particularly for pesticides that have new modes of action.

Substituents (Non Exhaustive List)

The examples given for the substituents are (except for halo) non-exhaustive and must not be construed as limiting the invention disclosed in this document.

"alkenyl" means an acyclic, unsaturated (at least one carbon-carbon double bond), branched or unbranched, substituent consisting of carbon and hydrogen, for example, vinyl, allyl, butenyl, pentenyl, hexenyl, heptenyl, octenyl, nonenyl, and decenyl.

"alkenyloxy" means an alkenyl further consisting of a carbon-oxygen single bond, for example, allyloxy, butenyloxy, pentenyloxy, hexenyloxy, heptenyloxy, octenyloxy, nonenyloxy, and decenyloxy.

"alkoxy" means an alkyl further consisting of a carbon-oxygen single bond, for example, methoxy, ethoxy, propoxy, isopropoxy, 1-butoxy, 2-butoxy, isobutoxy, tert-butoxy, pentoxy, 2-methylbutoxy, 1,1-dimethylpropoxy, hexoxy, heptoxy, octoxy, nonoxy, and decoxy.

"alkyl" means an acyclic, saturated, branched or unbranched, substituent consisting of carbon and hydrogen, for example, methyl, ethyl, propyl, isopropyl, 1-butyl, 2-butyl, isobutyl, tert-butyl, pentyl, 2-methylbutyl, 1,1-dimethylpropyl, hexyl, heptyl, octyl, nonyl, and decyl.

"alkynyl" means an acyclic, unsaturated (at least one carbon-carbon triple bond, and any double bonds), branched or unbranched, substituent consisting of carbon and hydrogen, for example, ethynyl, propargyl, butynyl, pentynyl, hexynyl, heptynyl, octynyl, nonynyl, and decynyl.

"alkynyloxy" means an alkynyl further consisting of a carbon-oxygen single bond, for example, pentynyloxy, hexynyloxy, heptynyloxy, octynyloxy, nonynyloxy, and decynyloxy.

"aryl" means a cyclic, aromatic substituent consisting of hydrogen and carbon, for example, phenyl, naphthyl, fluorenyl, and biphenyl.

"cycloalkenyl" means a monocyclic or polycyclic, unsaturated (at least one carbon-carbon double bond) substituent consisting of carbon and hydrogen, for example, cyclobutenyl, cyclopentenyl, cyclohexenyl, cycloheptenyl, cyclooctenyl, cyclodecenyl, norbornenyl, bicyclo[2.2.2]octenyl, tetrahydronaphthyl, hexahydronaphthyl, and octahydronaphthyl.

"cycloalkenyloxy" means a cycloalkenyl further consisting of a carbon-oxygen single bond, for example, cyclobutenyloxy, cyclopentenyloxy, cyclohexenyloxy, cycloheptenyloxy, cyclooctenyloxy, cyclodecenyloxy, norbornenyloxy, and bicyclo[2.2.2]octenyloxy.

"cycloalkyl" means a monocyclic or polycyclic, saturated substituent consisting of carbon and hydrogen, for example, cyclopropyl, cyclobutyl, cyclopentyl, cyclohexyl, cycloheptyl, cyclooctyl, cyclodecyl, norbornyl, bicyclo[2.2.2]octyl, and decahydronaphthyl.

"cycloalkoxy" means a cycloalkyl further consisting of a carbon-oxygen single bond, for example, cyclopropyloxy, cyclobutyloxy, cyclopentyloxy, cyclohexyloxy, cycloheptyloxy, cyclooctyloxy, cyclodecyloxy, norbornyloxy, and bicyclo[2.2.2]octyloxy.

"halo" means fluoro, chloro, bromo, and iodo.

"haloalkyl" means an alkyl further consisting of, from one to the maximum possible number of, identical or different, halos, for example, fluoromethyl, difluoromethyl, trifluoromethyl, 1-fluoromethyl, 2-fluoroethyl, 2,2,2-trifluoroethyl, chloromethyl, trichloromethyl, and 1,1,2,2-tetrafluoroethyl.

"heterocyclyl" means a cyclic substituent that may be fully saturated, partially unsaturated, or fully unsaturated, where the cyclic structure contains at least one carbon and at least one heteroatom, where said heteroatom is nitrogen, sulfur, or oxygen, for example, benzofuranyl, benzoisothiazolyl, benzoisoxazolyl, benzoxazolyl, benzothienyl, benzothiazolyl cinnolinyl, furanyl, indazolyl, indolyl, imidazolyl, isoindolyl, isoquinolinyl, isothiazolyl, isoxazolyl, oxiranyl, 1,3,4-oxadiazolyl, oxazolinyl, oxazolyl, phthalazinyl, pyrazinyl, pyrazolinyl, pyrazolyl, pyridazinyl, pyridyl, pyrimidinyl, pyrrolyl, quinazolinyl, quinolinyl, quinoxalinyl, 1,2,3,4-tetrazolyl, thiazolinyl, thiazolyl, thienyl, 1,2,3-triazinyl, 1,2,4-triazinyl, 1,3,5-triazinyl, 1,2,3-triazolyl, and 1,2,4-triazolyl.

DETAILED DESCRIPTION OF THE INVENTION

The compounds of this invention have the following generic formula (I)

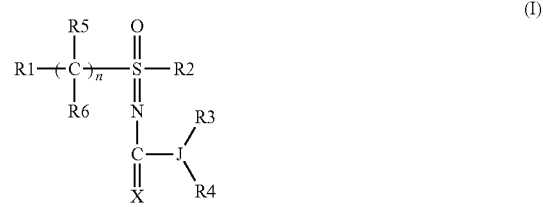

wherein:
(a) R1 is $C_2$-$C_8$ alkenyl, $C_2$-$C_8$ alkenyloxy, $C_2$-$C_8$ alkenylthio, $C_1$-$C_8$ alkoxy, $C_1$-$C_8$ alkyl, $C_1$-$C_8$ alkylthio, $C_2$-$C_8$ alkynyl, $C_2$-$C_8$ alkynyloxy, $C_2$-$C_8$ alkynylthio, aryl, $C_3$-$C_8$ cycloalkenyl, $C_3$-$C_8$ cycloalkenyloxy, $C_3$-$C_8$ cycloalkenylthio, $C_3$-$C_8$ cycloalkyl, $C_3$-$C_8$ cycloalkoxy, $C_3$-$C_8$ cycloalkylthio, heterocyclyl, or $C_0$-$C_8$ alkyl-C(=O)OR8, wherein each of which may be independently substituted with one or more of the following substituents, F, Cl, Br, I, CN, $NO_2$, $C_1$-$C_6$ alkyl, $C_2$-$C_6$ alkenyl, $C_2$-$C_6$ alkynyl, $C_1$-$C_6$ alkoxy, $C_1$-$C_6$ haloalkyl, $C_1$-$C_6$ haloalkoxy, $C_1$-$C_6$ haloalkylthio, $S(=O)_{n1}C_1$-$C_6$ alkyl (where n1=0-2), $S(=O)_{n1}C_1$-$C_6$ haloalkyl (where n1=0-2), $OSO_2C_1$-$C_6$ haloalkyl, C(=O)O$C_1$-$C_6$ alkyl, C(=O)$C_1$-$C_6$ alkyl, C(=O)$C_1$-$C_6$ haloalkyl, aryl, $C_1$-$C_6$ hydroxyalkyl, NR9R10, and heterocyclyl;

(b) R2 is $C_2$-$C_8$ alkenyl, $C_2$-$C_8$ alkenyloxy, $C_2$-$C_8$ alkenylthio, $C_1$-$C_8$ alkoxy, $C_1$-$C_8$ alkyl, $C_1$-$C_8$ alkylthio, $C_2$-$C_8$ alkynyl, $C_2$-$C_8$ alkynyloxy, $C_2$-$C_8$ alkynylthio, aryl, $C_3$-$C_8$ cycloalkenyl, $C_3$-$C_8$ cycloalkenyloxy, $C_3$-$C_8$ cycloalkenylthio, $C_3$-$C_8$ cycloalkyl, $C_3$-$C_8$ cycloalkoxy, $C_3$-$C_8$ cycloalkylthio, heterocyclyl, or $C_0$-$C_8$ alkyl-C(=O)OR8, wherein each of which may be independently substituted with one or more of the following substituents, F, Cl, Br, I, CN, $NO_2$, $C_1$-$C_6$ alkyl, $C_2$-$C_6$ alkenyl, $C_2$-$C_6$ alkynyl, $C_1$-$C_6$ alkoxy, $C_1$-$C_6$ haloalkyl, $C_1$-$C_6$ haloalkoxy, $C_1$-$C_6$ haloalkylthio, $S(=O)_{n1}C_1$-$C_6$ alkyl (where n1=0-2), $S(=O)_{n1}C_1$-$C_6$ haloalkyl (where n1=0-2), $OSO_2C_1$-$C_6$ haloalkyl, C(=O)O$C_1$-$C_6$ alkyl, C(=O)$C_1$-$C_6$ alkyl, C(=O)$C_1$-$C_6$ haloalkyl, aryl, $C_1$-$C_6$ hydroxyalkyl, NR9R10, and heterocyclyl, and wherein R2 and R5 may also form a 4, 5, or 6 membered ring;

(c) R3 is F, Cl, Br, I, $C_2$-$C_8$ alkenyl, $C_2$-$C_8$ alkenyloxy, $C_2$-$C_8$ alkenylthio, $C_1$-$C_8$ alkoxy, $C_1$-$C_8$ alkyl, $C_1$-$C_8$ alkylthio, $C_2$-$C_8$ alkynyl, $C_2$-$C_8$ alkynyloxy, $C_2$-$C_8$ alkynylthio, aryl, $C_3$-$C_8$ cycloalkenyl, $C_3$-$C_8$ cycloalkenyloxy, $C_3$-$C_8$ cycloalkenylthio, $C_3$-$C_8$ cycloalkyl, $C_3$-$C_8$ cycloalkoxy, $C_3$-$C_8$ cycloalkylthio, H, heterocyclyl, C(=O)$C_1$-$C_6$ alkyl, C(=O)$C_1$-$C_6$ aryl, or $C_0$-$C_8$ alkyl-C(=O)OR8, wherein each of which may be independently substituted (except for H, F, Cl, Br, I) with one or more of the following substituents, F, Cl, Br, I, CN, $NO_2$, $C_1$-$C_6$ alkyl, $C_2$-$C_6$ alkenyl, $C_2$-$C_6$ alkynyl, $C_1$-$C_6$ alkoxy, $C_1$-$C_6$ haloalkyl, $C_1$-$C_6$ haloalkoxy, $C_1$-$C_6$ haloalkylthio, $S(=O)_{n1}C_1$-$C_6$ alkyl (where n1=0-2), $S(=O)_{n1}C_1$-$C_6$ haloalkyl (where n1=0-2), $OSO_2C_1$-$C_6$ haloalkyl, C(=O)O$C_1$-$C_6$ alkyl, C(=O)$C_1$-$C_6$ alkyl, C(=O)$C_1$-$C_6$ haloalkyl, aryl (wherein said aryl may be substituted with one or more substituents selected from F, Cl, Br, I, or $C_1$-$C_8$ alkoxy) $C_1$-$C_6$ hydroxyalkyl, NR9R10, and heterocyclyl, and wherein R3 and R4 may also form a 4, 5, or 6 membered ring;

(d) R4 is F, Cl, Br, I, $C_2$-$C_8$ alkenyl, $C_2$-$C_8$ alkenyloxy, $C_2$-$C_8$ alkenylthio, $C_1$-$C_8$ alkoxy, $C_1$-$C_8$ alkyl, $C_1$-$C_8$ alkylthio, $C_2$-$C_8$ alkynyl, $C_2$-$C_8$ alkynyloxy, $C_2$-$C_8$ alkynylthio, aryl, $C_3$-$C_8$ cycloalkenyl, $C_3$-$C_8$ cycloalkenyloxy, $C_3$-$C_8$ cycloalkenylthio, $C_3$-$C_8$ cycloalkyl, $C_3$-$C_8$ cycloalkoxy, $C_3$-$C_8$ cycloalkylthio, H, heterocyclyl, C(=O)$C_1$-$C_6$ alkyl, C(=O)$C_1$-$C_6$ aryl, or $C_0$-$C_8$ alkyl-C(=O)OR8, wherein each of which may be independently substituted (except for H, F, Cl, Br, I) with one or more of the following substituents, F, Cl, Br, I, CN, $NO_2$, $C_1$-$C_6$ alkyl, $C_2$-$C_6$ alkenyl, $C_2$-$C_6$ alkynyl, $C_1$-$C_6$ alkoxy, $C_1$-$C_6$ haloalkyl, $C_1$-$C_6$ haloalkoxy, $C_1$-$C_6$ haloalkylthio, $S(=O)_{n1}C_1$-$C_6$ alkyl (where n1=0-2), $S(=O)_{n1}C_1$-$C_6$ haloalkyl (where n1=0-2), $OSO_2C_1$-$C_6$ haloalkyl, C(=O)O$C_1$-$C_6$ alkyl, C(=O)$C_1$-$C_6$ alkyl, C(=O)$C_1$-$C_6$ haloalkyl, aryl (wherein said aryl may be substituted with one or more substituents selected from F, Cl, Br, I, or $C_1$-$C_8$ alkoxy) $C_1$-$C_6$ hydroxyalkyl, NR9R10, and heterocyclyl, and wherein R3 and R4 may also form a 4, 5, or 6 membered ring;

(e) R5 is $C_2$-$C_8$ alkenyl, $C_2$-$C_8$ alkenyloxy, $C_2$-$C_8$ alkenylthio, $C_1$-$C_8$ alkoxy, $C_1$-$C_8$ alkyl, $C_1$-$C_8$ alkylthio, $C_2$-$C_8$ alkynyl, $C_2$-$C_8$ alkynyloxy, $C_2$-$C_8$ alkynylthio, aryl, $C_3$-$C_8$ cycloalkenyl, $C_3$-$C_8$ cycloalkenyloxy, $C_3$-$C_8$ cycloalkenylthio, $C_3$-$C_8$ cycloalkyl, $C_3$-$C_8$ cycloalkoxy, $C_3$-$C_8$ cycloalkylthio, H, heterocyclyl, or $C_0$-$C_8$ alkyl-C(=O)OR8, wherein each of which may be independently substituted (except for H) with one or more of the following substituents, F, Cl, Br, I, CN, $NO_2$, $C_1$-$C_6$ alkyl, $C_2$-$C_6$ alkenyl, $C_2$-$C_6$ alkynyl, $C_1$-$C_6$ alkoxy, $C_1$-$C_6$ haloalkyl, $C_1$-$C_6$ haloalkoxy, $C_1$-$C_6$ haloalkylthio, $S(=O)_{n1}C_1$-$C_6$ alkyl (where n1=0-2), $S(=O)_{n1}C_1$-$C_6$ haloalkyl (where n1=0-2), $OSO_2C_1$-$C_6$ haloalkyl, C(=O)O$C_1$-$C_6$ alkyl, C(=O)$C_1$-$C_6$ alkyl, C(=O)$C_1$-$C_6$ haloalkyl, aryl, $C_3$-$C_8$ cycloalkyl, $C_1$-$C_6$ hydroxyalkyl, NR9R10, and heterocyclyl, and wherein R2 and R5 may also form a 4, 5, or 6 membered ring, and wherein R5 and R6 may also form a 3, 4, 5, or 6 membered ring;

(f) R6 is $C_2$-$C_8$ alkenyl, $C_2$-$C_8$ alkenyloxy, $C_2$-$C_8$ alkenylthio, $C_1$-$C_8$ alkoxy, $C_1$-$C_8$ alkyl, $C_1$-$C_8$ alkylthio, $C_2$-$C_8$ alkynyl, $C_2$-$C_8$ alkynyloxy, $C_2$-$C_8$ alkynylthio, aryl, $C_3$-$C_8$ cycloalkenyl, $C_3$-$C_8$ cycloalkenyloxy, $C_3$-$C_8$ cycloalkenylthio, $C_3$-$C_8$ cycloalkyl, $C_3$-$C_8$ cycloalkoxy, $C_3$-$C_8$ cycloalkylthio, H, heterocyclyl, or $C_0$-$C_8$ alkyl-C(=O)OR8, wherein each of which may be independently substituted (except for H) with one or more of the following substituents, F, Cl, Br, I, CN, $NO_2$, $C_1$-$C_6$ alkyl, $C_2$-$C_6$ alkenyl, $C_2$-$C_6$ alkynyl, $C_1$-$C_6$ alkoxy, $C_1$-$C_6$ haloalkyl, $C_1$-$C_6$ haloalkoxy, $C_1$-$C_6$ haloalkylthio, $S(=O)_{n1}C_1$-$C_6$ alkyl (where n1=0-2), $S(=O)_{n1}C_1$-$C_6$ haloalkyl (where n1=0-2), $OSO_2C_1$-$C_6$ haloalkyl, C(=O)O$C_1$-$C_6$ alkyl, C(=O)$C_1$-$C_6$ alkyl, C(=O)$C_1$-$C_6$ haloalkyl, aryl, $C_3$-$C_8$ cycloalkyl, $C_1$-$C_6$ hydroxyalkyl, NR9R10, and heterocyclyl, and wherein R2 and R5 may also form a 4, 5, or 6 membered ring, and wherein R5 and R6 may also form a 3, 4, 5, or 6 membered ring;

(g) n is 0 to 4;
(h) X is NR8, O, or S;
(i) J is N or CR7;
(j) R7 is H, F, Cl, Br, I, $C_2$-$C_8$ alkenyl, $C_2$-$C_8$ alkenyloxy, $C_2$-$C_8$ alkenylthio, $C_1$-$C_8$ alkoxy, $C_1$-$C_8$ alkyl, $C_1$-$C_8$ alkylthio, $C_2$-$C_8$ alkynyl, $C_2$-$C_8$ alkynyloxy, $C_2$-$C_8$ alkynylthio, aryl, $C_3$-$C_8$ cycloalkenyl, $C_3$-$C_8$ cycloalkenyloxy, $C_3$-$C_8$ cycloalkenylthio, $C_3$-$C_8$ cycloalkyl, $C_3$-$C_8$ cycloalkoxy, $C_3$-$C_8$ cycloalkylthio, heterocyclyl, or $C_0$-$C_8$ alkyl-C(=O)OR8, wherein each of which may be independently substituted (except for H, F, Cl, Br, I) with one or more of the following substituents, F, Cl, Br, I, CN, $NO_2$, $C_1$-$C_6$ alkyl, $C_2$-$C_6$ alkenyl, $C_2$-$C_6$ alkynyl, $C_1$-$C_6$ alkoxy, $C_1$-$C_6$ haloalkyl, $C_1$-$C_6$ haloalkoxy, $C_1$-$C_6$ haloalkylthio, $S(=O)_{n1}C_1$-$C_6$ alkyl (where n1=0-2), $S(=O)_{n1}C_1$-$C_6$ haloalkyl (where n1=0-2), $OSO_2C_1$-$C_6$ haloalkyl, C(=O)O$C_1$-$C_6$ alkyl, C(=O)$C_1$-$C_6$ alkyl, C(=O)$C_1$-$C_6$ haloalkyl, aryl, $C_1$-$C_6$ hydroxyalkyl, NR9R10 and heterocyclyl;

(k) R8 is H, OH, OC(=O)$C_1$-$C_6$ alkyl, $C_2$-$C_8$ alkenyl, $C_2$-$C_8$ alkenyloxy, $C_2$-$C_8$ alkenylthio, $C_1$-$C_8$ alkoxy, $C_1$-$C_8$ alkyl, $C_1$-$C_8$ alkylthio, $C_2$-$C_8$ alkynyl, $C_2$-$C_8$ alkynyloxy, $C_2$-$C_8$ alkynylthio, aryl, $C_3$-$C_8$ cycloalkenyl, $C_3$-$C_8$ cycloalkenyloxy, $C_3$-$C_8$ cycloalkenylthio, $C_3$-$C_8$ cycloalkyl, $C_3$-$C_8$ cycloalkoxy, $C_3$-$C_8$ cycloalkylthio, or heterocyclyl, wherein each of which may be independently substituted with one or more of the following substituents, F, Cl, Br, I, CN, $NO_2$, $C_1$-$C_6$ alkyl, $C_2$-$C_6$ alkenyl, $C_2$-$C_6$ alkynyl, $C_1$-$C_6$ alkoxy, $C_3$-$C_8$ cycloalkyl, $C_3$-$C_8$ halocycloalkyl, $C_1$-$C_6$ haloalkyl, $C_1$-$C_6$ haloalkoxy, $C_1$-$C_6$ haloalkylthio, $S(=O)_{n1}C_1$-$C_6$ alkyl (where n1=0-2), $S(=O)_{n1}C_1$-$C_6$ haloalkyl (where n1=0-2), $OSO_2C_1$-$C_6$ haloalkyl, $C(=O)OC_1$-$C_6$ alkyl, $C(=O)C_1$-$C_6$ alkyl, $C(=O)C_1$-$C_6$ haloalkyl, aryl (wherein said aryl may be substituted with one or more substituents selected from F, Cl, Br, I, or $C_1$-$C_8$ alkoxy), $C_1$-$C_6$ hydroxyalkyl, and heterocyclyl;

(l) R9 is $C_2$-$C_8$ alkenyl, $C_2$-$C_8$ alkenyloxy, $C_2$-$C_8$ alkenylthio, $C_1$-$C_8$ alkoxy, $C_1$-$C_8$ alkyl, $C_1$-$C_8$ alkylthio, $C_2$-$C_8$ alkynyl, $C_2$-$C_8$ alkynyloxy, $C_2$-$C_8$ alkynylthio, aryl, $C_3$-$C_8$ cycloalkenyl, $C_3$-$C_8$ cycloalkenyloxy, $C_3$-$C_8$ cycloalkenylthio, $C_3$-$C_8$ cycloalkyl, $C_3$-$C_8$ cycloalkoxy, $C_3$-$C_8$ cycloalkylthio, or heterocyclyl, wherein each of which may be independently substituted with one or more of the following substituents, F, Cl, Br, I, CN, $NO_2$, $C_1$-$C_6$ alkyl, $C_2$-$C_6$ alkenyl, $C_2$-$C_6$ alkynyl, $C_1$-$C_6$ alkoxy, $C_1$-$C_6$ haloalkyl, $C_1$-$C_6$ haloalkoxy, $C_1$-$C_6$ haloalkylthio, $S(=O)_{n1}C_1$-$C_6$ alkyl (where n1=0-2), $S(=O)_{n1}C_1$-$C_6$ haloalkyl (where n1=0-2), $OSO_2C_1$-$C_6$ haloalkyl, $C(=O)OC_1$-$C_6$ alkyl, $C(=O)C_1$-$C_6$ alkyl, $C(=O)C_1$-$C_6$ haloalkyl, aryl, $C_1$-$C_6$ hydroxyalkyl, and heterocyclyl, and wherein R9 and R10 may also form a 4, 5, or 6 membered ring; and (m) R10 is $C_2$-$C_8$ alkenyl, $C_2$-$C_8$ alkenyloxy, $C_2$-$C_8$ alkenylthio, $C_1$-$C_8$ alkoxy, $C_1$-$C_8$ alkyl, $C_1$-$C_8$ alkylthio, $C_2$-$C_8$ alkynyl, $C_2$-$C_8$ alkynyloxy, $C_2$-$C_8$ alkynylthio, aryl, $C_3$-$C_8$ cycloalkenyl, $C_3$-$C_8$ cycloalkenyloxy, $C_3$-$C_8$ cycloalkenylthio, $C_3$-$C_8$ cycloalkyl, $C_3$-$C_8$ cycloalkoxy, $C_3$-$C_8$ cycloalkylthio, or heterocyclyl, wherein each of which may be independently substituted with one or more of the following substituents, F, Cl, Br, I, CN, $NO_2$, $C_1$-$C_6$ alkyl, $C_2$-$C_6$ alkenyl, $C_2$-$C_6$ alkynyl, $C_1$-$C_6$ alkoxy, $C_1$-$C_6$ haloalkyl, $C_1$-$C_6$ haloalkoxy, $C_1$-$C_6$ haloalkylthio, $S(=O)_{n1}C_1$-$C_6$ alkyl (where n1=0-2), $S(=O)_{n1}C_1$-$C_6$ haloalkyl (where n1=0-2), $OSO_2C_1$-$C_6$ haloalkyl, $C(=O)OC_1$-$C_6$ alkyl, $C(=O)C_1$-$C_6$ alkyl, $C(=O)C_1$-$C_6$ haloalkyl, aryl, $C_1$-$C_6$ hydroxyalkyl, and heterocyclyl, and wherein R9 and R10 may also form a 4, 5, or 6 membered ring.

In another embodiment of this invention, R1 is aryl or heterocyclyl, wherein each of which may be independently substituted with one or more of the following substituents F, Cl, Br, I, $C_1$-$C_6$ alkyl or $C_1$-$C_6$ haloalkyl.

In another embodiment of this invention, R1 is an heterocyclyl, wherein said heterocyclyl may be independently substituted with one or more of the following substituents F, Cl, Br, I, $C_1$-$C_6$ alkyl or $C_1$-$C_6$ haloalkyl.

In another embodiment of this invention, R1 is pyridyl, wherein said pyridyl may be independently substituted with one or more of the following substituents Cl, $CH_3$, or $CF_3$.

In another embodiment of this invention, R1 is pyridyl, wherein said pyridyl is substituted with one of the following substituents Cl, $CH_3$, or $CF_3$ are attached to the carbon atom the sixth position.

In another embodiment of this invention, R2 is a $C_1$-$C_8$ alkyl.

In another embodiment of this invention, R2 is a $CH_3$.

In another embodiment of this invention, R2 and R5 form a six-membered ring composed of carbon, hydrogen, and the sulfur atom.

In another embodiment of this invention, R3 is H, F, or $C_1$-$C_8$ alkyl.

In another embodiment of this invention, R3 and R4 form a five or six-membered ring composed of carbon, hydrogen, and a nitrogen atom.

In another embodiment of this invention, R3 and R4 form a six-membered ring composed of carbon, hydrogen, a nitrogen atom, and an oxygen atom.

In another embodiment, R4 is H, F, aryl, $C(=O)C_1$-$C_6$ alkyl, heterocyclyl, $C_1$-$C_8$ alkyl, $C_3$-$C_8$ cycloalkyl, $C_0$-$C_8$ alkyl-$C(=O)OR8$, $C(=O)C_1$-$C_6$ aryl, wherein each of which may be independently substituted (except for H and F) with one or more of the following substituents, $C_1$, $C_1$-$C_6$ haloalkyl, $C_1$-$C_6$ alkoxy, $C(=O)C_1$-$C_6$ alkyl, NR9R10, and aryl (wherein said aryl may be substituted with one or more substituents selected from F, Cl, Br, I, or $C_1$-$C_8$ alkoxy).

In another embodiment, R4 is H or $C_1$-$C_8$ alkyl (wherein said alkyl may be independently substituted with one or more of the following substituents, $C_1$, $C_1$-$C_6$ haloalkyl, $C_1$-$C_6$ alkoxy, $C(=O)C_1$-$C_6$ alkyl, and aryl (wherein said aryl may be substituted with one or more substituents selected from F, Cl, Br, I, or $C_1$-$C_8$ alkoxy).

In another embodiment of this invention, R5 is H, $C_1$-$C_8$ alkyl, $C_2$-$C_8$ alkenyl, wherein each of which may be independently substituted (except for H) with one or more of the following substituents, F, Cl, Br, I, or $C_3$-$C_8$ cycloalkyl.

In another embodiment of this invention, R5 is H or $C_1$-$C_8$ alkyl.

In another embodiment of this invention R6 is H.

In another embodiment of this invention n is 0 or 1.

In another embodiment of this invention, X is NR8 or S.

In another embodiment of this invention J is N.

In another embodiment of this invention, R7 is H, F, Cl, Br, I, or $C_1$-$C_8$ alkyl.

In another embodiment of this invention, R7 is H.

In another embodiment of this invention, R8 is H, OH, $OC(=O)C_1$-$C_6$ alkyl, $C_1$-$C_8$ alkyl, $C_1$-$C_8$ alkoxy, $C_2$-$C_8$ alkenyloxy, wherein each of which may be independently substituted (except for H and OH) with one or more of the following substituents, aryl (wherein said aryl may be substituted with one or more substituents selected from F, Cl, Br, I, $C_1$-$C_8$ alkoxy), $C_3$-$C_8$ cycloalkyl, $C_3$-$C_8$ halocycloalkyl, F, Cl, Br, I, $C_1$-$C_6$ alkoxy, In another embodiment of the invention:

(a) R1 is $C_2$-$C_8$ alkenyl, $C_2$-$C_8$ alkenyloxy, $C_2$-$C_8$ alkenylthio, $C_1$-$C_8$ alkoxy, $C_1$-$C_8$ alkyl, $C_1$-$C_8$ alkylthio, $C_2$-$C_8$ alkynyl, $C_2$-$C_8$ alkynyloxy, $C_2$-$C_8$ alkynylthio, aryl, $C_3$-$C_8$ cycloalkenyl, $C_3$-$C_8$ cycloalkenyloxy, $C_3$-$C_8$ cycloalkenylthio, $C_3$-$C_8$ cycloalkyl, $C_3$-$C_8$ cycloalkoxy, $C_3$-$C_8$ cycloalkylthio, heterocyclyl, or $C_0$-$C_8$ alkyl-$C(=O)OR8$, wherein each of which may be independently substituted with one or more of the following substituents, F, Cl, Br, I, CN, $NO_2$, $C_1$-$C_6$ alkyl, $C_2$-$C_6$ alkenyl, $C_2$-$C_6$ alkynyl, $C_1$-$C_6$ alkoxy, $C_1$-$C_6$ haloalkyl, $C_1$-$C_6$ haloalkoxy, $C_1$-$C_6$ haloalkylthio, $S(=O)_{n1}C_1$-$C_6$ alkyl (where n1=0-2), $S(=O)_{n1}C_1$-$C_6$ haloalkyl (where n=0-2), $OSO_2C_1$-$C_6$ haloalkyl, $C(=O)OC_1$-$C_6$ alkyl, $C(=O)C_1$-$C_6$ alkyl, $C(=O)C_1$-$C_6$ haloalkyl, aryl, $C_1$-$C_6$ hydroxyalkyl, NR9R10 and heterocyclyl;

(b) R2 is $C_2$-$C_8$ alkenyl, $C_2$-$C_8$ alkenyloxy, $C_2$-$C_8$ alkenylthio, $C_1$-$C_8$ alkoxy, $C_1$-$C_8$ alkyl, $C_1$-$C_8$ alkylthio, $C_2$-$C_8$ alkynyl, $C_2$-$C_8$ alkynyloxy, $C_2$-$C_8$ alkynylthio, aryl, $C_3$-$C_8$ cycloalkenyl, $C_3$-$C_8$ cycloalkenyloxy, $C_3$-$C_8$ cycloalkenylthio, $C_3$-$C_8$ cycloalkyl, $C_3$-$C_8$ cycloalkoxy, $C_3$-$C_8$ cycloalkylthio, heterocyclyl, or $C_0$-$C_8$ alkyl-$C(=O)OR8$, wherein each of which may be independently substituted with one or more of the following substituents, F, Cl, Br, I, CN, $NO_2$, $C_1$-$C_6$ alkyl, $C_2$-$C_6$ alkenyl, $C_2$-$C_6$ alkynyl, $C_1$-$C_6$ alkoxy, $C_1$-$C_6$ haloalkyl, $C_1$-$C_6$ haloalkoxy, $C_1$-$C_6$ haloalkylthio, $S(=O)_{n1}C_1$-$C_6$ alkyl (where n1=0-2), $S(=O)_{n1}C_1$-$C_6$ haloalkyl (where n1=0-2), $OSO_2C_1$-$C_6$ haloalkyl, $C(=O)OC_1$-$C_6$ alkyl, $C(=O)C_1$-$C_6$ alkyl, $C(=O)C_1$-$C_6$ haloalkyl, aryl, $C_1$-$C_6$ hydroxyalkyl, NR9R10 and heterocyclyl, and wherein R2 and R5 may also form a 4, 5, or 6, membered ring;

(c) R3 is $C_2$-$C_8$ alkenyl, $C_2$-$C_8$ alkenyloxy, $C_2$-$C_8$ alkenylthio, $C_1$-$C_8$ alkoxy, $C_1$-$C_8$ alkyl, $C_1$-$C_8$ alkylthio, $C_2$-$C_8$ alkynyl, $C_2$-$C_8$ alkynyloxy, $C_2$-$C_8$ alkynylthio, aryl, $C_3$-$C_8$ cycloalkenyl, $C_3$-$C_8$ cycloalkenyloxy, $C_3$-$C_8$ cycloalkenylthio, $C_3$-$C_8$ cycloalkyl, $C_3$-$C_8$ cycloalkoxy, $C_3$-$C_8$ cycloalkylthio, H, heterocyclyl, or $C_0$-$C_8$ alkyl-C(=O)OR8, wherein each of which may be independently substituted (except for H) with one or more of the following substituents, F, Cl, Br, I, CN, $NO_2$, $C_1$-$C_6$ alkyl, $C_2$-$C_6$ alkenyl, $C_2$-$C_6$ alkynyl, $C_1$-$C_6$ alkoxy, $C_1$-$C_6$ haloalkyl, $C_1$-$C_6$ haloalkoxy, $C_1$-$C_6$ haloalkylthio, $S(=O)_{n1}C_1$-$C_6$ alkyl (where n1=0-2), $S(=O)_{n1}C_1$-$C_6$ haloalkyl (where n1=0-2), $OSO_2C_1$-$C_6$ haloalkyl, C(=O)O$C_1$-$C_6$ alkyl, C(=O)$C_1$-$C_6$ alkyl, C(=O)$C_1$-$C_6$ haloalkyl, aryl, $C_1$-$C_6$ hydroxyalkyl, NR9R10 and heterocyclyl, and wherein R3 and R4 may also form a 4, 5, or 6, membered ring;

(d) R4 is $C_2$-$C_8$ alkenyl, $C_2$-$C_8$ alkenyloxy, $C_2$-$C_8$ alkenylthio, $C_1$-$C_8$ alkoxy, $C_1$-$C_8$ alkyl, $C_1$-$C_8$ alkylthio, $C_2$-$C_8$ alkynyl, $C_2$-$C_8$ alkynyloxy, $C_2$-$C_8$ alkynylthio, aryl, $C_3$-$C_8$ cycloalkenyl, $C_3$-$C_8$ cycloalkenyloxy, $C_3$-$C_8$ cycloalkenylthio, $C_3$-$C_8$ cycloalkyl, $C_3$-$C_8$ cycloalkoxy, $C_3$-$C_8$ cycloalkylthio, H, heterocyclyl, or $C_0$-$C_8$ alkyl-C(=O)OR8, wherein each of which may be independently substituted (except for H) with one or more of the following substituents, F, Cl, Br, I, CN, $NO_2$, $C_1$-$C_6$ alkyl, $C_2$-$C_6$ alkenyl, $C_2$-$C_6$ alkynyl, $C_1$-$C_6$ alkoxy, $C_1$-$C_6$ haloalkyl, $C_1$-$C_6$ haloalkoxy, $C_1$-$C_6$ haloalkylthio, $S(=O)_{n1}C_1$-$C_6$ alkyl (where n1=0-2), $S(=O)_{n1}C_1$-$C_6$ haloalkyl (where n1=0-2), $OSO_2C_1$-$C_6$ haloalkyl, C(=O)O$C_1$-$C_6$ alkyl, C(=O)$C_1$-$C_6$ alkyl, C(=O)$C_1$-$C_6$ haloalkyl, aryl, $C_1$-$C_6$ hydroxyalkyl, NR9R10 and heterocyclyl, and wherein R3 and R4 may also form a 4, 5, or 6, membered ring;

(e) R5 is $C_2$-$C_8$ alkenyl, $C_2$-$C_8$ alkenyloxy, $C_2$-$C_8$ alkenylthio, $C_1$-$C_8$ alkoxy, $C_1$-$C_8$ alkyl, $C_1$-$C_8$ alkylthio, $C_2$-$C_8$ alkynyl, $C_2$-$C_8$ alkynyloxy, $C_2$-$C_8$ alkynylthio, aryl, $C_3$-$C_8$ cycloalkenyl, $C_3$-$C_8$ cycloalkenyloxy, $C_3$-$C_8$ cycloalkenylthio, $C_3$-$C_8$ cycloalkyl, $C_3$-$C_8$ cycloalkoxy, $C_3$-$C_8$ cycloalkylthio, H, heterocyclyl, or $C_0$-$C_8$ alkyl-C(=O)OR8, wherein each of which may be independently substituted (except for H) with one or more of the following substituents, F, Cl, Br, I, CN, $NO_2$, $C_1$-$C_6$ alkyl, $C_2$-$C_6$ alkenyl, $C_2$-$C_6$ alkynyl, $C_1$-$C_6$ alkoxy, $C_1$-$C_6$ haloalkyl, $C_1$-$C_6$ haloalkoxy, $C_1$-$C_6$ haloalkylthio, $S(=O)_{n1}C_1$-$C_6$ alkyl (where n1=0-2), $S(=O)_{n1}C_1$-$C_6$ haloalkyl (where n1=0-2), $OSO_2C_1$-$C_6$ haloalkyl, C(=O)O$C_1$-$C_6$ alkyl, C(=O)$C_1$-$C_6$ alkyl, C(=O)$C_1$-$C_6$ haloalkyl, aryl, $C_1$-$C_6$ hydroxyalkyl, NR9R10 and heterocyclyl, and wherein R2 and R5 may also form a 4, 5, or 6, membered ring, and wherein R5 and R6 may also form a 3, 4, 5, or 6, membered ring;

(f) R6 is $C_2$-$C_8$ alkenyl, $C_2$-$C_8$ alkenyloxy, $C_2$-$C_8$ alkenylthio, $C_1$-$C_8$ alkoxy, $C_1$-$C_8$ alkyl, $C_1$-$C_8$ alkylthio, $C_2$-$C_8$ alkynyl, $C_2$-$C_8$ alkynyloxy, $C_2$-$C_8$ alkynylthio, aryl, $C_3$-$C_8$ cycloalkenyl, $C_3$-$C_8$ cycloalkenyloxy, $C_3$-$C_8$ cycloalkenylthio, $C_3$-$C_8$ cycloalkyl, $C_3$-$C_8$ cycloalkoxy, $C_3$-$C_8$ cycloalkylthio, H, heterocyclyl, or $C_0$-$C_8$ alkyl-C(=O)OR8, wherein each of which may be independently substituted (except for H) with one or more of the following substituents, F, Cl, Br, I, CN, $NO_2$, $C_1$-$C_6$ alkyl, $C_2$-$C_6$ alkenyl, $C_2$-$C_6$ alkynyl, $C_1$-$C_6$ alkoxy, $C_1$-$C_6$ haloalkyl, $C_1$-$C_6$ haloalkoxy, $C_1$-$C_6$ haloalkylthio, $S(=O)_{n1}C_1$-$C_6$ alkyl (where n1=0-2), $S(=O)_{n1}C_1$-$C_6$ haloalkyl (where n1=0-2), $OSO_2C_1$-$C_6$ haloalkyl, C(=O)O$C_1$-$C_6$ alkyl, C(=O)$C_1$-$C_6$ alkyl, C(=O)$C_1$-$C_6$ haloalkyl, aryl, $C_1$-$C_6$ hydroxyalkyl, NR9R10 and heterocyclyl, and wherein R5 and R6 may also form a 3, 4, 5, or 6, membered ring;

(g) n is 0 to 4;

(h) X is NRB, O or S;

(i) J is N or CR7;

(j) R7 is $C_2$-$C_8$ alkenyl, $C_2$-$C_8$ alkenyloxy, $C_2$-$C_8$ alkenylthio, $C_1$-$C_8$ alkoxy, $C_1$-$C_8$ alkyl, $C_1$-$C_8$ alkylthio, $C_2$-$C_8$ alkynyl, $C_2$-$C_8$ alkynyloxy, $C_2$-$C_8$ alkynylthio, aryl, $C_3$-$C_8$ cycloalkenyl, $C_3$-$C_8$ cycloalkenyloxy, $C_3$-$C_8$ cycloalkenylthio, $C_3$-$C_8$ cycloalkyl, $C_3$-$C_8$ cycloalkoxy, $C_3$-$C_8$ cycloalkylthio, heterocyclyl, or $C_0$-$C_8$ alkyl-C(=O)OR8, wherein each of which may be independently substituted with one or more of the following substituents, F, Cl, Br, I, CN, $NO_2$, $C_1$-$C_6$ alkyl, $C_2$-$C_6$ alkenyl, $C_2$-$C_6$ alkynyl, $C_1$-$C_6$ alkoxy, $C_1$-$C_6$ haloalkyl, $C_1$-$C_6$ haloalkoxy, $C_1$-$C_6$ haloalkylthio, $S(=O)_{n1}C_1$-$C_6$ alkyl (where n1=0-2), $S(=O)_{n1}C_1$-$C_6$ haloalkyl (where n1=0-2), $OSO_2C_1$-$C_6$ haloalkyl, C(=O)O$C_1$-$C_6$ alkyl, C(=O)$C_1$-$C_6$ alkyl, C(=O)$C_1$-$C_6$ haloalkyl, aryl, $C_1$-$C_6$ hydroxyalkyl, NR9R10 and heterocyclyl;

(k) R8 is $C_2$-$C_8$ alkenyl, $C_2$-$C_8$ alkenyloxy, $C_2$-$C_8$ alkenylthio, $C_1$-$C_8$ alkoxy, $C_1$-$C_8$ alkyl, $C_1$-$C_8$ alkylthio, $C_2$-$C_8$ alkynyl, $C_2$-$C_8$ alkynyloxy, $C_2$-$C_8$ alkynylthio, aryl, $C_3$-$C_8$ cycloalkenyl, $C_3$-$C_8$ cycloalkenyloxy, $C_3$-$C_8$ cycloalkenylthio, $C_3$-$C_8$ cycloalkyl, $C_3$-$C_8$ cycloalkoxy, $C_3$-$C_8$ cycloalkylthio, or heterocyclyl, wherein each of which may be independently substituted with one or more of the following substituents, F, Cl, Br, I, CN, $NO_2$, $C_1$-$C_6$ alkyl, $C_2$-$C_6$ alkenyl, $C_2$-$C_6$ alkynyl, $C_1$-$C_6$ alkoxy, $C_1$-$C_6$ haloalkyl, $C_1$-$C_6$ haloalkoxy, $C_1$-$C_6$ haloalkylthio, $S(=O)_{n1}C_1$-$C_6$ alkyl (where n1=0-2), $S(=O)_{n1}C_1$-$C_6$ haloalkyl (where n1=0-2), $OSO_2C_1$-$C_6$ haloalkyl, C(=O)O$C_1$-$C_6$ alkyl, C(=O)$C_1$-$C_6$ alkyl, C(=O)$C_1$-$C_6$ haloalkyl, aryl, $C_1$-$C_6$ hydroxyalkyl, and heterocyclyl;

(l) R9 is $C_2$-$C_8$ alkenyl, $C_2$-$C_8$ alkenyloxy, $C_2$-$C_8$ alkenylthio, $C_1$-$C_8$ alkoxy, $C_1$-$C_8$ alkyl, $C_1$-$C_8$ alkylthio, $C_2$-$C_8$ alkynyl, $C_2$-$C_8$ alkynyloxy, $C_2$-$C_8$ alkynylthio, aryl, $C_3$-$C_8$ cycloalkenyl, $C_3$-$C_8$ cycloalkenyloxy, $C_3$-$C_8$ cycloalkenylthio, $C_3$-$C_8$ cycloalkyl, $C_3$-$C_8$ cycloalkoxy, $C_3$-$C_8$ cycloalkylthio, or heterocyclyl, wherein each of which may be independently substituted with one or more of the following substituents, F, Cl, Br, I, CN, $NO_2$, $C_1$-$C_6$ alkyl, $C_2$-$C_6$ alkenyl, $C_2$-$C_6$ alkynyl, $C_1$-$C_6$ alkoxy, $C_1$-$C_6$ haloalkyl, $C_1$-$C_6$ haloalkoxy, $C_1$-$C_6$ haloalkylthio, $S(=O)_{n1}C_1$-$C_6$ alkyl (where n1=0-2), $S(=O)_{n1}C_1$-$C_6$ haloalkyl (where n1=0-2), $OSO_2C_1$-$C_6$ haloalkyl, C(=O)O$C_1$-$C_6$ alkyl, C(=O)$C_1$-$C_6$ alkyl, C(=O)$C_1$-$C_6$ haloalkyl, aryl, $C_1$-$C_6$ hydroxyalkyl, and heterocyclyl, and wherein R9 and R10 may also form a 4, 5, or 6 membered ring; and (m) R10 is $C_2$-$C_8$ alkenyl, $C_2$-$C_8$ alkenyloxy, $C_2$-$C_8$ alkenylthio, $C_1$-$C_8$ alkoxy, $C_1$-$C_8$ alkyl, $C_1$-$C_8$ alkylthio, $C_2$-$C_8$ alkynyl, $C_2$-$C_8$ alkynyloxy, $C_2$-$C_8$ alkynylthio, aryl, $C_3$-$C_8$ cycloalkenyl, $C_3$-$C_8$ cycloalkenyloxy, $C_3$-$C_8$ cycloalkenylthio, $C_3$-$C_8$ cycloalkyl, $C_3$-$C_8$ cycloalkoxy, $C_3$-$C_8$ cycloalkylthio, or heterocyclyl, wherein each of which may be independently substituted with one or more of the following substituents, F, Cl, Br, I, CN, $NO_2$, $C_1$-$C_6$ alkyl, $C_2$-$C_6$ alkenyl, $C_2$-$C_6$ alkynyl, $C_1$-$C_6$ alkoxy, $C_1$-$C_6$ haloalkyl, $C_1$-$C_6$ haloalkoxy, $C_1$-$C_6$ haloalkylthio, $S(=O)_{n1}C_1$-$C_6$ alkyl (where n1=0-2), $S(=O)_{n1}C_1$-$C_6$ haloalkyl (where n1=0-2), $OSO_2C_1$-$C_6$ haloalkyl, C(=O)O$C_1$-$C_6$ alkyl, C(=O)$C_1$-$C_6$ alkyl, C(=O)$C_1$-$C_6$ haloalkyl, aryl, $C_1$-$C_6$ hydroxyalkyl, and heterocyclyl, and wherein R9 and R10 may also form a 4, 5, or 6 membered ring.

In another embodiment of the invention, R1 is a $C_1$-$C_8$ alkoxy, $C_1$-$C_8$ alkyl, aryl, or heterocyclyl, wherein each of which may be independently substituted with one or more of the following substituents F, Cl, Br, I, CN, $NO_2$, $C_1$-$C_6$ alkyl, $C_2$-$C_6$ alkenyl, $C_2$-$C_6$ alkynyl, $C_1$-$C_6$ alkoxy, $C_1$-$C_6$ haloalkyl, $C_1$-$C_6$ haloalkoxy, $S(=O)_{n1}C_1$-$C_6$ alkyl (where n1=0-2), S(=O)$_{n1}$C$_1$-C$_6$ haloalkyl (where n1=0-2), OSO$_2$C$_1$-C$_6$ haloalkyl, C(=O)OC$_1$-C$_6$ alkyl, C(=O)C$_1$-C$_6$ alkyl, C(=O) C$_1$-C$_6$ haloalkyl, aryl, C$_1$-C$_6$ hydroxyalkyl, NR9R10 and heterocyclyl.

In another embodiment of the invention, R1 is a heterocyclyl, which may be independently substituted with one or more of the following substituents F, Cl, Br, I, CN, NO$_2$, C$_1$-C$_6$ alkyl, C$_2$-C$_6$ alkenyl, C$_2$-C$_6$ alkynyl, C$_1$-C$_6$ alkoxy, C$_1$-C$_6$ haloalkyl, C$_1$-C$_6$ haloalkoxy, S(=O)$_{n1}$C$_1$-C$_6$ alkyl (where n1=0-2), S(=O)$_{n1}$C$_1$-C$_6$ haloalkyl (where n1=0-2), OSO$_2$C$_1$-C$_6$ haloalkyl, C(=O)OC$_1$-C$_6$ alkyl, C(=O)C$_1$-C$_6$ alkyl, C(=O)C$_1$-C$_6$ haloalkyl, aryl, C$_1$-C$_6$ hydroxyalkyl, NR9R10 and heterocyclyl.

In another embodiment of the invention, R1 is benzofuranyl, benzoisothiazolyl, benzoisoxazolyl, benzoxazolyl, benzothienyl, benzothiazolyl cinnolinyl, furanyl, indazolyl, indolyl, imidazolyl, isoindolyl, isoquinolinyl, isothiazolyl, isoxazolyl, 1,3,4-oxadiazolyl, oxazolinyl, oxazolyl, phthalazinyl, pyrazinyl, pyrazolinyl, pyrazolyl, pyridazinyl, pyridyl, pyrimidinyl, pyrrolyl, quinazolinyl, quinolinyl, quinoxalinyl, 1,2,3,4-tetrazolyl, thiazolinyl, thiazolyl, thienyl, 1,2,3-triazinyl, 1,2,4-triazinyl, 1,3,5-triazinyl, 1,2,3-triazolyl, and 1,2,4-triazolyl, which may be independently substituted with one or more of the following substituents F, Cl, Br, I, CN, NO$_2$, C$_1$-C$_6$ alkyl, C$_2$-C$_6$ alkenyl, C$_2$-C$_6$ alkynyl, C$_1$-C$_6$ alkoxy, C$_1$-C$_6$ haloalkyl, C$_1$-C$_6$ haloalkoxy, S(=O)$_{n1}$C$_1$-C$_6$ alkyl (where n1=0-2), S(=O)$_{n1}$C$_1$-C$_6$ haloalkyl (where n1=0-2), OSO$_2$C$_1$-C$_6$ haloalkyl, C(=O)OC$_1$-C$_6$ alkyl, C(=O)C$_1$-C$_6$ alkyl, C(=O)C$_1$-C$_6$ haloalkyl, aryl, C$_1$-C$_6$ hydroxyalkyl, NR9R10 and heterocyclyl.

In another embodiment of the invention, R1 is pyridyl, which may be independently substituted with one or more of the following substituents F, Cl, Br, I, CN, NO$_2$, C$_1$-C$_6$ alkyl, C$_2$-C$_6$ alkenyl, C$_2$-C$_6$ alkynyl, C$_1$-C$_6$ alkoxy, C$_1$-C$_6$ haloalkyl, C$_1$-C$_6$ haloalkoxy, S(=O)$_{n1}$C$_1$-C$_6$ alkyl (where n1=0-2), S(=O)$_{n1}$C$_1$-C$_6$ haloalkyl (where n1=0-2), OSO$_2$C$_1$-C$_6$ haloalkyl, C(=O)OC$_1$-C$_6$ alkyl, C(=O)C$_1$-C$_6$ alkyl, C(=O) C$_1$-C$_6$ haloalkyl, aryl, C$_1$-C$_6$ hydroxyalkyl, NR9R10 and heterocyclyl.

In another embodiment of the invention, R1 is pyridyl, which may be independently substituted with one or more C$_1$-C$_6$ haloalkyls.

In another embodiment of the invention, R1 is a pyridyl substituted with CF$_3$.

In another embodiment of the invention, R2 is C$_1$-C$_8$ alkyl, which may be independently substituted with one or more of the following substituents F, Cl, Br, I, CN, NO$_2$, C$_1$-C$_6$ alkyl, C$_2$-C$_6$ alkenyl, C$_2$-C$_6$ alkynyl, C$_1$-C$_6$ alkoxy, C$_1$-C$_6$ haloalkyl, C$_1$-C$_6$ haloalkoxy, S(=O)$_{n1}$C$_1$-C$_6$ alkyl (where n1=0-2), S(=O)$_{n1}$C$_1$-C$_6$ haloalkyl (where n1=0-2), OSO$_2$C$_1$-C$_6$ haloalkyl, C(=O)OC$_1$-C$_6$ alkyl, C(=O)C$_1$-C$_6$ alkyl, C(=O) C$_1$-C$_6$ haloalkyl, aryl, C$_1$-C$_6$ hydroxyalkyl, NR9R10 and heterocyclyl.

In another embodiment of the invention, R3 is a C$_1$-C$_8$ alkoxy, C$_1$-C$_8$ alkyl, aryl, C$_3$-C$_8$ cycloalkenyl, C$_3$-C$_8$ cycloalkenyloxy, C$_3$-C$_8$ cycloalkenylthio, C$_3$-C$_8$ cycloalkyl, C$_3$-C$_8$ cycloalkoxy, C$_3$-C$_8$ cycloalkylthio, H, heterocyclyl, or C$_0$-C$_8$ alkyl-C(=O)OR8, wherein each of which may be independently substituted (except for H) with one or more of the following substituents F, Cl, Br, I, CN, NO$_2$, C$_1$-C$_6$ alkyl, C$_2$-C$_6$ alkenyl, C$_2$-C$_6$ alkynyl, C$_1$-C$_6$ alkoxy, C$_1$-C$_6$ haloalkyl, C$_1$-C$_6$ haloalkoxy, S(=O)$_{n1}$C$_1$-C$_6$ alkyl (where n1=0-2), S(=O)$_{n1}$C$_1$-C$_6$ haloalkyl (where n1=0-2), OSO$_2$C$_1$-C$_6$ haloalkyl, C(=O)OC$_1$-C$_6$ alkyl, C(=O)C$_1$-C$_6$ alkyl, C(=O) C$_1$-C$_6$ haloalkyl, aryl, C$_1$-C$_6$ hydroxyalkyl, NR9R10 and heterocyclyl, also R3 and R4 may form a 4, 5, or 6 membered ring.

In another embodiment of the invention, R4 is a C$_1$-C$_8$ alkoxy, C$_1$-C$_8$ alkyl, aryl, C$_3$-C$_8$ cycloalkenyl, C$_3$-C$_8$ cycloalkenyloxy, C$_3$-C$_8$ cycloalkenylthio, C$_3$-C$_8$ cycloalkyl, C$_3$-C$_8$ cycloalkoxy, C$_3$-C$_8$ cycloalkylthio, H, heterocyclyl, or C$_0$-C$_8$ alkyl-C(=O)OR8, wherein each of which may be independently substituted (except for H) with one or more of the following substituents F, Cl, Br, I, CN, NO$_2$, C$_1$-C$_6$ alkyl, C$_2$-C$_6$ alkenyl, C$_2$-C$_6$ alkynyl, C$_1$-C$_6$ alkoxy, C$_1$-C$_6$ haloalkyl, C$_1$-C$_6$ haloalkoxy, S(=O)$_{n1}$C$_1$-C$_6$ alkyl (where n1=0-2), S(=O)$_{n1}$C$_1$-C$_6$ haloalkyl (where n1=0-2), OSO$_2$C$_1$-C$_6$ haloalkyl, C(=O)OC$_1$-C$_6$ alkyl, C(=O)C$_1$-C$_6$ alkyl, C(=O) C$_1$-C$_6$ haloalkyl, aryl, C$_1$-C$_6$ hydroxyalkyl, NR9R10 and heterocyclyl, also R3 and R4 may form a 4, 5, or 6 membered ring.

In another embodiment of the invention, X is S.

In another embodiment of the invention, R5 and R6 are independently selected from H, methyl, ethyl, F, Cl, and Br.

In another embodiment of the invention, n is 1, and R5 is CH$_3$ and R6 is H.

While these embodiments have been expressed, other embodiments and combinations of these expressed embodiments and other embodiments, are possible.

Throughout this document, all temperatures are given in degrees Celsius, and all percentages are weight percentages unless otherwise stated.

The compounds of this invention can be made in a variety of ways. One general way is to start with a molecule formed as in WO 2007/095229 A2 entitled "Insecticidal N-substituted (6-haloalkylpyridin-3-yl)alkyl sulfoximines" published 23 Aug. 2007 and to follow the general methods illustrated in Schemes A-F below.

The compounds of formula (I), wherein R1, R2, R4, R5, R6, and n are as previously defined and wherein X=S, J=N, and R3 is H, can be prepared by the methods illustrated in Scheme A.

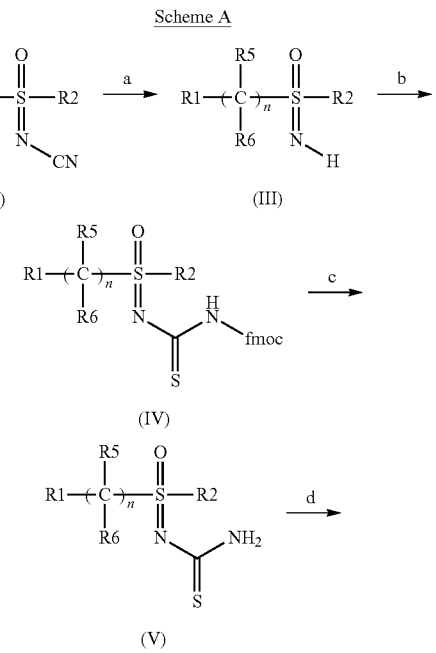

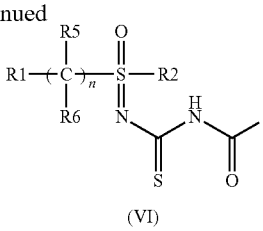

(VI)

In step a of Scheme A, compounds of formula (II) can be converted to compounds of formula (III) as known in the art (for example see *Org. Lett.* 2007, 9, 3809) when treated with trifluoroacetic anhydride in a polar aprotic solvent such as dichloromethane ($CH_2Cl_2$) followed by a base such as potassium carbonate in a polar protic solvent such as methanol. The reactions are typically conducted at temperatures ranging from −20° C. to 50° C. and are generally complete in one to 18 hours. The compounds can be recovered and purified by conventional methods. Cyano sulfoximine (II) (also known as "sulfoxaflor") can be prepared by methods known in the art (for example see WO 2007095229 A2). In step b of Scheme A, compounds of formula (III) are allowed to react with 9-fluorenylmethoxycarbonyl (Fmoc) isothiocyanate in a mixture of polar aprotic solvents such as tetrahydrofuran (THF) and N,N-dimethylformamide (DMF) to give compounds of formula (IV) as known in the art (for example see *Heterocycles* 1998, 49, 181). The reactions are typically conducted at temperatures ranging from 0° C. to 100° C. and are generally complete in one to 18 hours. The compounds can be recovered and purified by conventional methods. In step c of Scheme A, compounds of formula (IV) can be treated with a base such as piperidine, in a polar aprotic solvent such as DMF to give compounds of formula (V). The reactions are typically conducted at temperatures ranging from −20° C. to 50° C. and are generally complete in one to 18 hours. The compounds can be recovered and purified by conventional methods. In step d of Scheme A, compounds of formula (V) can be allowed to react with an acid chloride such as acetyl chloride in an organic solvent such as acetone and in the presence of a base such as triethylamine to give compounds of formula (VI) as known in the art (for example see *Inorg. Chem. Commun.* 2000, 3, 630). The reactions are typically conducted at temperatures ranging from 0° C. to 100° C. and are generally complete in one to 18 hours. The compounds can be recovered and purified by conventional methods.

The compounds of formula (I), wherein R1, R2, R4, R5, R6, and n are as previously defined and wherein X=S, J=N, and R3 is H, can be prepared by the methods illustrated in Scheme B.

Scheme B

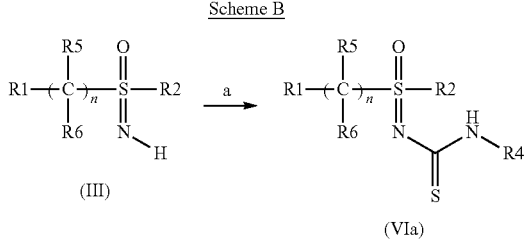

In step a of Scheme B, compounds of formula (III) are treated with an isothiocyanate such as ethyl isothiocyanate in a mixture of polar aprotic solvents such as THF and DMF to give compounds of formula (IVa) as described in Scheme A. The reactions are typically conducted at temperatures ranging from 0° C. to 100° C. and are generally complete in one to 18 hours. The compounds can be recovered and purified by conventional methods.

The compounds of formula (I), wherein R1, R2, R3, R4, R5, R6, and n are as previously defined and wherein X=S and J=N, can be prepared by the methods illustrated in Scheme C.

Scheme C

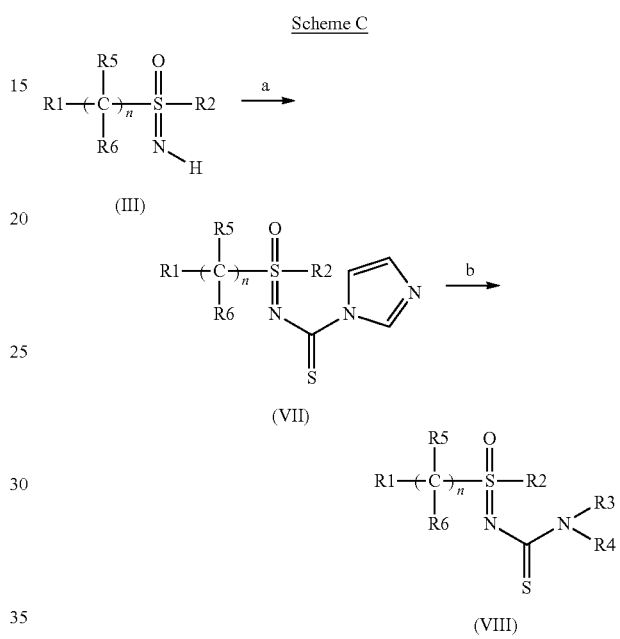

In step a of Scheme C, compounds of formula (III) can be reacted with thiocarbonyl diimidazole in an organic solvent such as acetonitrile to give compounds of formula (VII) as known in the art (for example see *Letters in Drug Design and Discovery* 2007, 4, 318). The reactions are typically conducted at temperatures ranging from 0° C. to 100° C. and are generally complete in one to 18 hours. The compounds can be recovered and purified by conventional methods. In step b of Scheme C, compounds of formula (VII) can be treated with an amine such as dimethylamine in an organic solvent such as acetonitrile to give compounds of formula (VIII). The reactions are typically conducted at temperatures ranging from 0° C. to 100° C. and are generally complete in one to 18 hours. The compounds can be recovered and purified by conventional methods.

The compounds of formula (I), wherein R1, R2, R5, R6, R7 and n are as previously defined and wherein X=O or S, can be prepared by the methods illustrated in Scheme D.

Scheme D

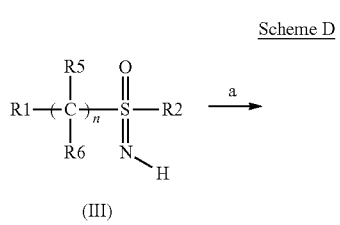

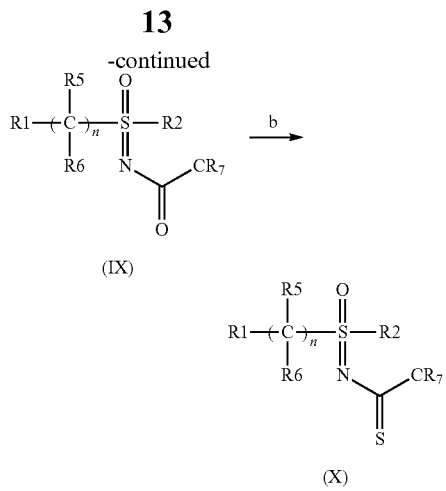

(IX)

(X)

In step a of Scheme D, compounds of formula (III) can be treated with an anhydride such as acetic anhydride in the presence of an organic solvent such as pyridine to give compounds of formula (IX) as known in the art (for example see *Heterocycles* 1998, 49, 181). The reactions are typically conducted at temperatures ranging from 0° C. to 100° C. and are generally complete in one to 18 hours. The compounds can be recovered and purified by conventional methods. In step b of Scheme D, compounds of formula (IX) can be thionated by treatment with reagents such as Lawesson's reagent in organic solvents such as 1,4-dioxane to give compounds of formula (X). The reactions are typically conducted at temperatures ranging from 0° C. to 100° C. and are generally complete in one to 18 hours. The compounds can be recovered and purified by conventional methods.

The compounds of formula (I), wherein R1, R2, R4, R5, R6, and n are as previously defined and wherein X=O, J=N, and R3 is H, can be prepared by the methods illustrated in Scheme E.

Scheme E

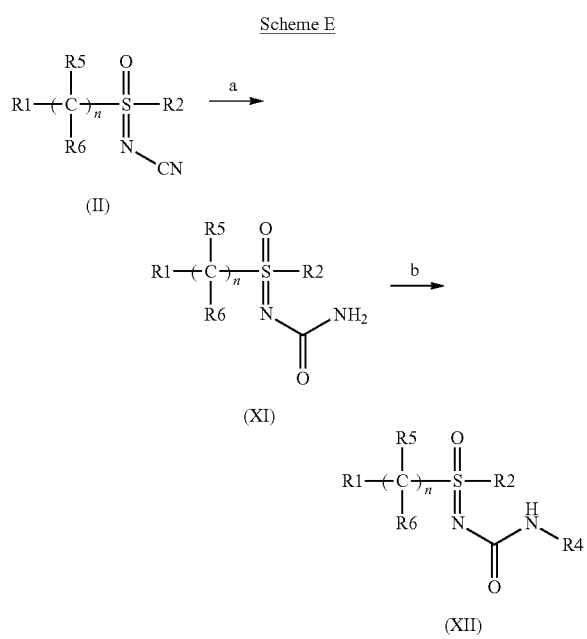

In step a of Scheme E, compounds of formula (II) can be hydrolyzed in the presence of a strong acid such as concentrated sulfuric acid in an organic solvent such as acetonitrile to give compounds of formula (XI). The reactions are typically conducted at temperatures ranging from 0° C. to 100° C. and are generally complete in one to 18 hours. The compounds can be recovered and purified by conventional methods. In step b of Scheme E, compounds of formula (XI) can be treated with an acid chloride such as acetyl chloride in a nonpolar organic solvent such as anhydrous benzene to give compounds of formula (XII). The reactions are typically conducted at temperatures ranging from 0° C. to 150° C. and are generally complete in one to 18 hours. The compounds can be recovered and purified by conventional methods.

The compounds of formula (I), wherein R1, R2, R5, R6, R8, and n are as previously defined and wherein X=NR8 and J=N, can be prepared by the methods illustrated in Scheme F.

Scheme F

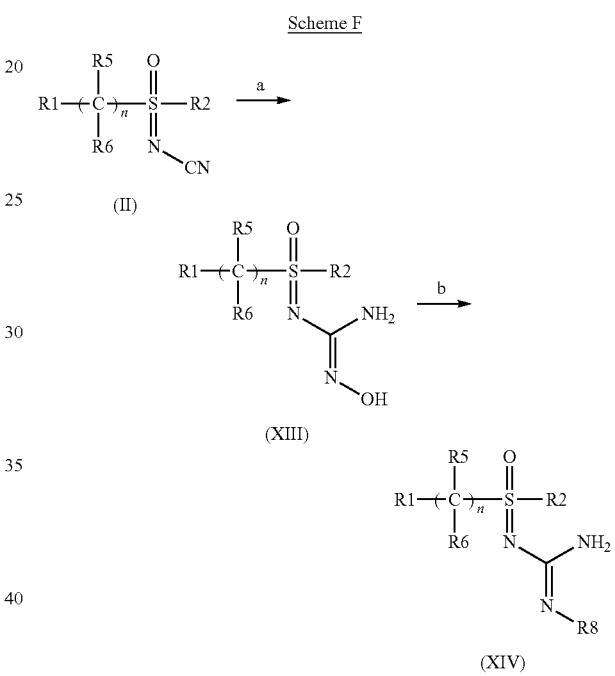

In step a of Scheme F, compounds of formula (II) can be allowed to react with a nucleophile such as hydroxylamine hydrochloride in the presence of a base such as sodium carbonate in a mixed polar protic solvent system such as ethanol and water to give compounds of formula (XIII) as known in the art (for example see *J. Chem. Soc., Perkin Trans.* 1 2001, 1321). The reactions are typically conducted at temperatures ranging from 0° C. to 150° C. and are generally complete in one to 18 hours. The compounds can be recovered and purified by conventional methods. Similarly, compounds of formula (IX) in Scheme D can be converted to the corresponding oximes under these conditions. In step b of Scheme F, compounds of formula (XIII) can be allowed to react with bases such as sodium hydride or potassium carbonate in polar aprotic solvents such as THF or acetonitrile in the presence of an alkyl halide such as methyl iodide to give compounds of formula (XIV). The reactions are typically conducted at temperatures ranging from 0° C. to 150° C. and are generally complete in one to 18 hours. The compounds can be recovered and purified by conventional methods.

The compounds of formula (I), wherein R1, R2, R5, R6, and n are as previously defined and wherein X=NH and J=N, can be prepared by the methods illustrated in Scheme G.

Scheme G

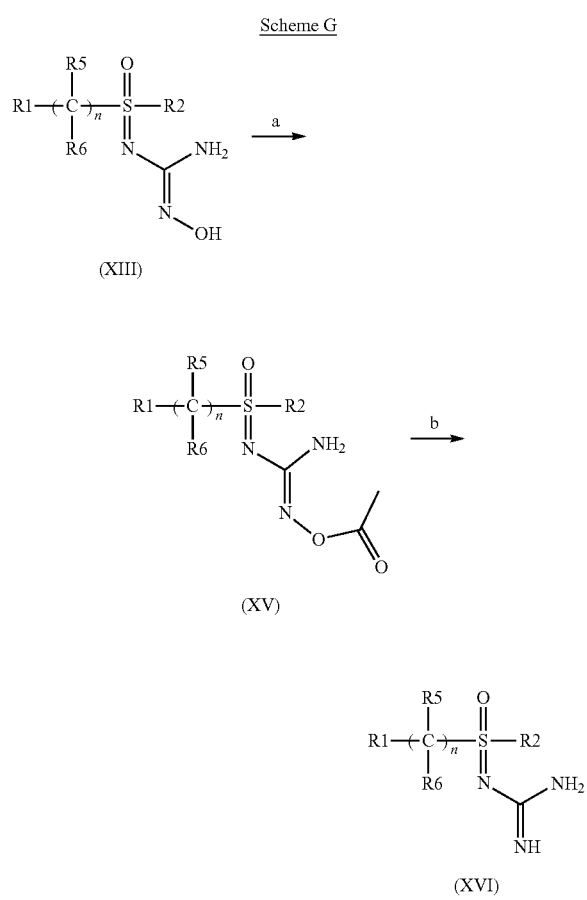

In step a of Scheme G, compounds of formula (XIII) can be allowed to react with an anhydride such as acetic anhydride in the presence of an acid such as glacial acetic acid to give compounds of formula (XV). The reactions are typically conducted at temperatures ranging from 0° C. to 150° C. and are generally complete in one to 18 hours. The compounds can be recovered and purified by conventional methods. In step b of Scheme G, compounds of formula (XV) can be hydrogenated in the presence of a catalyst such as palladium on carbon in a polar protic solvent such as glacial acetic acid and an anhydride such as acetic anhydride to give compounds of formula (XVI) as known in the art (for example see *Synth. Commun.* 2007, 37, 4157). The reactions are typically conducted at temperatures ranging from 0° C. to 150° C. and are generally complete in one to 18 hours. The compounds can be recovered and purified by conventional methods.

EXAMPLES

The examples are for illustration purposes and are not to be construed as limiting the invention disclosed in this document to only the embodiments disclosed in these examples.

List of Abbreviations tetrahydrofuran THF

N,N-dimethylformamide DMF electrospray ionization mass spectrometry ESIMS relative humidity RH

Example 1

Preparation of N-[(4-chlorophenyl)(methyl)oxido-$\lambda^4$-sulfanylidene]-N'-[4-(trifluoromethyl)phenyl]urea (1)

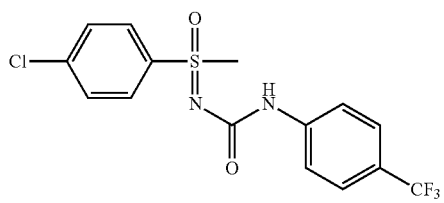 [SMILES: CS(=O)(=NC(=O)Nc1ccc(C(F)(F)F)cc1)c1ccc(Cl)cc1]

1-Chloro-4-(methylsulfonimidoyl)benzene (0.37 g, 1.9 mmol) was dissolved in $CH_2Cl_2$ (16 mL) at room temperature. To this solution was added 60% sodium hydride in mineral oil (68 mg, 1.7 mmol) which caused bubbling. When the bubbling subsided, 4-trifluoromethyl phenyl isocyanate (0.42 g, 1.9 mmol) was added, and the mixture was allowed to stir for 2 h at room temperature. The reaction was then quenched with brine (10 mL) and the mixture was extracted with ethyl acetate (3×10 mL). The organic extracts were combined, dried ($MgSO_4$), filtered, and concentrated in vacuo to furnish N-[4-chlorophenyl)(methyl)oxido-$\lambda^4$-sulfanylidene]-N'-[4-(trifluoromethyl)phenyl]urea (1) as a white solid (0.466 g, 76%): mp 131-134° C.; $^1$H NMR (300 MHz, $CDCl_3$) δ 7.95 (d, J=8.7 Hz, 2H), 7.59 (d, J=8.4 Hz, 2H), 7.52 (s, 4H), 3.39 (s, 3H); ESIMS m/z 376 ([M]$^+$).

Example 2

Preparation of N-[(4-chlorophenyl)(methyl)oxido-$\lambda^4$-sulfanylidene]-N'-[4-chloro-3-(trifluoromethyl)phenyl]urea (2)

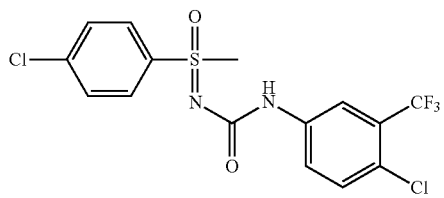 [SMILES: CS(=O)(=NC(=O)Nc1ccc(Cl)c(C(F)(F)F)c1)c1ccc(Cl)cc1]

N-[(4-Chlorophenyl)(methyl)oxido-$\lambda^4$-sulfanylidene]-N'-[4-chloro-3-(trifluoromethyl)phenyl]urea (2) was synthesized from 1-chloro-4-(methylsulfonimidoyl)benzene according to the procedure described in Example 1. The compound was isolated as a colorless oil (0.319 g, 54%): $^1$H NMR (300 MHz, $CDCl_3$) δ 7.95 (d, J=9.0 Hz, 2H), 7.77 (br s, 1H), 7.59 (d, J=8.7 Hz, 2H), 7.54 (br s, 1H), 7.36 (d, J=8.7 Hz, 1H), 3.36 (s, 3H); ESIMS m/z 410 ([M]+).

Example 3

Preparation of N-(chloroacetyl)-N'-(methyl(oxido)-{1-[6-(trifluoromethyl)pyridin-3-yl]ethyl}-λ⁴-sulfanylidene)urea (3)

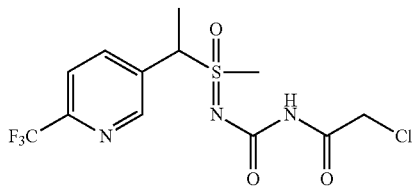 [SMILES: CC(c1ccc(C(F)(F)F)nc1)S(C)(=O)=NC(=O)NC(=O)CCl]

Step A. Preparation of N-(methyl(oxido){1-[6-(trifluoromethyl)pyridin-3-yl]ethyl}-λ⁴-sulfanylidene)urea

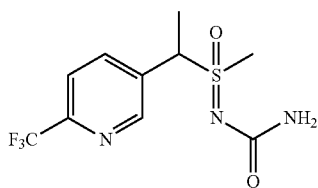 [SMILES: CC(c1ccc(C(F)(F)F)nc1)S(C)(=O)=NC(N)=O]

To a vigorously stirred solution of methyl(oxido){1-[6-(trifluoromethyl)pyridin-3-yl]ethyl}-λ⁴-sulfanylidenecyanamide (100 g, 0.36 mol) in acetonitrile (500 mL) was added dropwise concentrated sulfuric acid (25 mL) at a rate to maintain the temperature below 40° C. (A little external cooling was required initially.) Upon completion of the addition, the reaction mixture (now cloudy, with some separated oil) was stirred for another hour at ambient temperature until starting material was consumed. The mixture was then cooled to 5° C., and 50% NaOH was added dropwise (exothermic) until the solution was neutral by pH paper. The resulting solid was filtered, and the filtrate was transferred to a separatory funnel. The layers were separated, and the organic layer was washed with brine, dried (MgSO₄), filtered, and concentrated in vacuo to afford N-(methyl(oxido){1-[6-(trifluoromethyl)pyridin-3-yl]ethyl}-λ⁴-sulfanylidene)urea as a white solid (99.4 g, 93%): ESIMS m/z 296 ([M+H]+).

Step B. Preparation of N-(chloroacetyl)-N'-(methyl(oxido){1-[6-(trifluoromethyl)pyridin-3-yl]ethyl}-λ⁴-sulfanylidene)urea (3)

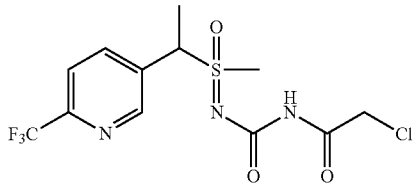 [SMILES: CC(c1ccc(C(F)(F)F)nc1)S(C)(=O)=NC(=O)NC(=O)CCl]

A suspension of N-(methyl(oxido){1-[6-(trifluoromethyl)pyridin-3-yl]ethyl}-λ⁴-sulfanylidene)urea (2.0 g, 6.78 mmol) and chloroacetyl chloride (0.92 g, 8.14 mmol) in anhydrous benzene (50 mL) was heated to reflux under N₂ for 2 h. The reaction mixture was cooled externally with an ice-water bath and hexane (100 mL) was added to precipitate the product. The reaction mixture was stirred for an additional 15 min, and the solid was collected via suction filtration and rinsed with ether to furnish N-(chloroacetyl)-N-(methyl(oxido) {1-[6-(trifluoromethyl)pyridin-3-yl]ethyl}-λ⁴-sulfanylidene)urea (3) as a white solid (1.37 g, 54%): mp 178-179° C.; ¹H NMR (300 MHz, DMSO-d₆) δ (1:1 mixture of two diastereomers) 10.4 (s, NH), 8.9 (m, 1H), 8.3 (m, 1H), 8.0 (m, 1H), 5.1 (q, 1H), 4.5 (s, 2H), 3.4 (s, 3H), 1.8 (d, 3H); ESIMS m/z 372 ([M+H]+).

Example 4

Preparation of N-(methyl(oxido){1-[6-(trifluoromethyl)pyridin-3-yl]ethyl}-λ⁴-sulfanylidene)-N-pyridin-3-ylthiourea (4)

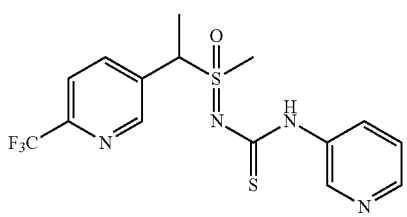 [SMILES: CC(c1ccc(C(F)(F)F)nc1)S(C)(=O)=NC(=S)Nc1cccnc1]

Step A. Preparation of 5-[1-(methylsulfonimidoyl)ethyl]-2-(trifluoromethyl)pyridine

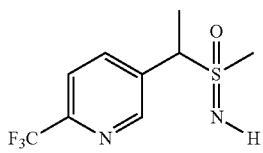

To a stirred solution of methyl(oxido){1-[6-(trifluoromethyl)pyridin-3-yl]ethyl}-λ⁴-sulfanylidenecyanamide (5 g, 18 mmol) in CH₂Cl₂ (300 mL) at 0° C. was added trifluoroacetic anhydride (7.5 mL, 54 mmol). The mixture was allowed to react at 25° C. until the starting material was fully consumed. The reaction mixture was concentrated in vacuo, dissolved in methanol (125 mL) and treated with potassium carbonate (12.5 g, 90 mmol). The mixture was allowed to stir at 25° C. until the starting material was consumed. The crude reaction mixture was filtered, concentrated and purified by chromatography (acetone-hexanes) to furnish 5-[1-(methylsulfonimidoyl)ethyl]-2-(trifluoromethyl)pyridine as a white solid (3.5 g, 77%): ESIMS m/z 253 ([M+H]$^+$).

Step B. Preparation of N-(methyl(oxido){1-[6-(trifluoromethyl)pyridin-3-yl]ethyl}-λ$^4$-sulfanylidene)-N'-pyridin-3-ylthiourea (4)

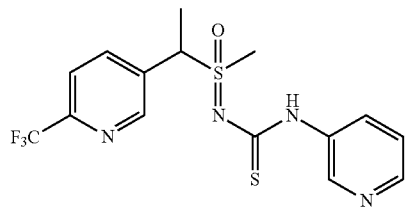 [SMILES: CC(c1ccc(C(F)(F)F)nc1)S(C)(=O)=NC(=S)Nc1cccnc1]

In a 50 mL round bottom flask charged with a magnetic stirbar, 5-[1-(methylsulfonimidoyl)-ethyl]-2-(trifluoromethyl)pyridine (0.200 g, 0.793 mmol) was dissolved in THF (4.17 mL) and DMF (0.83 mL) at 25° C. Next, 3-isothiocyanatopyridine (0.132 mL, 1.11 mmol) was added to the reaction flask. Following addition, the reaction was warmed to 80° C. for 12 h. Upon completion of reaction, the mixture was diluted with ethyl acetate and brine. The layers were separated, and the aqueous layer was extracted with ethyl acetate. The organic extracts were combined and washed with brine, dried (Na$_2$SO$_4$), filtered, and concentrated in vacuo. The crude material was purified using reverse-phase HPLC eluting with acetonitrile-water mixtures to furnish N-(methyl (oxido){1-[6-(trifluoromethyl)pyridin-3-yl]ethyl}-λ$^4$-sulfanylidene)-N-pyridin-3-ylthiourea (4) as a white solid (0.191 g, 62%): mp 92-94° C.; $^1$H NMR (400 MHz, CDCl$_3$) δ (mixture of diastereomers) 8.82 & 8.76 (s, 1H), 8.5 (m, 2H), 8.07 (m, 2H), 7.74 (m, 1H), 7.30 (m, 1H), 5.89 & 5.61 (m, 1H), 3.55 & 3.35 (s, 3H), 1.94 & 1.85 (m, 3H); ESIMS m/z 389 ([M+H]$^+$).

TABLE 1

Insecticidal Compounds

| Cmpd # | Structure | Route | Characterization |
|---|---|---|---|
| 5 | 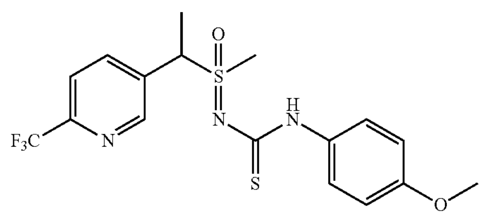 [SMILES: COc1ccc(NC(=S)N=S(C)(=O)C(C)c2ccc(C(F)(F)F)nc2)cc1] | A | white solid; mp 167-169° C.; ESIMS m/z 418 ([M + H]$^+$) |
| 6 | 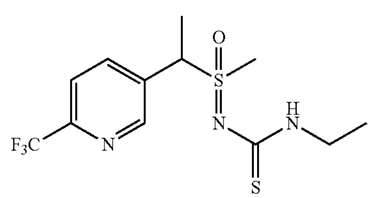 [SMILES: CCNC(=S)N=S(C)(=O)C(C)c1ccc(C(F)(F)F)nc1] | A | light yellow foam; ESIMS m/z 340 ([M + H]$^+$) |
| 7 | 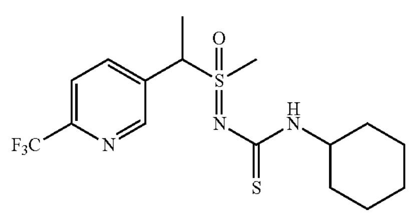 [SMILES: CC(c1ccc(C(F)(F)F)nc1)S(C)(=O)=NC(=S)NC1CCCCC1] | A | white solid; mp 170-172° C.; ESIMS m/z 394 ([M + H]$^+$) |
| 8 | 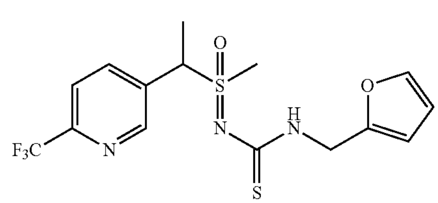 [SMILES: CC(c1ccc(C(F)(F)F)nc1)S(C)(=O)=NC(=S)NCc1ccco1] | A | light brown oil; ESIMS m/z 392 ([M + H]$^+$) |

TABLE 1-continued

Insecticidal Compounds

| Cmpd # | Structure | Route | Characterization |
|---|---|---|---|
| 9 | 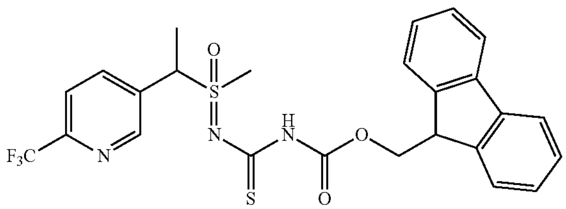 [SMILES: CC(c1ccc(C(F)(F)F)nc1)S(C)(=O)=NC(=S)NC(=O)OCC1c2ccccc2-c2ccccc21] | A | yello solid; mp 105-107° C.; ESIMS m/z 534 ([M + H]$^+$) |
| 10 | 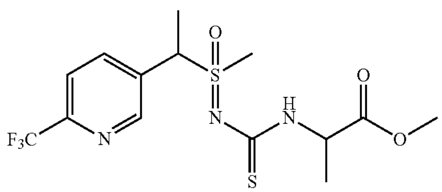 [SMILES: COC(=O)C(C)NC(=S)N=S(C)(=O)C(C)c1ccc(C(F)(F)F)nc1] | A | light brown semi-solid; ESIMS m/z 398 ([M + H]$^+$) |
| 11 | 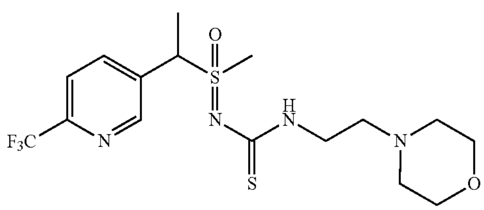 [SMILES: CC(c1ccc(C(F)(F)F)nc1)S(C)(=O)=NC(=S)NCCN1CCOCC1] | A | golden yellow oil; ESIMS m/z 425 ([M + H]$^+$) |
| 12 | 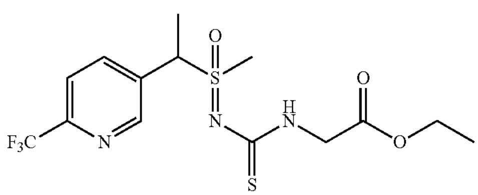 [SMILES: CCOC(=O)CNC(=S)N=S(C)(=O)C(C)c1ccc(C(F)(F)F)nc1] | A | orange semi-solid; ESIMS m/z 398 ([M + H]$^+$) |
| 13 | 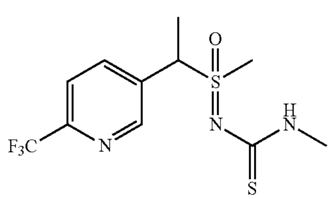 [SMILES: CNC(=S)N=S(C)(=O)C(C)c1ccc(C(F)(F)F)nc1] | A | white semi-solid; ESIMS m/z 326 ([M + H]$^+$) |
| 14 | 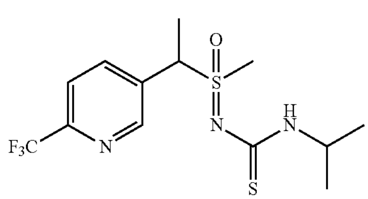 [SMILES: CC(C)NC(=S)N=S(C)(=O)C(C)c1ccc(C(F)(F)F)nc1] | A | white solid; mp 153-155° C.; ESIMS m/z 354 ([M + H]$^+$) |
| 15 | 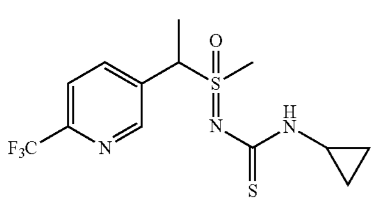 [SMILES: CC(c1ccc(C(F)(F)F)nc1)S(C)(=O)=NC(=S)NC1CC1] | A | off-white solid; mp 154-156° C.; ESIMS m/z 352 ([M + H]$^+$) |

TABLE 1-continued
Insecticidal Compounds
| Cmpd # | Structure | Route | Characterization |
|---|---|---|---|
| 16 | 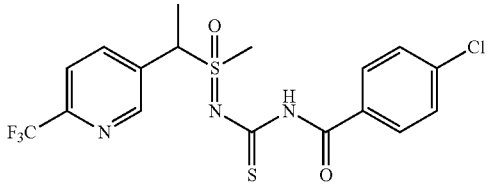 [SMILES: CC(c1ccc(C(F)(F)F)nc1)S(C)(=O)=NC(=S)NC(=O)c1ccc(Cl)cc1] | A | light yellow semi-solid; ESIMS m/z 450 ([M + H]$^+$) |
| 17 | 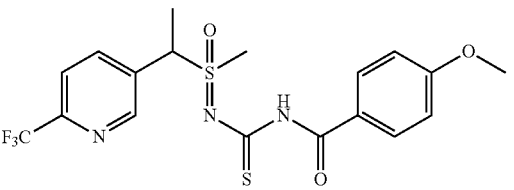 [SMILES: COc1ccc(C(=O)NC(=S)N=S(C)(=O)C(C)c2ccc(C(F)(F)F)nc2)cc1] | A | light yellow semi-solid; ESIMS m/z 446 ([M + H]$^+$) |
| 18 | 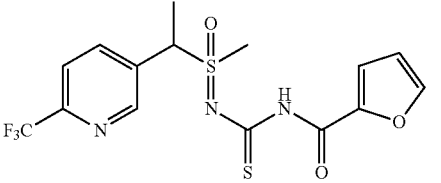 [SMILES: CC(c1ccc(C(F)(F)F)nc1)S(C)(=O)=NC(=S)NC(=O)c1ccco1] | A | light yellow semi-solid; ESIMS m/z 406 ([M + H]$^+$) |
| 19 | 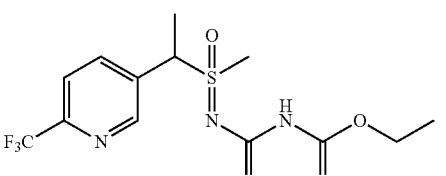 | A | white solid; ESIMS m/z 384 [M + H]$^+$) |
| 20 | 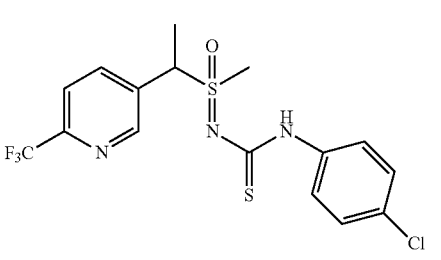 [SMILES: CC(c1ccc(C(F)(F)F)nc1)S(C)(=O)=NC(=S)Nc1ccc(Cl)cc1] | A | white solid; mp 181-183° C.; ESIMS m/z 422 ([M + H]$^+$) |
| 21 | 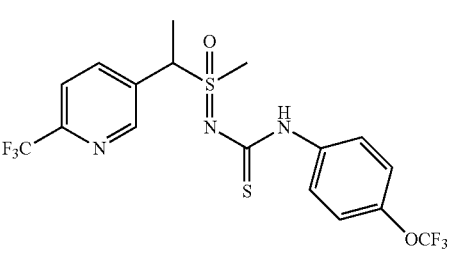 [SMILES: CC(c1ccc(C(F)(F)F)nc1)S(C)(=O)=NC(=S)Nc1ccc(OC(F)(F)F)cc1] | A | off-white solid; mp 149-151° C.; ESIMS m/z 472 ([M + H]$^+$) |
A = Route used for Example 4

Example 5

Preparation of N-(methyl(oxido){1-[6-(trifluoromethyl)pyridin-3-yl]ethyl}-λ⁴-sulfanylidenen)thiourea (22)

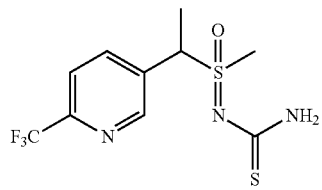 [SMILES: CC(c1ccc(C(F)(F)F)nc1)S(C)(=O)=NC(N)=S]

Compound 9 (0.100 g, 0.187 mmol) was dissolved with stirring in 20% piperidine/DMF (2 mL) at 25° C. Upon completion of the reaction, the mixture was concentrated in vacuo. The crude material was purified using reverse-phase HPLC eluting with acetonitrile-water mixtures to furnish N-(methyl(oxido){1-[6-(trifluoromethyl)pyridin-3-yl]ethyl}-λ⁴-sulfanylidene)thiourea (22) as an off-white solid (0.043 g, 74%): mp 145-147° C.; ¹H NMR (400 MHz, CDCl₃) δ (mixture of diastereomers) 8.86 (s, 1H), 8.10 (m, 1H), 7.76 (m, 1H), 6.09 & 5.94 (m, 1H), 3.52 & 3.24 (s, 3H), 1.93 & 1.83 (d, J=7.3 Hz, 3H); ESIMS m/z 312 ([M+H]⁺).

Example 6

Preparation of N,N-dimethyl-N'-(methyl(oxido){1-[6-(trifluoromethyl)pyridin-3-yl]ethyl}-λ⁴-sulfanylidenen)thiourea (23)

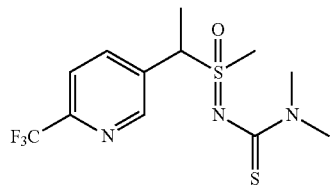 [SMILES: CC(c1ccc(C(F)(F)F)nc1)S(C)(=O)=NC(=S)N(C)C]

Step A. Preparation of N-(methyl(oxido){1-[6-(trifluoromethyl)pyridin-3-yl]ethyl}-λ⁴-sulfanylidene)-1H-imidazole-1-carbothioamide

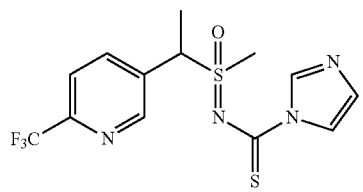 [SMILES: CC(c1ccc(C(F)(F)F)nc1)S(C)(=O)=NC(=S)n1ccnc1]

5-[1-(Methylsulfonimidoyl)ethyl]-2-(trifluoromethyl)pyridine (2.1 g, 8.3 mmol) was dissolved in acetonitrile (17 mL) at room temperature. To this mixture was added thiocarbonyl diimidazole (3 g, 17 mmol) in a single portion. The mixture was heated to 80° C. for 12 h. The mixture was then filtered to remove all solids, and the filtrate was concentrated in vacuo. The residue was redissolved in CH₂Cl₂ and washed with brine. The organic extracts were combined, dried (Na₂SO₄), filtered, and concentrated in vacuo to furnish N-(methyl(oxido){1-[6-(trifluoromethyl)pyridin-3-yl]ethyl}-λ⁴-sulfanylidene)-1H-imidazole-1-carbothioamide as a brown oil (2.78 g, 93%) which was used without further purification: ESIMS m/z 363 ([M+H]⁺).

Step B. Preparation of N,N-dimethyl-N'-(methyl(oxido){1-[6-(trifluoromethyl)pyridin-3-yl]ethyl}-λ⁴-sulfanylidene)thiourea (23)

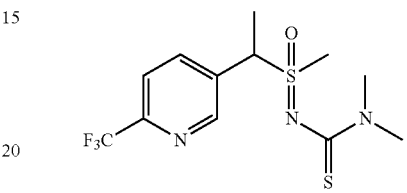

N-(Methyl(oxido){1-[6-(trifluoromethyl)pyridin-3-yl]ethyl}-λ⁴-sulfanylidene)-1H-imidazole-1-carbothioamide (0.088 g, 0.243 mmol) was dissolved in acetonitrile (0.486 mL) with stirring at room temperature. The mixture was then cooled in an ice bath. To this cooled solution was added 40% dimethylamine in water (0.031 mL, 0.243 mmol). Upon completion of reaction, any solids were filtered away from the mixture, and the filtrate was concentrated in vacuo. The remaining crude material was redissolved in ethyl acetate and washed with 1 N HCl and brine. The organic layer was then dried (Na₂SO₄), filtered, and concentrated in vacuo to furnish N,N-dimethyl-N'-(methyl(oxido){1-[6-(trifluoromethyl)pyridin-3-yl]ethyl}-λ⁴-sulfanylidene)thiourea (23) as a yellow oil (0.044 g, 54%): ¹H NMR (400 MHz, CDCl₃) δ (mixture of diastereomers) 8.83 (s, 1H), 8.08 (m, 1H), 7.74 (m, 1H), 5.97 & 5.73 (m, 1H), 3.52 & 3.41 (s, 3H), 3.34 & 3.25 (s, 3H), 3.26 & 3.03 (s, 3H), 1.92 & 1.81 (d, J=7.3 Hz, 3H); ESIMS m/z 340 ([M+H]⁺).

TABLE 2

Insecticidal Compounds

| Cmpd # | Structure | Route | Characterization |
|---|---|---|---|
| 24 | 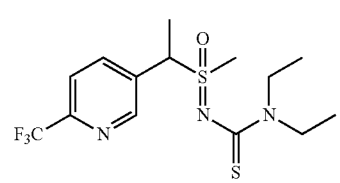 [SMILES: CCN(CC)C(=S)N=S(C)(=O)C(C)c1ccc(C(F)(F)F)nc1] | B | brown oil; ESIMS m/z 368 ([M + H]⁺) |
| 25 | 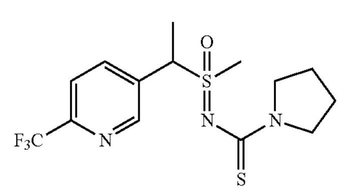 [SMILES: CC(c1ccc(C(F)(F)F)nc1)S(C)(=O)=NC(=S)N1CCCC1] | B | yellow oil; ESIMS m/z 366 ([M + H]⁺) |

TABLE 2-continued

Insecticidal Compounds

| Cmpd # | Structure | Route | Characterization |
|---|---|---|---|
| 26 | 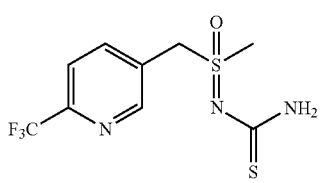 | B | yellow oil; ESIMS m/z 379 ([M + H]+) |
| 27 | 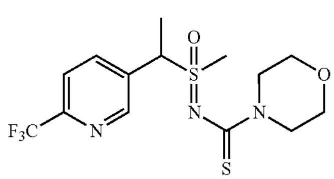 [SMILES: CC(c1ccc(C(F)(F)F)nc1)S(C)(=O)=NC(=S)N1CCOCC1] | B | yellow oil; ESIMS m/z 381 ([M + H]+) |

B = route used in Example 6

Example 7

Preparation of 9H-fluoren-9-ylmethyl[methyl(oxido){[6-(trifluoromethyl)pyridin-3-yl]methyl}-$\lambda^4$-sulfanylidene)amino]carbonothioylcarbamate (28)

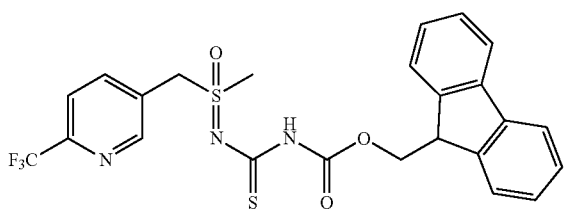 [SMILES: CS(=O)(Cc1ccc(C(F)(F)F)nc1)=NC(=S)NC(=O)OCC1c2ccccc2-c2ccccc21]

9H-Fluoren-9-ylmethyl[(methyl(oxido){[6-(trifluoromethyl)pyridin-3-yl]methyl}-$\lambda^4$-sulfanylidene)amino]carbonothioylcarbamate (28) was synthesized from the corresponding sulfoximide according to the procedure described in Example 4. The compound was isolated as light yellow foam (14.6 g, 100%): mp 92-97° C.; $^1$H NMR (300 MHz, DMSO-$d_6$) δ 11.18 (s, 1H), 8.93 (s, 1H), 8.29 (d, J=7.9 Hz, 1H), 7.98 (d, J=8.2 Hz, 1H), 7.91 (d, J=7.6 Hz, 2H), 7.83 (d, J=7.2 Hz, 2H), 7.43 (t, J=7.2 Hz, 2H), 7.34 (dt, J=1.3, 6.3 Hz, 2H), 5.21 (d, J=2.3 Hz, 2H), 4.33-4.24 (m, 3H), 3.66 (s, 3H); ESIMS m/z 520 ([M+H]+).

Example 8

Preparation of N-(methyl(oxido){[6-(trifluoromethyl)pyridin-3-yl]methyl}-$\lambda^4$-sulfanylidene)thiourea (29)

N-(Methyl(oxido){[6-(trifluoromethyl)pyridin-3-yl]methyl}-$\lambda^4$-sulfanylidene)thiourea (29) was synthesized from Compound 28 according to the procedure described in Example 5. The compound was isolated as a white solid (8.18 g, 92%): mp 107-109° C.; $^1$H NMR (300 MHz, CDCl$_3$) δ 8.82 (s, 1H), 8.11 (d, J=7.6 Hz, 1H), 7.76 (d, J=7.9 Hz, 1H), 6.36 (br s, 1H), 6.19 (br s, 1H), 5.52 (d, J=13.5 Hz, 1H), 5.06 (d, J=13.5 Hz, 1H), 3.39 (s, 3H); ESIMS m/z 340 ([M+H]+).

Example 9

Preparation of 9H-fluoren-9-ylmethyl {[[(6-chloropyridin-3-yl)methyl](methyl) oxido-$\lambda^4$-sulfanylidene]amino}carbonothioylcarbamate (30)

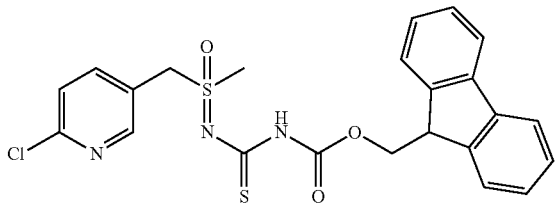 [SMILES: CS(=O)(Cc1ccc(Cl)nc1)=NC(=S)NC(=O)OCC1c2ccccc2-c2ccccc21]

9H-Fluoren-9-ylmethyl{[[(6-chloropyridin-3-yl)methyl](methyl)oxido-$\lambda^4$-sulfanylidene]amino}carbonothioylcarbamate (30) was synthesized from the corresponding sulfoximide according to the procedure described in Example 4. The compound was isolated as a light yellow foam (14.8 g, 92%): mp 98-101° C.; $^1$H NMR (300 MHz, DMSO-$d_6$) δ 11.15 (s, 1H), 8.56 (d, J=2.3 Hz, 1H), 8.05 (dd, J=2.3, 8.2 Hz, 1H), 7.90 (d, J=7.6 Hz, 2H), 7.84 (d, J=7.6 Hz, 2H), 7.59 (d, J=8.2 Hz, 1H), 7.44 (t, J=7.1 Hz, 2H), 7.34

(dt, J=1.0, 7.6 Hz, 2H), 5.09 (s, 2H), 4.32-4.26 (m, 3H), 3.61 (s, 3H); ESIMS m/z 486 ([M+H]$^+$).

(m, 2H), 4.26-4.23 (m, 1H), 3.34 (s, 3H), 2.59 (s, 1.5H), 2.56 (s, 1.5H), 1.93 (d, J=7.1 Hz, 1.5H), 1.87 (d, J=7.1 Hz, 1.5H); ESIMS m/z 480 ([M+H]$^+$).

Example 10

Preparation of N-[[(6-chloropyridin-3-yl)methyl](methyl)oxido-$\lambda^4$-sulfanylidene]thiourea (31)

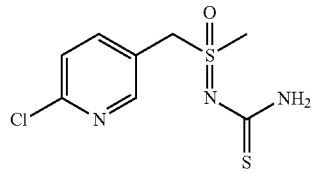

N-[[(6-Chloropyridin-3-yl)methyl](methyl)oxido-$\lambda^4$-sulfanylidene]thiourea (31) was synthesized from Compound 30 according to the procedure described in Example 5. The compound was isolated as a light-orange solid (4.96 g, 62%): mp 155-158° C.; $^1$H NMR (300 MHz, DMSO-d$_6$) δ 8.51 (d, J=2.3 Hz, 1H), 8.12 (br s, 1H), 7.79 (m, 2H), 7.61 (d, J=8.2 Hz, 1H), 5.21 (s, 2H), 3.36 (s, 3H); ESIMS m/z 264 ([M+H]$^+$).

Example 12

Preparation of N-{methyl[1-(6-methylpyridin-3-yl)ethyl]oxido-$\lambda^4$-sulfanylidene}-thiourea (33)

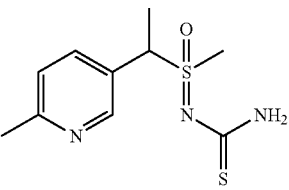

N-{Methyl[1-(6-methylpyridin-3-yl)ethyl]oxido-$\lambda^4$-sulfanylidene}-thiourea (33) was synthesized from Compound 32 according to the procedure described in Example 5. The compound was isolated as a tan solid (0.78 g, 57%): mp 137-140° C.; $^1$H NMR (400 MHz, DMSO-d$_6$) δ 8.57 (d, J=1.8 Hz, 1H), 8.00 (d, J=11.4 Hz, 1H), 7.91-7.83 (m, 2H), 7.30 (t, J=8.0 Hz, 1H), 5.28 (q, J=7.1 Hz, 1H), 3.36 (s, 1.5H), 3.34 (s, 1.5H), 2.48 (s, 1.5 H), 2.48 (s, 1.5H), 1.73 (d, J=6.3 Hz, 1.5H), 1.72 (d, J=6.6 Hz, 1.5H); ESIMS m/z 258 ([M+H]$^+$).

Example 11

Preparation of 9H-fluoren-9-ylmethyl({methyl[1-(6-methylpyridin-3-yl)ethyl]oxido-$\lambda^4$-sulfanylidene}amino)carbonothioylcarbamate (32)

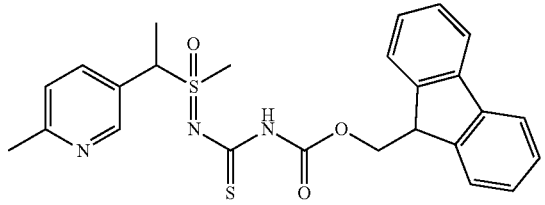 [SMILES: Cc1ccc(C(C)S(C)(=O)=NC(=S)NC(=O)OCC2c3ccccc3-c3ccccc32)cn1]

9H-Fluoren-9-ylmethyl({methyl[1-(6-methylpyridin-3-yl)ethyl]oxido-$\lambda^1$-sulfanylidene}amino)carbonothioylcarbamate (32) was synthesized from the corresponding sulfoximide according to the procedure described in Example 4. The compound was isolated as a tan foam (2.61 g, 54%): mp 101-106° C.; $^1$H NMR (400 MHz, CDCl$_3$) δ 8.59 (dd, J=2.3, 5.5 Hz, 1H), 8.30 (d, J=14.1 Hz, 1H), 8.06 (dd, J=2.3, 8.2 Hz, 0.5H), 7.85 (dd, J=2.5, 8.1 Hz, 0.5H), 7.78 (d, J=7.3 Hz, 2H), 7.59 (d, J=7.6 Hz, 2H), 7.42 (t, J=7.6 Hz, 2H), 7.33 (t, J=7.6 Hz, 2H), 7.23 (d, J=8.3 Hz, 0.5H), 7.20 (d, J=8.1 Hz, 0.5H), 5.16 (q, J=7.1 Hz, 0.5H), 4.71 (q, J=7.1 Hz, 0.5H), 4.51-4.43

Example 13

Preparation of 9H-fluoren-9-ylmethyl[methyl(oxido){1-[4-(trifluoromethyl)phenyl]-ethyl}-$\lambda^4$-sulfanylidene)amino]carbonothioylcarbamate (34)

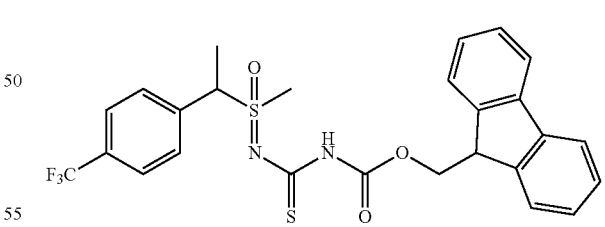

9H-Fluoren-9-ylmethyl[(methyl(oxido){1-[4-(trifluoromethyl)phenyl]-ethyl}-$\lambda^4$-sulfanylidene)amino]carbonothioylcarbamate (34) was synthesized from the corresponding sulfoximide according to the procedure described in Example 4. The compound was isolated as a yellow foam (4.19 g, 99%): mp 86-93° C.; $^1$H NMR (400 MHz, CDCl$_3$) δ 8.29 (br s, 0.5H), 8.24 (br s, 0.5H), 7.80-7.75 (m, 3.5H), 7.65 (d, J=8.3 Hz, 1H), 7.60-7.58 (m, 2.5H), 7.44-7.38 (m, 2.5H), 7.35-7.29 (m, 2.5H), 5.32 (q, J=7.3 Hz, 0.5H), 4.86 (q, J=6.8 Hz, 0.5H), 4.52-4.44 (m, 2H), 4.26-4.23 (m, 1H), 3.32 (s, 1.5H), 3.32 (s, 1.5H), 1.94 (d, J=7.1 Hz, 1.5H), 1.88 (d, J=7.3 Hz, 1.5H); ESIMS m/z 533 ([M+H]$^+$).

Example 14

Preparation of N-(methyl(oxido){1-[4-(trifluoromethyl)phenyl]ethyl}-$\lambda^4$-sulfanylidene)thiourea (35)

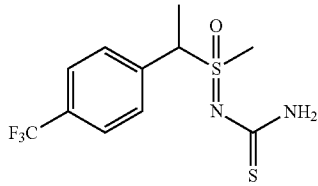 [SMILES: CC(c1ccc(C(F)(F)F)cc1)S(C)(=O)=NC(N)=S]

N-(Methyl(oxido) {1-[4-(trifluoromethyl)phenyl]ethyl}-λ4-sulfanylidene)thiourea (35) was synthesized from Compound 34 according to the procedure described in Example 5. The compound was isolated as a white solid (1.62 g, 67%): mp 166-168° C.; $^1$H NMR (400 MHz, DMSO-d$_6$) δ 8.04 (d, J=13.6 Hz, 1H), 7.90 (dd, J=2.3, 19.2 Hz, 1H), 7.80-7.75 (m, 4H), 5.49-5.44 (m, 1H), 3.37 (s, 1.5H), 3.34 (s, 1.5H), 1.76 (d, J=7.3 Hz, 1.5H), 1.74 (d, J=8.1 Hz, 1.5H); ESIMS m/z 311 ([M+H]$^+$).

Example 15

Preparation of N-[2-(6-chloropyridin-3-yl)-1-oxidotetrahydro-1H-1$\lambda^4$-thien-1-ylidene]thiourea (36)

Step A. Preparation of 9H-fluoren-9-ylmethyl[[2-(6-chloropyridin-3-yl)-1-oxidotetrahydro-1H-1$\lambda^4$-thien-1-ylidene]amino]carbonothioylcarbamate

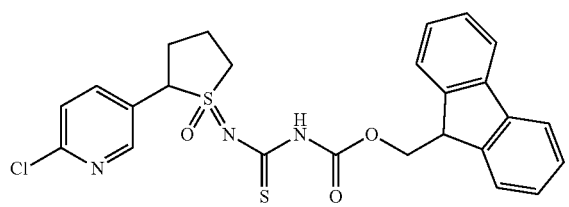 [SMILES: O=C(NC(=S)N=S1(=O)CCCC1c1ccc(Cl)nc1)OCC1c2ccccc2-c2ccccc21]

9H-Fluoren-9-ylmethyl[[2-(6-chloropyridin-3-yl)-1-oxidotetrahydro-1H-1$\lambda^4$-thien-1-ylidene]amino]carbonothioylcarbamate was synthesized from the corresponding sulfoximide according to the procedure described in Example 4. The compound was isolated as an off-white solid (4.4 g, 99%): mp 86-95° C.; ESIMS m/z 512 ([M+H]$^+$).

Step B. Preparation of N-[2-(6-chloropyridin-3-yl)-1-oxidotetrahydro-1H-1$\lambda^4$-thien-1-ylidene]thiourea (36)

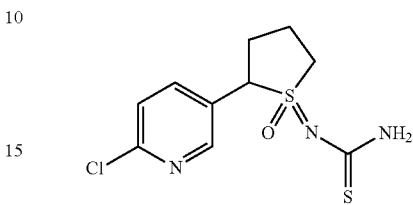

N-[2-(6-Chloropyridin-3-yl)-1-oxidotetrahydro-1H-1$\lambda^4$-thien-1-ylidene]thiourea (36) was synthesized from 9H-fluoren-9-ylmethyl[[2-(6-chloropyridin-3-yl)-1-oxidotetrahydro-1H-1$\lambda^4$-thien-1-ylidene]amino]carbonothioylcarbamate according to the procedure described in Example 5. The compound was isolated as an off-white solid (0.51 g, 20%): mp 168-172° C.; $^1$H NMR (300 MHz, acetone-d$_6$) δ (2:1 mixture of two diastereomers) 8.50 (d, J=2.2 Hz, 1H), 8.43 (d, J=2.5 Hz, 1H), 7.96 (dd, J=8.5, 2.5 Hz, 1H), 7.86 (dd, J=6.6, 1.1 Hz, 1H), 7.68 (br d, J=20.3 Hz, 2H), 7.51 (d, J=8.5 Hz, 1H), 7.47 (d, J=6.6 Hz, 1H), 5.14 (dd, J=11.8, 7.4 Hz, 2H), 4.60 (m, 2H), 4.26 (m, 2H), 2.20-2.65 (m, 8H); ESIMS m/z 290 ([M+H]$^+$).

Example 16

Preparation of methyl 4-({[(methyl(oxido){1-[6-(trifluoromethyl)pyridin-3-yl]ethyl}-$\lambda^4$-sulfanylidene)amino]carbonothioyl}amino)-4-oxobutanoate (37)

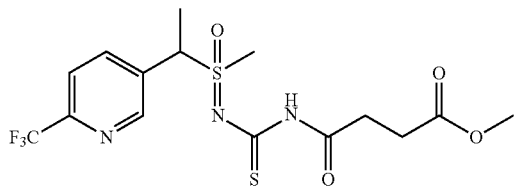 [SMILES: COC(=O)CCC(=O)NC(=S)N=S(C)(=O)C(C)c1ccc(C(F)(F)F)nc1]

Methyl chlorosuccinate (0.099 mL, 0.803 mmol) was dissolved in acetone (2.7 mL) at 25° C. with stirring. To this solution was added Compound 22 (0.250 g, 0.803 mmol) in acetone (4 mL). Next, triethylamine (0.112 mL, 0.803 mmol) was added to the reaction mixture which was warmed to 45° C. for 6 h. The warm solution was then filtered, and the residue was washed with warm acetone. The filtrate was concentrated in vacuo to furnish methyl 4-({[(methyl(oxido){1-[6-(trifluoromethyl)pyridin-3-yl]ethyl}-$\lambda^4$-sulfanylidene)amino]carbonothioyl}amino)-4-oxobutanoate (37) as a yellow solid (0.342 g, >99%): mp 131-133° C.; $^1$H NMR (400 MHz, CDCl$_3$) δ (mixture of diastereomers) 8.81 (m, 1H), 8.39 & 8.23 (m, 1H), 7.78 (m, 1H), 5.32 & 5.10 (q, J=7.1

Hz, 1H), 3.71 (m, 2H), 3.46 (m, 3H), 3.11 (m, 2H), 2.67 (m, 3H), 1.97 & 1.92 (d, J=7.1 Hz, 3H); ESIMS m/z 426 ([M+H]$^+$).

Example 17

Preparation of N"-hydroxy-N-(methyl(oxido){1-[6-(trifluoromethyl)pyridin-3-yl]ethyl}-λ$^4$-sulfanylidene)guanidine (38)

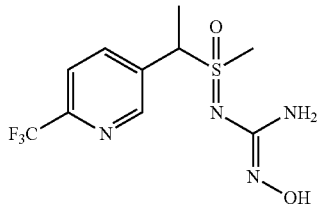 [SMILES: CC(c1ccc(C(F)(F)F)nc1)S(C)(=O)=N/C(N)=N/O]

Methyl(oxido){1-[6-(trifluoromethyl)pyridin-3-yl]ethyl}-λ$^4$-sulfanylidene cyanamide (0.200 g, 0.721 mmol) was dissolved in ethanol (2.7 mL) at room temperature. In a separate flask, hydroxylamine hydrochloride (0.099 g, 1.44 mmol) and Na$_2$CO$_3$ (0.229 g, 2.16 mmol) were dissolved in water (0.9 mL) and then added to the reaction mixture which was heated to reflux for 8 h. Upon completion of reaction, the solvent was removed in vacuo. Water was added to the residue and solids were collected via vacuum filtration to furnish N"-hydroxy-N-(methyl(oxido) {1-[6-(trifluoromethyl)pyridin-3-yl]ethyl}-λ$^4$-sulfanylidene) guanidine (38) as a white powder (0.070 g, 31%): mp 157-159° C.; $^1$H NMR (400 MHz, CDCl$_3$) δ (mixture of diastereomers) 8.79 (s, 1H), 8.06 (m, 1H), 7.74 (m, 1H), 5.11 & 4.98 (m, 1H), 4.52 (br s, 1H), 4.44 (br s, 1H), 3.09 & 2.96 (s, 3H), 1.89 & 1.86 (d, J=7.3 Hz, 3H); ESIMS m/z 311 ([M−H]$^−$).

Example 18

Preparation of N-[[(6-chloropyridin-3-yl)methyl](methyl)oxido-λ$^4$-sulfanylidene]-N"-hydroxyguanidine (39)

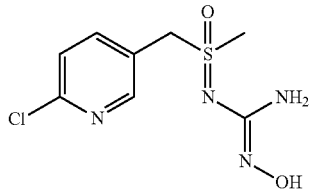 [SMILES: CS(=O)(Cc1ccc(Cl)nc1)=N/C(N)=N/O]

N-[[(6-Chloropyridin-3-yl)methyl](methyl)oxido-λ$^4$-sulfanylidene]-N"-hydroxyguanidine (39) was synthesized from the corresponding N-cyano sulfoximine according to the procedure described in Example 17. The compound was isolated as a white solid (0.184 g, 54%): mp 156-158° C.; $^1$H NMR (400 MHz, CDCl$_3$) δ (mixture of diastereomers) 8.40 (s, 1H), 7.81 (m, 1H), 7.42 (m, 1H), 4.75 (m, 2H), 3.10 & 3.01 (s, 3H); ESIMS m/z 263 ([M+H]$^+$)

Example 19

Preparation of N-[[1-(6-chloropyridin-3-yl)-2-cyclopropylethyl](methyl)oxido-λ$^4$-sulfanylidene]-N"-hydroxyguanidine (40)

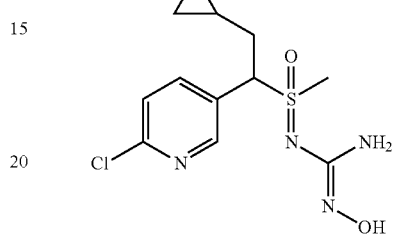

N-[[1-(6-Chloropyridin-3-yl)-2-cyclopropylethyl](methyl)oxido-λ$^4$-sulfanylidene]-N"-hydroxyguanidine (40) was synthesized from the corresponding N-cyano sulfoximine according to the procedure described in Example 17. The compound was isolated as a light yellow semi-solid (0.142 g, 34%): $^1$H NMR (400 MHz, CDCl$_3$) δ (mixture of diastereomers) 8.47 (s, 1H), 7.91 (m, 1H), 7.41 (m, 1H), 3.04 & 2.94 (s, 3H), 2.43 & 2.31 (m, 1H), 2.00 (m, 2H), 0.45 (m, 3H), 0.14 (m, 2H); ESIMS m/z 317 ([M+H]$^+$).

Example 20

Preparation of N-[[(3E)-4-chloro-1-(6-chloropyridin-3-yl)but-3-enyl](methyl) oxido-λ$^4$-sulfanylidene]-N"-hydroxyguanidine (41)

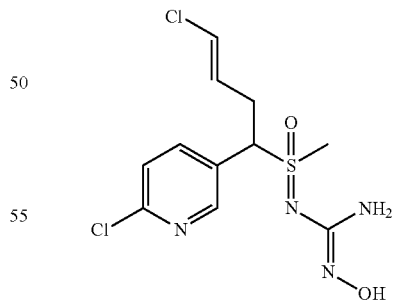

N-[[(3E)-4-Chloro-1-(6-chloropyridin-3-yl)but-3-enyl](methyl)oxido-λ$^4$-sulfanylidene]-N"-hydroxyguanidine (41) was synthesized from the corresponding N-cyano sulfoximine according to the procedure described in Example 17. The compound was isolated as a light yellow semi-solid (0.182 g, 50%): $^1$H NMR (400 MHz, CDCl$_3$) δ (mixture of diastereomers) 8.42 (m, 1H), 7.83 (m, 1H), 7.43 (m, 1H), 6.07

(m, 1H), 5.64 (m, 1H), 4.58 & 4.49 (m, 2H), 3.22 (m, 1H), 3.05 & 2.94 (s, 3H); ESIMS m/z 337 ([M+H]+).

Example 21

Preparation of N'-hydroxy-N-(methyl(oxido){[6-(trifluoromethyl)pyridin-3-yl]methyl}-λ⁴-sulfanylidene)guanidine (42)

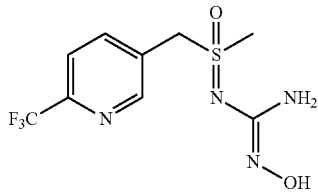 [SMILES: CS(=O)(Cc1ccc(C(F)(F)F)nc1)=N/C(N)=N/O]

N"-Hydroxy-N-(methyl(oxido) {[6-(trifluoromethyl)pyridin-3-yl]methyl}-λ⁴-sulfanylidene)guanidine (42) was synthesized from the corresponding N-cyano sulfoximine according to the procedure described in Example 17. The compound was isolated as a white solid (0.188 g, 56%): mp 118-120° C.; ¹H NMR (400 MHz, CDCl₃) δ (mixture of diastereomers) 8.74 (s, 1H), 8.04 (m, 1H), 7.77 (m, 1H), 4.34 (s, 2H), 3.14 & 2.91 (s, 3H); ESIMS m/z 297 ([M+H]+).

Example 22

Preparation of N-[{2-cyclopropyl-1-[6-(trifluoromethyl)pyridin-3-yl]ethyl}(methyl)oxido-λ⁴-sulfanylidene]-N"-hydroxyguanidine (43)

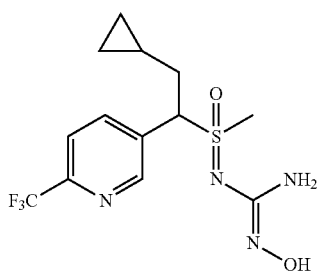 [SMILES: CS(=O)(=N/C(N)=N/O)C(CC1CC1)c1ccc(C(F)(F)F)nc1]

N-[{2-Cyclopropyl-1-[6-(trifluoromethyl)pyridin-3-yl]ethyl}(methyl)oxido-λ⁴-sulfanylidene]-N"-hydroxyguanidine (43) was synthesized from the corresponding N-cyano sulfoximine according to the procedure described in Example 17. The compound was isolated as a brown semi-solid (0.323 g, 51%): ¹H NMR (400 MHz, CDCl₃) δ (mixture of diastereomers) 8.82 (m, 1H), 8.13 (m, 1H), 7.76 (m, 1H), 3.06 & 2.96 (s, 3H), 2.48 & 2.36 (m, 1H), 1.97 (m, 2H), 0.45 (m, 3H), 0.15 (m, 2H); ESIMS m/z 351 ([M+H]+).

Example 23

Preparation of N"-(acetyloxy)-N-(methyl(oxido){1-[6-(trifluoromethyl)pyridin-3-yl]ethyl}-λ⁴-sulfanylidene)guanidine (44)

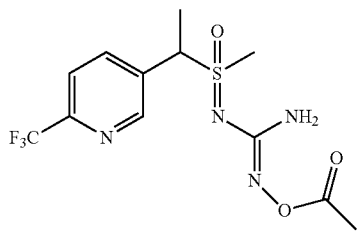 [SMILES: CC(=O)O/N=C(\N)N=S(C)(=O)C(C)c1ccc(C(F)(F)F)nc1]

Compound 38 (0.300 g, 0.967 mmol) was dissolved in glacial acetic acid (48 mL) at 25° C. To this solution was added acetic anhydride (0.100 mL, 1.06 mmol). The mixture was allowed to stir for 1 h at room temperature under N₂. The mixture was then poured slowly into saturated aqueous NaHCO₃. Once pH 6-7 was reached, the solution was extracted with CH₂Cl₂. The organic extracts were combined, washed with brine, dried (Na₂SO₄), and concentrated in vacuo to furnish N"-(acetyloxy)-N-(methyl(oxido){1-[6-(trifluoromethyl)pyridin-3-yl]ethyl}-λ⁴-sulfanylidene)guanidine (44) as a white semi-solid (0.038 g, 13%): ¹H NMR (400 MHz, CDCl₃) δ 8.81 (s, 1H), 8.13 (m, 1H), 7.77 (m, 1H), 4.88 (q, J=7.1 Hz, 1H), 3.14 (s, 3H), 2.49 (s, 3H), 1.97 (d, J=7.1 Hz, 3H); ESIMS m/z 353 ([M+H]+).

Example 24

Preparation of N-(methyl(oxido){1-[6-(trifluoromethyl)pyridin-3-yl]ethyl}-λ⁴-sulfanylidene)guanidine (45)

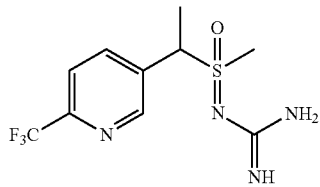 [SMILES: CC(c1ccc(C(F)(F)F)nc1)S(C)(=O)=NC(=N)N]

Compound 38 (0.300 g, 0.967 mmol) was dissolved in glacial acetic acid (48 mL) at room temperature. To this solution was added acetic anhydride (0.100 mL, 1.06 mmol). The mixture was allowed to stir for 1 h at room temperature under N₂. Next, 5% Pd/C (2 g, 0.967 mmol) was added, and the mixture was hydrogenated (30 psi). The Pd/C was filtered through a pad of Celite® and the filtrate was poured slowly into saturated aqueous NaHCO₃. Once pH>7 was reached, the solution was extracted with CH₂Cl₂. The organic extracts were combined, washed with brine, dried (Na₂SO₄), and concentrated in vacuo to furnish N-(methyl(oxido) {1-[6-(trifluoromethyl)pyridin-3-yl]ethyl}-λ⁴-sulfanylidene) guanidine (45) as a crude yellow oil (0.111 g, 39%): ¹H NMR (400 MHz, CDCl₃) δ (mixture of diastereomers) 8.82 (s, 1H), 8.10

(m, 1H), 7.74 (m, 1H), 5.39 & 5.27 (q, J=7.3 Hz, 1H), 3.19 & 3.00 (s, 3H), 1.90 & 1.85 (d, J=7.1 Hz, 3H); ESIMS m/z 295 ([M+H]+).

Example 25

Preparation of N'-[(4-chlorobenzyl)oxy]-N-(methyl (oxido){1-[6-(trifluoromethyl)pyridin-3-yl]ethyl}-λ4-sulfanylidene)guanidine (46)

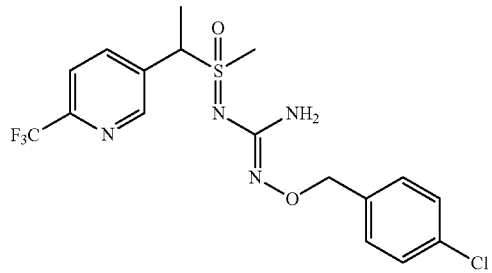 [SMILES: CC(c1ccc(C(F)(F)F)nc1)S(C)(=O)=N/C(N)=N/OCc1ccc(Cl)cc1]

NaH (60% dispersion in mineral oil, 0.026 g, 0.644 mmol) was suspended in THF (1.6 mL) and cooled to 0° C. Compound 38 (0.200 g, 0.644 mmol) was added, and after 15 min, 4-chlorobenzyl chloride (0.104 g, 0.644 mmol) dissolved in THF (1 mL) was then added dropwise to the reaction mixture. The ice bath was removed, and the mixture was allowed to warm to room temperature. The mixture was quenched with saturated aqueous NH4Cl solution and diluted with ethyl acetate. The layers were separated, and the organic layer was washed with saturated aqueous NH4Cl solution and brine. The organic layer was then concentrated in vacuo. The crude material was purified using reverse-phase HPLC eluting with acetonitrile/water mixtures to furnish N'-[(4-chlorobenzyl) oxy]-N-(methyl(oxido){1-[6-(trifluoromethyl)pyridin-3-yl])ethyl}-λ4-sulfanylidene)guanidine (46) as a tan semi-solid (0.012 g, 4%): 1H NMR (400 MHz, CD3OD) δ (mixture of diastereomers) 8.58 (m, 1H), 7.97 (m, 1H), 7.70 (m, 1H), 7.30 (m, 2H), 7.20 (m, 2H), 4.89 (m, 1H), 4.74 (s, 2H), 2.89 & 2.82 (s, 3H), 1.68 & 1.64 (d, J=7.3 Hz, 3H): ESIMS m/z 435 ([M+H]+).

TABLE 3

Insecticial Compounds

| Cmpd # | Structure | Route | Characterization |
|---|---|---|---|
| 47 | 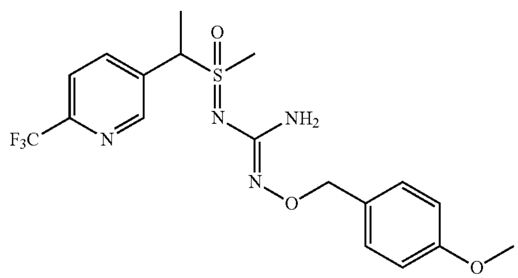 [SMILES: COc1ccc(CO/N=C(\N)N=S(C)(=O)C(C)c2ccc(C(F)(F)F)nc2)cc1] | C | brown oil; ESIMS m/z 431 ([M + H]+) |
| 48 | 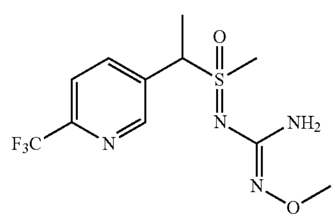 [SMILES: CO/N=C(\N)N=S(C)(=O)C(C)c1ccc(C(F)(F)F)nc1] | C | yellow semi-solid; ESIMS m/z 325 ([M + H]+) |
| 49 | 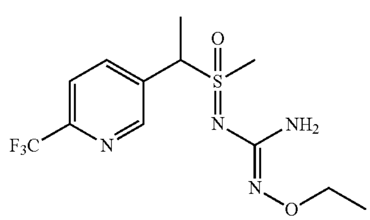 [SMILES: CCO/N=C(\N)N=S(C)(=O)C(C)c1ccc(C(F)(F)F)nc1] | C | pale yellow semi solid; ESIMS m/z 339 ([M + H]+) |
| 50 | 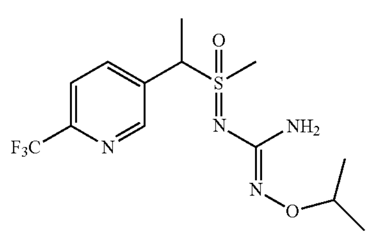 [SMILES: CC(C)O/N=C(\N)N=S(C)(=O)C(C)c1ccc(C(F)(F)F)nc1] | C | yellow semi-solid; ESIMS m/z 353 ([M + H]+) |

TABLE 3-continued

| Cmpd # | Structure | Route | Characterization |
|---|---|---|---|
| 51 | 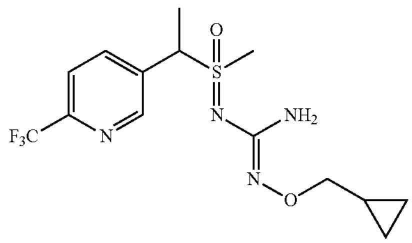 [SMILES: CC(c1ccc(C(F)(F)F)nc1)S(C)(=O)=N/C(N)=N/OCC1CC1] | C | pale yellow semi-solid; ESIMS m/z 365 ([M + H]$^+$) |
| 52 | 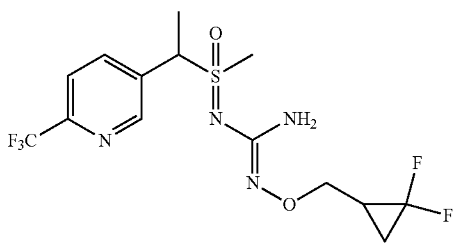 [SMILES: CC(c1ccc(C(F)(F)F)nc1)S(C)(=O)=N/C(N)=N/OCC1CC1(F)F] | C | pale yellow semi-solid; ESIMS m/z 401 ([M + H]$^+$) |
| 53 | 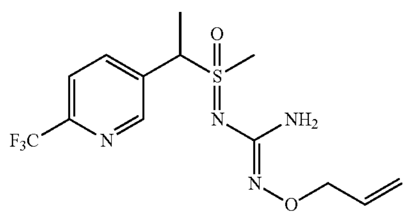 [SMILES: C=CCO/N=C(\N)N=S(C)(=O)C(C)c1ccc(C(F)(F)F)nc1] | C | light yellow oil; ESIMS m/z 351 ([M + H]$^+$) |
| 54 | 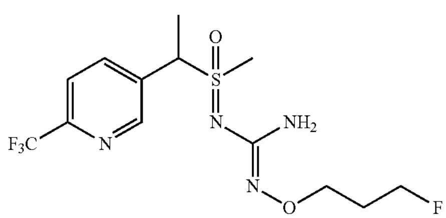 [SMILES: CC(c1ccc(C(F)(F)F)nc1)S(C)(=O)=N/C(N)=N/OCCCF] | C | orange oil; ESIMS m/z 371 ([M + H]$^+$) |
| 55 | 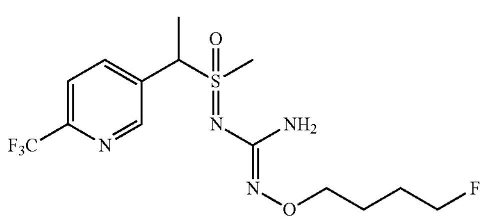 [SMILES: CC(c1ccc(C(F)(F)F)nc1)S(C)(=O)=N/C(N)=N/OCCCCF] | C | light brown oil; ESIMS m/z 385 ([M + H]$^+$) |
| 56 | 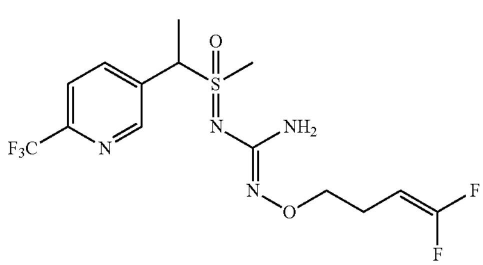 [SMILES: CC(c1ccc(C(F)(F)F)nc1)S(C)(=O)=N/C(N)=N/OCCC=C(F)F] | C | light brown oil; ESIMS m/z 401 ([M + H]$^+$) |

TABLE 3-continued
Insecticial Compounds
| Cmpd # | Structure | Route | Characterization |
|---|---|---|---|
| 57 | 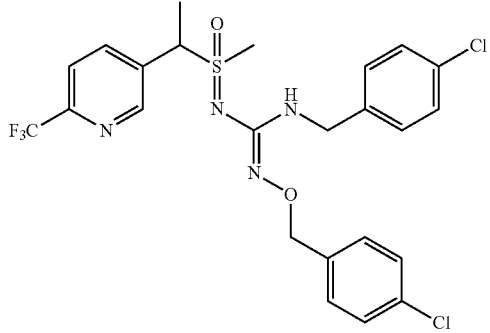 [SMILES: CC(c1ccc(C(F)(F)F)nc1)S(C)(=O)=N/C(=N/OCc1ccc(Cl)cc1)NCc1ccc(Cl)cc1] | C | white semi-solid; ESIMS m/z 559 ([M + H]$^+$) |
| 58 | 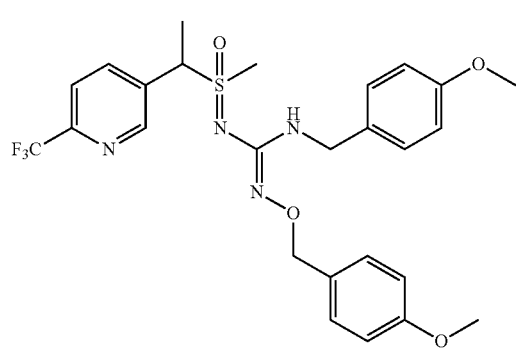 [SMILES: COc1ccc(CN/C(N=S(C)(=O)C(C)c2ccc(C(F)(F)F)nc2)=N\OCc2ccc(OC)cc2)cc1] | C | light yellow semi-solid; ESIMS m/z 551 ([M + H]$^+$) |
| 59 | 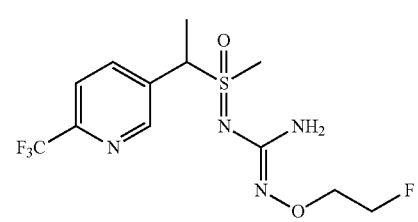 [SMILES: CC(c1ccc(C(F)(F)F)nc1)S(C)(=O)=N/C(N)=N/OCCF] | C | brown oil; ESIMS m/z 357 ([M + H]$^+$) |
| 60 | 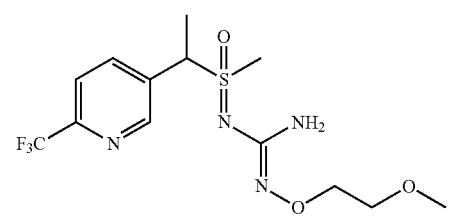 [SMILES: COCCO/N=C(\N)N=S(C)(=O)C(C)c1ccc(C(F)(F)F)nc1] | C | orange oil; ESIMS m/z 369 ([M + H]$^+$) |
| 61 | 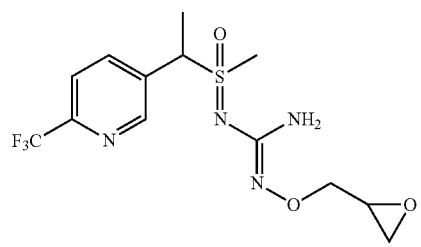 [SMILES: CC(c1ccc(C(F)(F)F)nc1)S(C)(=O)=N/C(N)=N/OCC1CO1] | C | brown oil; ESIMS m/z 367 ([M + H]$^+$) |

TABLE 3-continued

Insecticial Compounds

| Cmpd # | Structure | Route | Characterization |
|---|---|---|---|
| 62 | 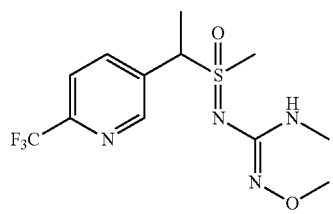 | C | yellow oil; ESIMS m/z 413 ([M + H]+) |

C = Route used in Example 25

Example 26

Preparation of N''-methoxy-N-methyl-N'-(methyl (oxido){1-[6-(trifluoromethyl)pyridin-3-yl]ethyl}-λ⁴-sulfanylidene)guanidine (63)

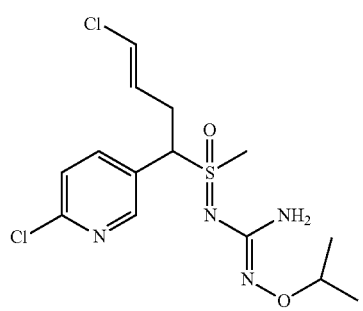 [SMILES: CC(C)O/N=C(\N)N=S(C)(=O)C(C/C=C/Cl)c1ccc(Cl)nc1]

Potassium carbonate (0.044 g, 0.322 mmol) was suspended in acetonitrile (0.644 mL) at room temperature. To this mixture was added Compound 38 (0.100 g, 0.322 mmol). The solution was allowed to stir at room temperature for 30 min before addition of methyl iodide (0.020 mL, 0.322 mmol). Upon completion of addition, the reaction was allowed to stir overnight. The mixture was filtered and concentrated in vacuo to furnish N''-methoxy-N-methyl-N'-(methyl(oxido){1-[6-(trifluoromethyl)pyridin-3-yl]ethyl}-λ⁴-sulfanylidene) guanidine (63) as a yellow semi-solid (0.215 g, >99%): ¹H NMR (400 MHz, CDCl₃) δ (mixture of diastereomers) 9.05 (s, 1H), 8.41 (m, 1H), 7.81 (m, 1H), 6.31 & 6.20 (q, J=7.1 Hz, 1H), 3.87 & 3.83 (s, 3H), 3.70 (s, 3H), 3.47 & 3.36 (s, 3H), 1.97 & 1.95 (m, 3H); ESIMS m/z 339 ([M+H]⁺).

Example 27

Preparation of N-[[(3E)-4-chloro-1-(6-chloropyridin-3-yl)but-3-enyl](methyl) oxido-λ⁴-sulfanylidene]-N''-isopropoxyguanidine (64)

N-[[(3E)-4-Chloro-1-(6-chloropyridin-3-yl)but-3-enyl](methyl)oxido-λ⁴-sulfanylidene]-N''-isopropoxyguanidine (64) was synthesized from Compound 41 according to the procedure described in Example 25. The compound was isolated as a golden semi-solid (0.080 g, 44%): ¹H NMR (400 MHz, CDCl₃) δ (mixture of diasteroemers) 8.37 (s, 1H), 7.82 (m, 1H), 7.44 (m, 1H), 6.05 (m, 1H), 5.65 (m, 1H), 4.53 & 4.44 (m, 2H), 4.10 (m, 1H), 3.20 (m, 1H), 3.09 & 2.93 (s, 3H), 1.22 (m, 3H), 0.86 (m, 3H); ESIMS m/z 379 ([M+H]⁺).

Example 28

Preparation of 2,2,2-trifluoro-N-(methyl(oxido){1-[6-(trifluoromethyl)pyridin-3-yl]ethyl}-λ⁴-sulfanylidene)acetamide (65)

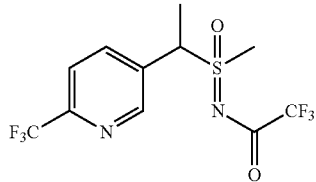 [SMILES: CC(c1ccc(C(F)(F)F)nc1)S(C)(=O)=NC(=O)C(F)(F)F]

5-[1-(Methylsulfonimidoyl)ethyl]-2-(trifluoromethyl)pyridine (0.075 g, 0.297 mmol) was dissolved in pyridine (0.24 mL) at 25° C. Next, trifluoroacetic anhydride (0.471 mL, 2.58 mmol) was added to the reaction mixture which was then allowed to stir for 2 h. The mixture was diluted with ethyl acetate, washed with 5% citric acid, brine, and saturated aqueous NaHCO₃. The organic layer was dried (MgSO₄) and concentrated in vacuo to furnish 2,2,2-trifluoro-N-(methyl(oxido) {1-[6-(trifluoromethyl)pyridin-3-yl]ethyl}-λ⁴-sulfanylidene)acetamide (65) as a yellow oil (43 mg, 42%): ¹H NMR (400 MHz, CDCl₃) δ (mixture of diastereomers) 8.80 (m, 1H), 8.10 (m, 1H), 7.82 (m, 1H), 4.90 (m, 1H), 3.32 & 3.21 (s, 3H), 2.01 & 1.95 (d, J=7.3 Hz, 3H); ESIMS m/z 347 ([M+H]⁺).

Example 29

Preparation of 2,2-difluoro-N-(methyl(oxido){1-[6-(trifluoromethyl)pyridin-3-yl]ethyl}-λ⁴-sulfanylidene)acetamide (66)

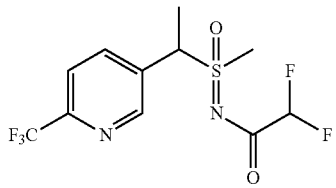 [SMILES: CC(c1ccc(C(F)(F)F)nc1)S(C)(=O)=NC(=O)C(F)F]

N-(Methyl(oxido) {1-[6-(trifluoromethyl)pyridin-3-yl]ethyl}-λ⁴-sulfanylidene)-1H-imidazole-1-carbothioamide (300 mg, 0.83 mmol) was dissolved in acetonitrile (10 mL) and cooled to 0° C. While stirring, hydrazine (64-65% solution in water, 30.8 µL, 31.9 mg, 0.64 mmol) was added via syringe. After 10 min, the mixture was poured into a saturated aqueous solution of $NH_4Cl$ (100 mL) which was extracted once with $CHCl_3$ (100 mL). The organic phase was washed with several aliquots of saturated aqueous $NH_4Cl$ until the aqueous phase was slightly acidic, and then dried ($Na_2SO_4$). After filtration, difluoroacetic anhydride (154 µL, 216 mg, 1.24 mmol) was added dropwise to the organic phase, which was then stirred at 25° C. for 20 min. The solvent was removed under reduced pressure. The crude concentrate contained the unstable difluoroacetylsemicarbazide and difluoroacetamide as the main products according to LC-MS analysis of the crude reaction mixture. The mixture was added slowly to saturated aqueous $NaHCO_3$ and extracted with $CHCl_3$ (3×50 mL). The combined organic extracts were washed with saturated aqueous ammonium hydroxide (4×50 mL), saturated aqueous $NH_4Cl$ (50 mL aliquots, until neutral), dried ($NaSO_4$) and concentrated under reduced pressure. The compound was purified by reverse-phase chromatography (water-acetonitrile gradient) to furnish pure 2,2-difluoro-N-(methyl(oxido){1-[6-(trifluoromethyl)pyridin-3-yl]ethyl}-λ⁴-sulfanylidene)acetamide (66) as a yellowish oil (38 mg, 13%): ¹H-NMR (400 MHz, $CDCl_3$): δ 8.79 (d, J=2.1 Hz, 0.33H), 8.74 (d, J=2.1 Hz, 0.67H), 8.09 (dd, J=8.2 Hz, J=2.1 Hz, 0.33H), 8.04 (dd, J=8.2 Hz, J=2.1 Hz, 0.67H), 7.79 (d, J=8.2 Hz, 0.33H), 7.76 (d, J=8.2 Hz, 0.67H), 5.83 (t, J=54.5 Hz, 0.33H), 5.73 (t, J=54.5 Hz, 0.67H), 4.95 (q, J=7.2 Hz, 0.33H), 4.91 (q, J=7.2 Hz, 0.67H), 3.28 (s, 2H), 3.14 (s, 1H), 1.97 (d, J=7.2 Hz, 2H), 1.89 (d, J=7.2 Hz, 1H); ESIMS m/z 331 ([M+H]⁺)

Example 30

Preparation of 2,2-dimethyl-N-(methyl(oxido){1-[6-(trifluoromethyl)pyridin-3-yl]ethyl}-λ⁴-sulfanylidene)propanamide (67)

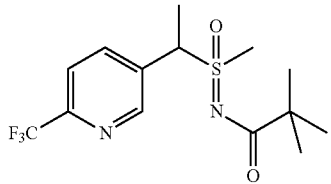 [SMILES: CC(c1ccc(C(F)(F)F)nc1)S(C)(=O)=NC(=O)C(C)(C)C]

5-[1-(Methylsulfonimidoyl)ethyl]-2-(trifluoromethyl)pyridine (300 mg, 1.19 mmol) in pyridine (1 mL) and pivalic anhydride (244 mg, 1.31 mmol, 1.1 eq) were stirred at 90° C. for 1 h. Hünig's base (2 drops) was added, and the mixture was heated to reflux for 2 h. The solvent was removed under reduced pressure and the residue purified by column chromatography (methanol-methylene chloride gradient). The product was obtained as a white to off-white powder (125 mg, 31%): ¹H NMR (400 MHz, $CDCl_3$): δ 8.78 (d, J=1.9 Hz, 0.6H), 8.74 (d, J=1.9 Hz, 0.4H), 8.07 (dd, J=8.1 Hz, J=2.1 Hz, 0.6H), 8.01 (dd, J=8.1 Hz, J=2.1 Hz, 0.4H), 7.76 (d, J=8.2 Hz, 1H), 7.71 (d, J=8.2 Hz, 0.4H), 5.03 (q, J=7.2 Hz, 0.6H), 4.97 (q, J=7.2 Hz, 0.4H), 3.20 (s, 1.2H), 3.01 (s, 1.8H), 1.90 (d, J=7.2 Hz, 1.2H), 1.80 (d, J=7.2 Hz, 1.8H), 1.22 (s, 5.4H), 1.07 (s, 3.6H); ESIMS m/z 337 ([M+H]⁺).

Example 31

Insecticidal Testing

Compounds 1-67 were tested against green peach aphid using procedures described hereinafter.

Insecticidal Test for Green Peach Aphid (*Myzus persicae*) in Foliar Spray Assay Cabbage seedlings grown in 3-inch pots, with 2-3 small (3-5 cm) true leaves, were used as test substrate. The seedlings were infested with 20-50 green peach aphids (wingless adult and nymph) 1-2 d prior to chemical application. Four seedlings were used for each treatment. Compounds (2 mg) were dissolved in 2 mL of acetone-methanol (1:1) solvent, forming stock solutions of 1000 ppm. The stock solutions were diluted 5× with 0.025% Tween 20 in $H_2O$ to obtain a solution at 200 ppm. A hand-held Devilbiss aspirator sprayer was used for spraying a solution to both sides of cabbage leaves until runoff. Reference plants (solvent check) were sprayed with the diluent only. Treated plants were held in a holding room for 3 d at approximately 23° C. and 40% RH prior to grading. Evaluation was conducted by counting the number of live aphids per plant under a microscope. Insecticidal activity was measured by using Abbott's correction formula:

Corrected % Control=100*(X−Y)/X where X=No. of live aphids on solvent check plants
Y=No. of live aphids on treated plants

TABLE 4

Insecticidal Activity

| Cmpd # | Rating against green peach aphid on cabbage (foliar spray) 200 ppm |
|---|---|
| 1 | C |
| 2 | C |
| 3 | A |
| 4 | B |
| 5 | B |
| 6 | A |
| 7 | A |
| 8 | A |
| 9 | A |
| 10 | A |
| 11 | A |
| 12 | A |
| 13 | A |
| 14 | A |
| 15 | A |
| 16 | A |
| 17 | A |
| 18 | A |
| 19 | A |
| 20 | B |
| 21 | B |

TABLE 4-continued

Insecticidal Activity

| Cmpd # | Rating against green peach aphid on cabbage (foliar spray) 200 ppm |
|---|---|
| 22 | A |
| 23 | A |
| 24 | A |
| 25 | A |
| 26 | A |
| 27 | A |
| 28 | B |
| 29 | A |
| 30 | B |
| 31 | A |
| 32 | B |
| 33 | A |
| 34 | B |
| 35 | B |
| 36 | A |
| 37 | A |
| 38 | A |
| 39 | A |
| 40 | B |
| 41 | B |
| 42 | A |
| 43 | A |
| 44 | A |
| 45 | B |
| 46 | A |
| 47 | A |
| 48 | A |
| 49 | A |
| 50 | A |
| 51 | A |
| 52 | A |
| 53 | A |
| 54 | A |
| 55 | A |
| 56 | A |
| 57 | B |
| 58 | A |
| 59 | A |
| 60 | A |
| 61 | A |
| 62 | A |
| 63 | A |
| 64 | B |
| 65 | C |
| 66 | A |
| 67 | B |

In each case of Table 4 the rating scale is as follows:

| % Control (or Mortality) | Rating |
|---|---|
| 80-100 | A |
| Less than 80 | B |
| Not tested | C |

Acid & Salt Derivatives, and Solvates

The compounds disclosed in this invention can be in the form of pesticidally acceptable acid addition salts.

By way of non-limiting example, an amine function can form salts with hydrochloric, hydrobromic, sulfuric, phosphoric, acetic, benzoic, citric, malonic, salicylic, malic, fumaric, oxalic, succinic, tartaric, lactic, gluconic, ascorbic, maleic, aspartic, benzenesulfonic, methanesulfonic, ethanesulfonic, hydroxymethanesulfonic, and hydroxyethanesulfonic, acids.

Additionally, by way of non-limiting example, an acid function can form salts including those derived from alkali or alkaline earth metals and those derived from ammonia and amines. Examples of preferred cations include sodium, potassium, magnesium, and aminium cations.

The salts are prepared by contacting the free base form with a sufficient amount of the desired acid to produce a salt. The free base forms may be regenerated by treating the salt with a suitable dilute aqueous base solution such as dilute aqueous NaOH, potassium carbonate, ammonia, and sodium bicarbonate. As an example, in many cases, a pesticide is modified to a more water soluble form e.g. 2,4-dichlorophenoxy acetic acid dimethyl amine salt is a more water soluble form of 2,4-dichlorophenoxy acetic acid a well known herbicide.

The compounds disclosed in this invention can also form stable complexes with solvent molecules that remain intact after the non-complexed solvent molecules are removed from the compounds. These complexes are often referred to as "solvates".

Stereoisomers

Certain compounds disclosed in this invention can exist as one or more stereoisomers. The various stereoisomers include geometric isomers, diastereomers, and enantiomers. Thus, the compounds disclosed in this invention include racemic mixtures, individual stereoisomers, and optically active mixtures. It will be appreciated by those skilled in the art that one stereoisomer may be more active than the others. Individual stereoisomers and optically active mixtures may be obtained by selective synthetic procedures, by conventional synthetic procedures using resolved starting materials, or by conventional resolution procedures.

Pests

In another embodiment, the invention disclosed in this document can be used to control pests.

In another embodiment, the invention disclosed in this document can be used to control pests of the Phylum Nematoda.

In another embodiment, the invention disclosed in this document can be used to control pests of the Phylum Arthropoda.

In another embodiment, the invention disclosed in this document can be used to control pests of the Subphylum Chelicerata.

In another embodiment, the invention disclosed in this document can be used to control pests of the Class Arachnida.

In another embodiment, the invention disclosed in this document can be used to control pests of the Subphylum Myriapoda.

In another embodiment, the invention disclosed in this document can be used to control pests of the Class Symphyla.

In another embodiment, the invention disclosed in this document can be used to control pests of the Subphylum Hexapoda.

In another embodiment, the invention disclosed in this document can be used to control pests of the Class Insecta.

In another embodiment, the invention disclosed in this document can be used to control Coleoptera (beetles). A non-exhaustive list of these pests includes, but is not limited to, *Acanthoscelides* spp. (weevils), *Acanthoscelides obtectus* (common bean weevil), *Agrilus planipennis* (emerald ash borer), *Agriotes* spp. (wireworms), *Anoplophora glabripennis* (Asian longhorned beetle), *Anthonomus* spp. (weevils), *Anthonomus grandis* (boll weevil), *Aphidius* spp., *Apion* spp. (weevils), *Apogonia* spp. (grubs), *Ataenius spretulus* (Black Turfgrass Ataenius), *Atomaria linearis* (pygmy mangold beetle), *Aulacophore* spp., *Bothynoderes punctiventris* (beet root weevil), *Bruchus* spp. (weevils), *Bruchus pisorum* (pea weevil), *Cacoesia* spp., *Callosobruchus maculatus* (southern cow pea weevil), *Carpophilus hemipteras* (dried fruit beetle),

*Cassida vittata, Cerosterna* spp, *Cerotoma* spp. (chrysomeids), *Cerotoma trifurcata* (bean leaf beetle), *Ceutorhynchus* spp. (weevils), *Ceutorhynchus assimilis* (cabbage seedpod weevil), *Ceutorhynchus napi* (cabbage curculio), *Chaetocnema* spp. (chrysomelids), *Colaspis* spp. (soil beetles), *Conoderus scalaris, Conoderus stigmosus, Conotrachelus nenuphar* (plum curculio), *Cotinus nitidis* (Green June beetle), *Crioceris asparagi* (asparagus beetle), *Cryptolestes ferrugineus* (rusty grain beetle), *Cryptolestes pusillus* (flat grain beetle), *Cryptolestes turcicus* (Turkish grain beetle), *Ctenicera* spp. (wireworms), *Curculio* spp. (weevils), *Cyclocephala* spp. (grubs), *Cylindrocpturus adspersus* (sunflower stem weevil), *Deporaus marginatus* (mango leaf-cutting weevil), *Dermestes lardarius* (larder beetle), *Dermestes maculates* (hide beetle), *Diabrotica* spp. (chrysolemids), *Epilachna varivestis* (Mexican bean beetle), *Faustinus cubae, Hylobius pales* (pales weevil), *Hypera* spp. (weevils), *Hypera postica* (alfalfa weevil), *Hyperdoes* spp. (Hyperodes weevil), *Hypothenemus hampei* (coffee berry beetle), *Ips* spp. (engravers), *Lasioderma serricorne* (cigarette beetle), *Leptinotarsa decemlineata* (Colorado potato beetle), *Liogenys fuscus, Liogenys suturalis, Lissorhoptrus oryzophilus* (rice water weevil), *Lyctus* spp. (wood beetles/powder post beetles), *Maecolaspis joliveti, Megascelis* spp., *Melanotus communis, Meligethes* spp., *Meligethes aeneus* (blossom beetle), *Melolontha melolontha* (common European cockchafer), *Oberea brevis, Oberea linearis, Oryctes rhinoceros* (date palm beetle), *Oryzaephilus mercator* (merchant grain beetle), *Oryzaephilus surinamensis* (sawtoothed grain beetle), *Otiorhynchus* spp. (weevils), *Oulema melanopus* (cereal leaf beetle), *Oulema oryzae, Pantomorus* spp. (weevils), *Phyllophaga* spp. (May/June beetle), *Phyllophaga cuyabana, Phyllotreta* spp. (chrysomelids), *Phynchites* spp., *Popillia japonica* (Japanese beetle), *Prostephanus truncates* (larger grain borer), *Rhizopertha dominica* (lesser grain borer), *Rhizotrogus* spp. (European chafer), *Rhynchophorus* spp. (weevils), *Scolytus* spp. (wood beetles), *Shenophorus* spp. (Billbug), *Sitona lineatus* (pea leaf weevil), *Sitophilus* spp. (grain weevils), *Sitophilus granaries* (granary weevil), *Sitophilus oryzae* (rice weevil), *Stegobium paniceum* (drugstore beetle), *Tribolium* spp. (flour beetles), *Tribolium castaneum* (red flour beetle), *Tribolium confusum* (confused flour beetle), *Trogoderma variabile* (warehouse beetle), and *Zabrus tenebioides*.

In another embodiment, the invention disclosed in this document can be used to control Dermaptera (earwigs).

In another embodiment, the invention disclosed in this document can be used to control Dictyoptera (cockroaches). A non-exhaustive list of these pests includes, but is not limited to, *Blattella germanica* (German cockroach), *Blatta orientalis* (oriental cockroach), *Parcoblatta pennylvanica, Periplaneta americana* (American cockroach), *Periplaneta australoasiae* (Australian cockroach), *Periplaneta brunnea* (brown cockroach), *Periplaneta fuliginosa* (smokybrown cockroach), *Pyncoselus suninamensis* (Surinam cockroach), and *Supella longipalpa* (brownbanded cockroach).

In another embodiment, the invention disclosed in this document can be used to control Diptera (true flies). A non-exhaustive list of these pests includes, but is not limited to, *Aedes* spp. (mosquitoes), *Agromyza frontella* (alfalfa blotch leafminer), *Agromyza* spp. (leaf miner flies), *Anastrepha* spp. (fruit flies), *Anastrepha suspensa* (Caribbean fruit fly), *Anopheles* spp. (mosquitoes), *Batrocera* spp. (fruit flies), *Bactrocera cucurbitae* (melon fly), *Bactrocera dorsalis* (oriental fruit fly), *Ceratitis* spp. (fruit flies), *Ceratitis capitata* (Mediterranea fruit fly), *Chrysops* spp. (deer flies), *Cochliomyia* spp. (screwworms), *Contarinia* spp. (Gall midges), *Culex* spp. (mosquitoes), *Dasineura* spp. (gall midges), *Dasineura brassicae* (cabbage gall midge), *Delia* spp., *Delia platura* (seedcorn maggot), *Drosophila* spp. (vinegar flies), *Fannia* spp. (filth flies), *Fannia canicularis* (little house fly), *Fannia scalaris* (latrine fly), *Gasterophilus intestinalis* (horse bot fly), *Gracillia perseae, Haematobia irritans* (horn fly), *Hylemyia* spp. (root maggots), *Hypoderma lineatum* (common cattle grub), *Liriomyza* spp. (leafminer flies), *Liriomyza brassica* (serpentine leafminer), *Melophagus ovinus* (sheep ked), *Musca* spp. (muscid flies), *Musca autumnalis* (face fly), *Musca domestica* (house fly), *Oestrus ovis* (sheep bot fly), *Oscinella frit* (frit fly), *Pegomyia betae* (beet leafminer), *Phorbia* spp., *Psila rosae* (carrot rust fly), *Rhagoletis cerasi* (cherry fruit fly), *Rhagoletis pomonella* (apple maggot), *Sitodiplosis mosellana* (orange wheat blossom midge), *Stomoxys calcitrans* (stable fly), *Tabanus* spp. (horse flies), and *Tipula* spp. (crane flies).

In another embodiment, the invention disclosed in this document can be used to control Hemiptera (true bugs). A non-exhaustive list of these pests includes, but is not limited to, *Acrosternum hilare* (green stink bug), *Blissus leucopterus* (chinch bug), *Calocoris norvegicus* (potato mirid), *Cimex hemipterus* (tropical bed bug), *Cimex lectularius* (bed bug), *Dagbertus fasciatus, Dichelops furcatus, Dysdercus suturellus* (cotton stainer), *Edessa meditabunda, Eurygaster maura* (cereal bug), *Euschistus heros, Euschistus servus* (brown stink bug), *Helopeltis antonii, Helopeltis theivora* (tea blight plantbug), *Lagynotomus* spp. (stink bugs), *Leptocorisa oratorius, Leptocorisa varicornis, Lygus* spp. (plant bugs), *Lygus hesperus* (western tarnished plant bug), *Maconellicoccus hirsutus, Neurocolpus longirostris, Nezara viridula* (southern green stink bug), *Phytocoris* spp. (plant bugs), *Phytocoris californicus, Phytocoris relativus, Piezodorus guildingi, Poecilocapsus lineatus* (fourlined plant bug), *Psallus vaccinicola, Pseudacysta perseae, Scaptocoris castanea*, and *Triatoma* spp. (bloodsucking conenose bugs/kissing bugs).

In another embodiment, the invention disclosed in this document can be used to control Homoptera (aphids, scales, whiteflies, leafhoppers). A non-exhaustive list of these pests includes, but is not limited to, *Acrythosiphon pisum* (pea aphid), *Adelges* spp. (adelgids), *Aleurodes proletella* (cabbage whitefly), *Aleurodicus disperses, Aleurothrixus floccosus* (woolly whitefly), *Aluacaspis* spp., *Amrasca bigutella bigutella, Aphrophora* spp. (leafhoppers), *Aonidiella aurantii* (California red scale), *Aphis* spp. (aphids), *Aphis gossypii* (cotton aphid), *Aphis pomi* (apple aphid), *Aulacorthum solani* (foxglove aphid), *Bemisia* spp. (whiteflies), *Bemisia argentifolii, Bemisia tabaci* (sweetpotato whitefly), *Brachycolus noxius* (Russian aphid), *Brachycorynella asparagi* (asparagus aphid), *Brevennia rehi, Brevicoryne brassicae* (cabbage aphid), *Ceroplastes* spp. (scales), *Ceroplastes rubens* (red wax scale), *Chionaspis* spp. (scales), *Chrysomphalus* spp. (scales), *Coccus* spp. (scales), *Dysaphis plantaginea* (rosy apple aphid), *Empoasca* spp. (leafhoppers), *Eriosoma lanigerum* (woolly apple aphid), *Icerya purchasi* (cottony cushion scale), *Idioscopus nitidulus* (mango leafhopper), *Laodelphax striatellus* (smaller brown planthopper), *Lepidosaphes* spp., *Macrosiphum* spp., *Macrosiphum euphorbiae* (potato aphid), *Macrosiphum granarium* (English grain aphid), *Macrosiphum rosae* (rose aphid), *Macrosteles quadrilineatus* (aster leafhopper), *Mahanarva frimbiolata, Metopolophium dirhodum* (rose grain aphid), *Mictis longicornis, Myzus persicae* (green peach aphid), *Nephotettix* spp. (leafhoppers), *Nephotettix cinctipes* (green leafhopper), *Nilaparvata lugens* (brown planthopper), *Parlatoria pergandii* (chaff scale), *Parlatoria ziziphi* (ebony scale), *Peregrinus maidis* (corn delphacid), *Philaenus* spp. (spittlebugs), *Phylloxera vitifoliae*

(grape phylloxera), *Physokermes piceae* (spruce bud scale), *Planococcus* spp. (mealybugs), *Pseudococcus* spp. (mealybugs), *Pseudococcus brevipes* (pine apple mealybug), *Quadraspidiotus perniciosus* (San Jose scale), *Rhapalosiphum* spp. (aphids), *Rhapalosiphum maida* (corn leaf aphid), *Rhapalosiphum padi* (oat bird-cherry aphid), *Saissetia* spp. (scales), *Saissetia oleae* (black scale), *Schizaphis graminum* (greenbug), *Sitobion avenae* (English grain aphid), *Sogatella furcifera* (white-backed planthopper), *Therioaphis* spp. (aphids), *Toumeyella* spp. (scales), *Toxoptera* spp. (aphids), *Trialeurodes* spp. (whiteflies), *Trialeurodes vaporariorum* (greenhouse whitefly), *Trialeurodes abutiloneus* (bandedwing whitefly), *Unaspis* spp. (scales), *Unaspis yanonensis* (arrowhead scale), and *Zulia entreriana*.

In another embodiment, the invention disclosed in this document can be used to control Hymenoptera (ants, wasps, and bees). A non-exhaustive list of these pests includes, but is not limited to, *Acromyrrmex* spp., *Athalia rosae, Atta* spp. (leafcutting ants), *Camponotus* spp. (carpenter ants), *Diprion* spp. (sawflies), *Formica* spp. (ants), *Iridomyrmex humilis* (Argentine ant), *Monomorium* ssp., *Monomorium minumum* (little black ant), *Monomorium pharaonis* (Pharaoh ant), *Neodiprion* spp. (sawflies), *Pogonomyrmex* spp. (harvester ants), *Polistes* spp. (paper wasps), *Solenopsis* spp. (fire ants), *Tapoinoma sessile* (odorous house ant), *Tetranomorium* spp. (pavement ants), *Vespula* spp. (yellow jackets), and *Xylocopa* spp. (carpenter bees).

In another embodiment, the invention disclosed in this document can be used to control Isoptera (termites). A non-exhaustive list of these pests includes, but is not limited to, *Coptotermes* spp., *Coptotermes curvignathus, Coptotermes frenchii, Coptotermes formosanus* (Formosan subterranean termite), *Cornitermes* spp. (nasute termites), *Cryptotermes* spp. (drywood termites), *Heterotermes* spp. (desert subterranean termites), *Heterotermes aureus, Kalotermes* spp. (drywood termites), *Incistitermes* spp. (drywood termites), *Macrotermes* spp. (fungus growing termites), *Marginitermes* spp. (drywood termites), *Microcerotermes* spp. (harvester termites), *Microtermes obesi, Procornitermes* spp., *Reticulitermes* spp. (subterranean termites), *Reticulitermes banyulensis, Reticulitermes grassei, Reticulitermes flavipes* (eastern subterranean termite), *Reticulitermes hageni, Reticulitermes hesperus* (western subterranean termite), *Reticulitermes santonensis, Reticulitermes speratus, Reticulitermes tibialis, Reticulitermes virginicus, Schedorhinotermes* spp., and *Zootermopsis* spp. (rotten-wood termites).

In another embodiment, the invention disclosed in this document can be used to control Lepidoptera (moths and butterflies). A non-exhaustive list of these pests includes, but is not limited to, *Achoea janata, Adoxophyes* spp., *Adoxophyes orana, Agrotis* spp. (cutworms), *Agrotis ipsilon* (black cutworm), *Alabama argillacea* (cotton leafworm), *Amorbia cuneana, Amyelosis transitella* (navel orangeworm), *Anacamptodes defectaria, Anarsia lineatella* (peach twig borer), *Anomis sabulifera* (jute looper), *Anticarsia gemmatalis* (velvetbean caterpillar), *Archips argyrospila* (fruittree leafroller), *Archips rosana* (rose leaf roller), *Argyrotaenia* spp. (tortricid moths), *Argyrotaenia citrana* (orange tortrix), *Autographa gamma, Bonagota cranaodes, Borbo cinnara* (rice leaf folder), *Bucculatrix thurberiella* (cotton leafperforator), *Caloptilia* spp. (leaf miners), *Capua reticulana, Carposina niponensis* (peach fruit moth), *Chilo* spp., *Chlumetia transversa* (mango shoot borer), *Choristoneura rosaceana* (oblique banded leafroller), *Chrysodeixis* spp., *Cnaphalocerus medinalis* (grass leafroller), *Colias* spp., *Conpomorpha cramerella, Cossus cossus* (carpenter moth), *Crambus* spp. (Sod webworms), *Cydia funebrana* (plum fruit moth), *Cydia molesta* (oriental fruit moth), *Cydia nignicana* (pea moth), *Cydia pomonella* (codling moth), *Darna diducta, Diaphania* spp. (stem borers), *Diatraea* spp. (stalk borers), *Diatraea saccharalis* (sugarcane borer), *Diatraea graniosella* (southwester corn borer), *Earias* spp. (bollworms), *Earias insulata* (Egyptian bollworm), *Earias vitella* (rough northern bollworm), *Ecdytopopha aurantianum, Elasmopalpus lignosellus* (lesser cornstalk borer), *Epiphysias postruttana* (light brown apple moth), *Ephestia* spp. (flour moths), *Ephestia cautella* (almond moth), *Ephestia elutella* (tobbaco moth), *Ephestia kuehniella* (Mediterranean flour moth), *Epimeces* spp., *Epinotia aporema, Erionota thrax* (banana skipper), *Eupoecilia ambiguella* (grape berry moth), *Euxoa auxiliaris* (army cutworm), *Feltia* spp. (cutworms), *Gortyna* spp. (stemborers), *Grapholita molesta* (oriental fruit moth), *Hedylepta indicata* (bean leaf webber), *Helicoverpa* spp. (noctuid moths), *Helicoverpa armigera* (cotton bollworm), *Helicoverpa zea* (bollworm/corn earworm), *Heliothis* spp. (noctuid moths), *Heliothis virescens* (tobacco budworm), Hellula undalis (cabbage webworm), *Indarbela* spp. (root borers), *Keiferia lycopersicella* (tomato pinworm), *Leucinodes orbonalis* (eggplant fruit borer), *Leucoptera malifoliella, Lithocollectis* spp., *Lobesia botrana* (grape fruit moth), *Loxagrotis* spp. (noctuid moths), *Loxagrotis albicosta* (western bean cutworm), *Lymantria dispar* (gypsy moth), *Lyonetia clerkella* (apple leaf miner), *Mahasena corbetti* (oil palm bagworm), *Malacosoma* spp. (tent caterpillars), *Mamestra brassicae* (cabbage armyworm), *Maruca testulalis* (bean pod borer), *Metisa plana* (bagworm), *Mythimna unipuncta* (true armyworm), *Neoleucinodes elegantalis* (small tomato borer), *Nymphula depunctalis* (rice caseworm), *Operophthera brumata* (winter moth), *Ostrinia nubilalis* (European corn borer), *Oxydia vesulia, Pandemis cerasana* (common currant tortrix), *Pandemis heparana* (brown apple tortrix), *Papilio demodocus, Pectinophora gossypiella* (pink bollworm), *Peridroma* spp. (cutworms), *Peridroma saucia* (variegated cutworm), *Perileucoptera coffeella* (white coffee leafminer), *Phthorimaea operculella* (potato tuber moth), *Phyllocnisitis citrella, Phyllonorycter* spp. (leafminers), *Pieris rapae* (imported cabbageworm), *Plathypena scabra, Plodia interpunctella* (Indian meal moth), *Plutella xylostella* (diamondback moth), *Polychrosis viteana* (grape berry moth), *Prays endocarpa, Prays oleae* (olive moth), *Pseudaletia* spp. (noctuid moths), *Pseudaletia unipunctata* (armyworm), *Pseudoplusia includens* (soybean looper), *Rachiplusia nu, Scirpophaga incertulas, Sesamia* spp. (stemborers), *Sesamia inferens* (pink rice stem borer), *Sesamia nonagrioides, Setora nitens, Sitotroga cerealella* (Angoumois grain moth), *Sparganothis pilleriana, Spodoptera* spp. (armyworms), *Spodoptera exigua* (beet armyworm), *Spodoptera fugiperda* (fall armyworm), *Spodoptera oridania* (southern armyworm), *Synanthedon* spp. (root borers), *Thecla basilides, Thermisia gemmatalis, Tineola bisselliella* (webbing clothes moth), *Trichoplusia ni* (cabbage looper), *Tuta absoluta, Yponomeuta* spp., *Zeuzera coffeae* (red branch borer), and *Zeuzera pyrina* (leopard moth).

In another embodiment, the invention disclosed in this document can be used to control *Mallophaga* (chewing lice). A non-exhaustive list of these pests includes, but is not limited to, *Bovicola ovis* (sheep biting louse), *Menacanthus stramineus* (chicken body louse), and *Menopon gallinea* (common hen house).

In another embodiment, the invention disclosed in this document can be used to control Orthoptera (grasshoppers, locusts, and crickets). A non-exhaustive list of these pests includes, but is not limited to, *Anabrus simplex* (Mormon cricket), *Gryllotalpidae* (mole crickets), *Locusta migratoria*,

*Melanoplus* spp. (grasshoppers), *Microcentrum retinerve* (angular winged katydid), *Pterophylla* spp. (kaydids), *chistocerca gregaria, Scudderia furcata* (forktailed bush katydid), and *Valanga nigricorni.*

In another embodiment, the invention disclosed in this document can be used to control Phthiraptera (sucking lice). A non-exhaustive list of these pests includes, but is not limited to, *Haematopinus* spp. (cattle and hog lice), *Linognathus ovillus* (sheep louse), *Pediculus humanus* capitis (human body louse), *Pediculus humanus* humanus (human body lice), and *Pthirus pubis* (crab louse), In another embodiment, the invention disclosed in this document can be used to control Siphonaptera (fleas). A non-exhaustive list of these pests includes, but is not limited to, *Ctenocephalides canis* (dog flea), *Ctenocephalides felis* (cat flea), and *Pulex irritans* (human flea).

In another embodiment, the invention disclosed in this document can be used to control Thysanoptera (thrips). A non-exhaustive list of these pests includes, but is not limited to, *Frankliniella fusca* (tobacco thrips), *Frankliniella occidentalis* (western flower thrips), *Frankliniella shultzei* Frankliniella williamsi (corn thrips), *Heliothrips haemorrhaidalis* (greenhouse thrips), *Riphiphorothrips cruentatus, Scirtothrips* spp., *Scirtothrips citri* (citrus thrips), *Scirtothrips dorsalis* (yellow tea thrips), *Taeniothrips rhopalantennalis*, and *Thrips* spp.

In another embodiment, the invention disclosed in this document can be used to control Thysanura (bristletails). A non-exhaustive list of these pests includes, but is not limited to, *Lepisma* spp. (silverfish) and *Thermobia* spp. (firebrats).

In another embodiment, the invention disclosed in this document can be used to control Acarina (mites and ticks). A non-exhaustive list of these pests includes, but is not limited to, *Acarapsis woodi* (tracheal mite of honeybees), *Acarus* spp. (food mites), *Acarus siro* (grain mite), *Aceria mangiferae* (mango bud mite), *Aculops* spp., *Aculops lycopersici* (tomato russet mite), *Aculops pelekasi, Aculus pelekassi, Aculus schlechtendali* (apple rust mite), *Amblyomma americanum* (lone star tick), *Boophilus* spp. (ticks), *Brevipalpus obovatus* (privet mite), *Brevipalpus phoenicis* (red and black flat mite), *Demodex* spp. (mange mites), *Dermacentor* spp. (hard ticks), *Dermacentor variabilis* (american dog tick), *Dermatophagoides pteronyssinus* (house dust mite), *Eotetranycus* spp., *Eotetranychus carpini* (yellow spider mite), *Epitimerus* spp., *Eriophyes* spp., *Ixodes* spp. (ticks), *Metatetranycus* spp., *Notoedres cati, Oligonychus* spp., *Oligonychus coffee, Oligonychus ilicus* (southern red mite), *Panonychus* spp., *Panonychus citri* (citrus red mite), *Panonychus ulmi* (European red mite), *Phyllocoptruta oleivora* (citrus rust mite), *Polyphagotarsonemun latus* (broad mite), *Rhipicephalus sanguineus* (brown dog tick), *Rhizoglyphus* spp. (bulb mites), *Sarcoptes scabiei* (itch mite), *Tegolophus perseaflorae, Tetranychus* spp., *Tetranychus urticae* (twospotted spider mite), and *Varroa destructor* (honey bee mite).

In another embodiment, the invention disclosed in this document can be used to control Nematoda (nematodes). A non-exhaustive list of these pests includes, but is not limited to, *Aphelenchoides* spp. (bud and leaf & pine wood nematodes), *Belonolaimus* spp. (sting nematodes), *Criconemella* spp. (ring nematodes), Dirofilaria immitis (dog heartworm), *Ditylenchus* spp. (stem and bulb nematodes), *Heterodera* spp. (cyst nematodes), *Heterodera zeae* (corn cyst nematode), *Hirschmanniella* spp. (root nematodes), *Hoplolaimus* spp. (lance nematodes), *Meloidogyne* spp. (root knot nematodes), *Meloidogyne incognita* (root knot nematode), *Onchocerca volvulus* (hook-tail worm), *Pratylenchus* spp. (lesion nematodes), *Radopholus* spp. (burrowing nematodes), and *Rotylenchus reniformis* (kidney-shaped nematode).

In another embodiment, the invention disclosed in this document can be used to control Symphyla (symphylans). A non-exhaustive list of these pests includes, but is not limited to, *Scutigerella immaculata*.

For more detailed information consult "Handbook of Pest Control—The Behavior, Life History, and Control of Household Pests" by Arnold Mattis, 9th Edition, copyright 2004 by GIE Media Inc.

Mixtures

Some of the pesticides that can be employed beneficially in combination with the invention disclosed in this document include, but are not limited to the following:

1,2 dichloropropane, 1,3 dichloropropene, abamectin, acephate, acequinocyl, acetamiprid, acethion, acetoprole, acrinathrin, acrylonitrile, alanycarb, aldicarb, aldoxycarb, aldrin, allethrin, allosamidin, allyxycarb, alpha-cypermethrin, alpha-ecdysone, alpha-endosulfan AKD-1022, amidithion, amidoflumet, aminocarb, amiton, amitraz, anabasine, arsenous oxide, athidathion, azadirachtin, azamethiphos, azinphos ethyl, azinphos methyl, azobenzene, azocyclotin, azothoate,

*Bacillus thuringiensis*, barium hexafluorosilicate, barthrin, benclothiaz, bendiocarb, benfuracarb, benomyl, benoxafos, bensultap, benzoximate, benzyl benzoate, beta-cyfluthrin, beta-cypermethrin, bifenazate, bifenthrin, binapacryl, bioallethrin, bioethanomethrin, biopermethrin, bistrifluoron, borax, boric acid, bromfenvinfos, bromo DDT, bromocyclen, bromophos, bromophos ethyl, bromopropylate, bufencarb, buprofezin, butacarb, butathiofos, butocarboxim, butonate, butoxycarboxim, cadusafos, calcium arsenate, calcium polysulfide, camphechlor, carbanolate, carbaryl, carbofuran, carbon disulfide, carbon tetrachloride, carbophenothion, carbosulfan, cartap, chinomethionat, chlorantraniliprole, chlorbenside, chlorbicyclen, chlordane, chlordecone, chlordimeform, chlorethoxyfos, chlorfenapyr, chlorfenethol, chlorfenson, chlorfensulphide, chlorfenvinphos, chlorfluazuron, chlormephos, chlorobenzilate, 3-(4-chloro-2,6-diemthylphenyl)-4-hydroxy-8-oxa-1-azaspiro[4,5]dec-3-en-2-one, 3-(4'-chloro-2,4-dimethyl[1,1'-biphenyl]-3-yl)-4-hydroxy-8-oxa-1-azaspiro[4,5]dec-3-en-2-one, 4-[[(6-chloro-3-pyridinyl)methyl]methylamino]-2(5H)-furanone, 4-[[(6-chloro-3-pyridinyl)methyl]cyclopropylamino]-2(5H)-furanone, 3-chloro-N2-[(1S)-1-methyl-2-(methylsulfonyl)ethyl]-N1-[2-methyl-4-[1,2,2,2-tetrafluoro-1-(trifluoromethyl)ethyl]phenyl]-1,2-benzenedicarboxamide, chloroform, chloromebuform, chloromethiuron, chloropicrin, chloropropylate, chlorphoxim, chlorprazophos, chlorpyrifos, chlorpyrifos-methyl, chlorthiophos, chromafenozide, cinerin I, cinerin II, cis-methrin, cloethocarb, clofentezine, closantel, clothianidin, copper acetoarsenite, copper arsenate, copper naphthenate, copper oleate, coumaphos, coumithoate, crotamiton, crotoxyphos, cruentaren A &B, crufomate, cryolite, cyanofenphos, cyanophos, cyanthoate, cyanthraniliprole, cyclethrin, cycloprothrin, cyenopyrafen, cyflumetofen, cyfluthrin, cyhalothrin, cyhexatin, cypermethrin, cyphenothrin, cyromazine, cythioate, 2-cyano-N-ethyl-4-fluoro-3-methoxy-benenesulfonamide, 2-cyano-N-ethyl-3-methoxy-benzenesulfonamide, 2-cyano-3-difluoromethoxy-N-ethyl-4-fluoro-benzenesulfonamide, 2-cyano-3-fluoromethoxy-N-ethyl-benzenesulfonamide, 2-cyano-6-fluoro-3-methoxy-N,N-dimethyl-benzenesulfonamide, 2-cyano-N-ethyl-6-fluoro-3-methoxy-N-methyl-benzenesulfonamide, 2-cyano-3-difluoromethoxy-N,N-diemthyl-benzenesulfonamide.

d-limonene, dazomet, DBCP, DCIP, DDT, decarbofuran, deltamethrin, demephion, demephion O, demephion S, demeton, demeton methyl, demeton O, demeton O methyl, demeton S, demeton S methyl, demeton S methylsulphon, diafenthiuron, dialifos, diamidafos, diazinon, dicapthon, dichlofenthion, dichlofluanid, dichlorvos, dicofol, dicresyl, dicrotophos, dicyclanil, dieldrin, dienochlor, diflovidazin, diflubenzuron, 3-(difluoromethyl)-N-[2-(3,3-dimethylbutyl)phenyl]-1-methyl-1H-pyrazole-4-carboxamide dilor, dimefluthrin, dimefox, dimetan, dimethoate, dimethrin, dimethylvinphos, dimetilan, dinex, dinobuton, dinocap, dinocap 4, dinocap 6, dinocton, dinopenton, dinoprop, dinosam, dinosulfon, dinotefuran, dinoterbon, diofenolan, dioxabenzofos, dioxacarb, dioxathion, diphenyl sulfone, disulfuram, disulfoton, dithicrofos, DNOC, dofenapyn, doramectin, ecdysterone, emamectin, EMPC, empenthrin, endosulfan, endothion, endrin, EPN, epofenonane, eprinomectin, esfenvalerate, etaphos, ethiofencarb, ethion, ethiprole, ethoate methyl, ethoprophos, ethyl DDD, ethyl formate, ethylene dibromide, ethylene dichloride, ethylene oxide, etofenprox, etoxazole, etrimfos, EXD, F1050,famphur, fenamiphos, fenazaflor, fenazaquin, fenbutatin oxide, fenchlorphos, fenethacarb, fenfluthrin, fenitrothion, fenobucarb, fenothiocarb, fenoxacrim, fenoxycarb, fenpirithrin, fenpropathrin, fenpyroximate, fenson, fensulfothion, fenthion, fenthion ethyl, fentrifanil, fenvalerate, fipronil, FKI-1033, flonicamid, fluacrypyrim, fluazuron, flubendiamide, flubenzimine, flucofuron, flucycloxuron, flucythrinate, fluenetil, flufenerim, flufenoxuron, flufenprox, flumethrin, fluorbenside, fluvalinate, fonofos, formetanate, formothion, formparanate, fosmethilan, fospirate, fosthiazate, fosthietan, fosthietan, furathiocarb, furethrin, furfural, Gamma-cyhalothrin, gamma-HCH, halfenprox, halofenozide, HCH, HEOD, heptachlor, heptenophos, heterophos, hexaflumuron, hexythiazox, HHDN, hydramethylnon, hydrogen cyanide, hydroprene, hyquincarb, imicyafos, imidacloprid, imiprothrin, indoxacarb, iodomethane, IPSP, isamidofos, isazofos, isobenzan, isocarbophos, isodrin, isofenphos, isoprocarb, isoprothiolane, isothioate, isoxathion, ivermectin, jasmolin I, jasmolin II, jodfenphos, juvenile hormone I, juvenile hormone II, juvenile hormone III, JS118, kelevan, kinoprene, lambda-cyhalothrin, lead arsenate, lepimectin, leptophos, lindane, lirimfos, lufenuron, lythidathion, malathion, malonoben, mazidox, mecarbam, mecarphon, menazon, mephosfolan, mercurous chloride, mesulfen, mesulfenfos, metaflumizone, metam, methacrifos, methamidophos, methidathion, methiocarb, methocrotophos, methomyl, methoprene, methoxychlor, methoxyfenozide, methyl bromide, methyl isothiocyanate, methylchloroform, methylene chloride, metofluthrin, metolcarb, metoxadiazone, mevinphos, mexacarbate, milbemectin, milbemycin oxime, mipafox, mirex, MNAF, monocrotophos, morphothion, moxidectin, naftalofos, naled, naphthalene, N-ethyl-2,2-dimethylpropionamide-2-(2,6-dichloro-α,α,α-thrifluoro-p-tolyl) hydrazone, N-ethyl-2,2-dichloro-1-methylcyclopropane-carboxamide-2-(2,6-dichloro-α,α,α-thrifluoro-p-tolyl) hydrazone, nicotine, nifluridide, nikkomycins, nitenpyram, nithiazine, nitrilacarb, novaluron, noviflumuron, omethoate, oxamyl, oxydemeton methyl, oxydeprofos, oxydisulfoton, paradichlorobenzene, parathion, parathion methyl, penfluoron, pentachlorophenol, permethrin, phenkapton, phenothrin, phenthoate, phorate, phosalone, phosfolan, phosmet, phosnichlor, phosphamidon, phosphine, phosphocarb, phoxim, phoxim methyl, pirimetaphos, pirimicarb, pirimiphos ethyl, pirimiphos methyl, potassium arsenite, potassium thiocyanate, pp' DDT, prallethrin, precocene I, precocene II, precocene III, primidophos, proclonol, profenofos, profluthrin, promacyl, promecarb, propaphos, propargite, propetamphos, propoxur, prothidathion, prothiofos, prothoate, protrifenbute, pyraclofos, pyrafluprole, pyrazophos, pyresmethrin, pyrethrin I, pyrethrin II, pyridaben, pyridalyl, pyridaphenthion, pyrifluquinazon, pyrimidifen, pyrimitate, pyriprole, pyriproxyfen, Qcide, quassia, quinalphos, quinalphos, quinalphos methyl, quinothion, quantifies, rafoxanide, resmethrin, rotenone, ryania, sabadilla, schradan, selamectin, silafluofen, sodium arsenite, sodium fluoride, sodium hexafluorosilicate, sodium thiocyanate, sophamide, spinetoram, spinosad, spirodiclofen, spiromesifen, spirotetramat, sulcofuron, sulfuram, sulfluramid, sulfotep, sulfoxaflor, sulfur, sulfuryl fluoride, sulprofos, tau-fluvalinate, tazimcarb, TDE, tebufenozide, tebufenpyrad, tebupirimfos, teflubenzuron, tefluthrin, temephos, TEPP, terallethrin, terbufos, tetrachloroethane, tetrachlorvinphos, tetradifon, tetramethrin, tetranactin, tetrasul, theta cypermethrin, thiacloprid, thiamethoxam, thicrofos, thiocarboxime, thiocyclam, thiodicarb, thiofanox, thiometon, thionazin, thioquinox, thiosultap, thuringiensin, tolfenpyrad, tralomethrin, transfluthrin, transpermethrin, triarathene, triazamate, triazophos, trichlorfon, trichlormetaphos 3, trichloronat, trifenofos, triflumuron, trimethacarb, triprene, vamidothion, vamidothion, vaniliprole, vaniliprole, XDE-208, XMC, xylylcarb, Zeta-cypermethrin and zolaprofos.

Additionally, any combination of the above pesticides can be used.

The invention disclosed in this document can also be used with herbicides and fungicides, both for reasons of economy and synergy.

The invention disclosed in this document can be used with antimicrobials, bactericides, defoliants, safeners, synergists, algaecides, attractants, desiccants, pheromones, repellants, animal dips, avicides, disinfectants, semiochemicals, and molluscicides (these categories not necessarily mutually exclusive) for reasons of economy, and synergy.

For more information consult "Compendium of Pesticide Common Names" located at http://www.alanwood.net/pesticides/index.html as of the filing date of this document. Also consult "The Pesticide Manual" 14$^{th}$ Edition, edited by C D S Tomlin, copyright 2006 by British Crop Production Council.

Synergistic Mixtures

The invention disclosed in this document can be used with other compounds such as the ones mentioned under the heading "Mixtures" to form synergistic mixtures where the mode of action of the compounds in the mixtures are the same, similar, or different.

Examples of mode of actions include, but are not limited to: acetyl choline esterase inhibitor; sodium channel modulator; chitin biosynthesis inhibitor; GABA-gated chloride channel antagonist; GABA and glutamate-gated chloride channel agonist; acetyl choline receptor agonist; MET I inhibitor; Mg-stimulated ATPase inhibitor; nicotinic acetylcholine receptor; Midgut membrane disrupter; and oxidative phosphorylation disrupter.

Additionally, the following compounds are known as synergists and can be used with the invention disclosed in this document: piperonyl butoxide, piprotal, propyl isome, sesamex, sesamolin, and sulfoxide.

Formulations

A pesticide is rarely suitable for application in its pure form. It is usually necessary to add other substances so that the pesticide can be used at the required concentration and in an appropriate form, permitting ease of application, handling, transportation, storage, and maximum pesticide activity. Thus, pesticides are formulated into, for example, baits, concentrated emulsions, dusts, emulsifiable concentrates, fumigants, gels, granules, microencapsulations, seed treatments, suspension concentrates, suspoemulsions, tablets, water soluble liquids, water dispersible granules or dry flowables, wettable powders, and ultra low volume solutions.

For further information on formulation types see "Catalogue of pesticide formulation types and international coding system" Technical Monograph n° 2, 5th Edition by CropLife International (2002).

Pesticides are applied most often as aqueous suspensions or emulsions prepared from concentrated formulations of such pesticides. Such water-soluble, water-suspendable, or emulsifiable formulations, are either solids, usually known as wettable powders, or water dispersible granules, or liquids usually known as emulsifiable concentrates, or aqueous suspensions. Wettable powders, which may be compacted to form water dispersible granules, comprise an intimate mixture of the pesticide, a carrier, and surfactants. The concentration of the pesticide is usually from about 10% to about 90% by weight. The carrier is usually chosen from among the attapulgite clays, the montmorillonite clays, the diatomaceous earths, or the purified silicates. Effective surfactants, comprising from about 0.5% to about 10% of the wettable powder, are found among sulfonated lignins, condensed naphthalenesulfonates, naphthalenesulfonates, alkylbenzenesulfonates, alkyl sulfates, and nonionic surfactants such as ethylene oxide adducts of alkyl phenols.

Emulsifiable concentrates of pesticides comprise a convenient concentration of a pesticide, such as from about 50 to about 500 grams per liter of liquid dissolved in a carrier that is either a water miscible solvent or a mixture of water-immiscible organic solvent and emulsifiers. Useful organic solvents include aromatics, especially xylenes and petroleum fractions, especially the high-boiling naphthalenic and olefinic portions of petroleum such as heavy aromatic naphtha. Other organic solvents may also be used, such as the terpenic solvents including rosin derivatives, aliphatic ketones such as cyclohexanone, and complex alcohols such as 2-ethoxyethanol. Suitable emulsifiers for emulsifiable concentrates are chosen from conventional anionic and nonionic surfactants.

Aqueous suspensions comprise suspensions of water-insoluble pesticides dispersed in an aqueous carrier at a concentration in the range from about 5% to about 50% by weight. Suspensions are prepared by finely grinding the pesticide and vigorously mixing it into a carrier comprised of water and surfactants. Ingredients, such as inorganic salts and synthetic or natural gums, may also be added, to increase the density and viscosity of the aqueous carrier. It is often most effective to grind and mix the pesticide at the same time by preparing the aqueous mixture and homogenizing it in an implement such as a sand mill, ball mill, or piston-type homogenizer.

Pesticides may also be applied as granular compositions that are particularly useful for applications to the soil. Granular compositions usually contain from about 0.5% to about 10% by weight of the pesticide, dispersed in a carrier that comprises clay or a similar substance. Such compositions are usually prepared by dissolving the pesticide in a suitable solvent and applying it to a granular carrier which has been pre-formed to the appropriate particle size, in the range of from about 0.5 to 3 mm. Such compositions may also be formulated by making a dough or paste of the carrier and compound and crushing and drying to obtain the desired granular particle size.

Dusts containing a pesticide are prepared by intimately mixing the pesticide in powdered form with a suitable dusty agricultural carrier, such as kaolin clay, ground volcanic rock, and the like. Dusts can suitably contain from about 1% to about 10% of the pesticide. They can be applied as a seed dressing, or as a foliage application with a dust blower machine.

It is equally practical to apply a pesticide in the form of a solution in an appropriate organic solvent, usually petroleum oil, such as the spray oils, which are widely used in agricultural chemistry.

Pesticides can also be applied in the form of an aerosol composition. In such compositions the pesticide is dissolved or dispersed in a carrier, which is a pressure-generating propellant mixture. The aerosol composition is packaged in a container from which the mixture is dispensed through an atomizing valve.

Pesticide baits are formed when the pesticide is mixed with food or an attractant or both. When the pests eat the bait they also consume the pesticide. Baits may take the form of granules, gels, flowable powders, liquids, or solids. They are used in pest harborages.

Fumigants are pesticides that have a relatively high vapor pressure and hence can exist as a gas in sufficient concentrations to kill pests in soil or enclosed spaces. The toxicity of the fumigant is proportional to its concentration and the exposure time. They are characterized by a good capacity for diffusion and act by penetrating the pest's respiratory system or being absorbed through the pest's cuticle. Fumigants are applied to control stored product pests under gas proof sheets, in gas sealed rooms or buildings or in special chambers.

Pesticides can be microencapsulated by suspending the pesticide particles or droplets in plastic polymers of various types. By altering the chemistry of the polymer or by changing factors in the processing, microcapsules can be formed of various sizes, solubility, wall thicknesses, and degrees of penetrability. These factors govern the speed with which the active ingredient within is released, which. in turn, affects the residual performance, speed of action, and odor of the product.

Oil solution concentrates are made by dissolving pesticide in a solvent that will hold the pesticide in solution. Oil solutions of a pesticide usually provide faster knockdown and kill of pests than other formulations due to the solvents themselves having pesticidal action and the dissolution of the waxy covering of the integument increasing the speed of uptake of the pesticide. Other advantages of oil solutions include better storage stability, better penetration of crevices, and better adhesion to greasy surfaces.

Another embodiment is an oil-in-water emulsion, wherein the emulsion comprises oily globules which are each provided with a lamellar liquid crystal coating and are dispersed in an aqueous phase, wherein each oily globule comprises at least one compound which is agriculturally active, and is individually coated with a monolamellar or oligolamellar layer comprising: (1) at least one non-ionic lipophilic surface-active agent, (2) at least one non-ionic hydrophilic surface-active agent and (3) at least one ionic surface-active agent, wherein the globules having a mean particle diameter of less than 800 nanometers. Further information on the embodiment is disclosed in U.S. patent publication 20070027034 published Feb. 1, 2007, having patent application Ser. No. 11/495,228. For ease of use this embodiment will be referred to as "OIWE".

For further information consult "Insect Pest Management" 2nd Edition by D. Dent, copyright CAB International (2000). Additionally, for more detailed information consult "Handbook of Pest Control—The Behavior, Life History, and Control of Household Pests" by Arnold Mattis, 9th Edition, copyright 2004 by GIE Media Inc.

Other Formulation Components

Generally, the invention disclosed in this document when used in a formulation, such formulation can also contain other components. These components include, but are not limited to, (this is a non-exhaustive and non-mutually exclusive list) wetters, spreaders, stickers, penetrants, buffers, sequestering agents, drift reduction agents, compatibility agents, antifoam agents, cleaning agents, and emulsifiers. A few components are described forthwith.

A wetting agent is a substance that when added to a liquid increases the spreading or penetration power of the liquid by reducing the interfacial tension between the liquid and the surface on which it is spreading. Wetting agents are used for two main functions in agrochemical formulations: during processing and manufacture to increase the rate of wetting of powders in water to make concentrates for soluble liquids or suspension concentrates; and during mixing of a product with water in a spray tank to reduce the wetting time of wettable powders and to improve the penetration of water into water-dispersible granules. Examples of wetting agents used in wettable powder, suspension concentrate, and water-dispersible granule formulations are: sodium lauryl sulphate; sodium dioctyl sulphosuccinate; alkyl phenol ethoxylates; and aliphatic alcohol ethoxylates.

A dispersing agent is a substance which adsorbs onto the surface of a particles and helps to preserve the state of dispersion of the particles and prevents them from reaggregating. Dispersing agents are added to agrochemical formulations to facilitate dispersion and suspension during manufacture, and to ensure the particles redisperse into water in a spray tank. They are widely used in wettable powders, suspension concentrates and water-dispersible granules. Surfactants that are used as dispersing agents have the ability to adsorb strongly onto a particle surface and provide a charged or steric barrier to reaggregation of particles. The most commonly used surfactants are anionic, non-ionic, or mixtures of the two types. For wettable powder formulations, the most common dispersing agents are sodium lignosulphonates. For suspension concentrates, very good adsorption and stabilization are obtained using polyelectrolytes, such as sodium naphthalene sulphonate formaldehyde condensates. Tristyrylphenol ethoxylate phosphate esters are also used. Non-ionics such as alkylarylethylene oxide condensates and EO-PO block copolymers are sometimes combined with anionics as dispersing agents for suspension concentrates. In recent years, new types of very high molecular weight polymeric surfactants have been developed as dispersing agents. These have very long hydrophobic 'backbones' and a large number of ethylene oxide chains forming the 'teeth' of a 'comb' surfactant. These high molecular weight polymers can give very good long-term stability to suspension concentrates because the hydrophobic backbones have many anchoring points onto the particle surfaces. Examples of dispersing agents used in agrochemical formulations are: sodium lignosulphonates; sodium naphthalene sulphonate formaldehyde condensates; tristyrylphenol ethoxylate phosphate esters; aliphatic alcohol ethoxylates; alky ethoxylates; EO-PO block copolymers; and graft copolymers.

An emulsifying agent is a substance which stabilizes a suspension of droplets of one liquid phase in another liquid phase. Without the emulsifying agent the two liquids would separate into two immiscible liquid phases. The most commonly used emulsifier blends contain alkylphenol or aliphatic alcohol with 12 or more ethylene oxide units and the oil-soluble calcium salt of dodecylbenzene sulphonic acid. A range of hydrophile-lipophile balance ("HLB") values from 8 to 18 will normally provide good stable emulsions. Emulsion stability can sometimes be improved by the addition of a small amount of an EO-PO block copolymer surfactant.

A solubilizing agent is a surfactant which will form micelles in water at concentrations above the critical micelle concentration. The micelles are then able to dissolve or solubilized water-insoluble materials inside the hydrophobic part of the micelle. The type of surfactants usually used for solubilization are non-ionics: sorbitan monooleates; sorbitan monooleate ethoxylates; and methyl oleate esters.

Surfactants are sometimes used, either alone or with other additives such as mineral or vegetable oils as adjuvants to spray-tank mixes to improve the biological performance of the pesticide on the target. The types of surfactants used for bioenhancement depend generally on the nature and mode of action of the pesticide. However, they are often non-ionics such as: alky ethoxylates; linear aliphatic alcohol ethoxylates; aliphatic amine ethoxylates.

A carrier or diluent in an agricultural formulation is a material added to the pesticide to give a product of the required strength. Carriers arc usually materials with high absorptive capacities, while diluents are usually materials with low absorptive capacities. Carriers and diluents are used in the formulation of dusts, wettable powders, granules and water-dispersible granules.

Organic solvents are used mainly in the formulation of emulsifiable concentrates, ULV formulations, and to a lesser extent granular formulations. Sometimes mixtures of solvents are used. The first main groups of solvents are aliphatic paraffinic oils such as kerosene or refined paraffins. The second main group and the most common comprises the aromatic solvents such as xylene and higher molecular weight fractions of C9 and C10 aromatic solvents. Chlorinated hydrocarbons are useful as cosolvents to prevent crystallization of pesticides when the formulation is emulsified into water. Alcohols are sometimes used as cosolvents to increase solvent power.

Thickeners or gelling agents are used mainly in the formulation of suspension concentrates, emulsions and suspoemulsions to modify the rheology or flow properties of the liquid and to prevent separation and settling of the dispersed particles or droplets. Thickening, gelling, and anti-settling agents generally fall into two categories, namely water-insoluble particulates and water-soluble polymers. It is possible to produce suspension concentrate formulations using clays and silicas. Examples of these types of materials, include, but are limited to, montmorillonite, e.g. bentonite; magnesium aluminum silicate; and attapulgite. Water-soluble polysaccharides have been used as thickening-gelling agents for many years. The types of polysaccharides most commonly used are natural extracts of seeds and seaweeds or are synthetic derivatives of cellulose. Examples of these types of materials include, but are not limited to, guar gum; locust bean gum; carrageenam; alginates; methyl cellulose; sodium carboxymethyl cellulose (SCMC); hydroxyethyl cellulose (HEC). Other types of anti-settling agents are based on modified starches, polyacrylates, polyvinyl alcohol and polyethylene oxide. Another good anti-settling agent is xanthan gum.

Microorganisms cause spoilage of formulated products. Therefore preservation agents are used to eliminate or reduce their effect. Examples of such agents include, but are limited to: propionic acid and its sodium salt; sorbic acid and its sodium or potassium salts; benzoic acid and its sodium salt; p-hydroxy benzoic acid sodium salt; methyl p-hydroxy benzoate; and 1,2-benzisothiazalin-3-one (BIT).

The presence of surfactants, which lower interfacial tension, often causes water-based formulations to foam during mixing operations in production and in application through a spray tank. In order to reduce the tendency to foam, anti-foam agents are often added either during the production stage or before filling into bottles. Generally, there are two types of anti-foam agents, namely silicones and non-silicones. Silicones are usually aqueous emulsions of dimethyl polysiloxane while the non-silicone anti-foam agents are water-insoluble oils, such as octanol and nonanol, or silica. In both cases, the function of the anti-foam agent is to displace the surfactant from the air-water interface.

For further information see "Chemistry and Technology of Agrochemical Formulations" edited by D. A. Knowles, copyright 1998 by Kluwer Academic Publishers. Also see "Insecticides in Agriculture and Environment—Retrospects and Prospects" by A. S. Perry, I. Yamamoto, I. Ishaaya, and R. Perry, copyright 1998 by Springer-Verlag.

Applications

The actual amount of pesticide to be applied to loci of pests is not critical and can readily be determined by those skilled in the art. In general, concentrations from about 0.01 grams of pesticide per hectare to about 5000 grams of pesticide per hectare are expected to provide good control.

The locus to which a pesticide is applied can be any locus inhabited by an pest, for example, vegetable crops, fruit and nut trees, grape vines, ornamental plants, domesticated animals, the interior or exterior surfaces of buildings, and the soil around buildings.

Generally, with baits, the baits are placed in the ground where, for example, termites can come into contact with the bait. Baits can also be applied to a surface of a building, (horizontal, vertical, or slant, surface) where, for example, ants, termites, cockroaches, and flies, can come into contact with the bait.

Because of the unique ability of the eggs of some pests to resist pesticides repeated applications may be desirable to control newly emerged larvae.

Systemic movement of pesticides in plants may be utilized to control pests on one portion of the plant by applying the pesticides to a different portion of the plant. For example, control of foliar-feeding insects can be controlled by drip irrigation or furrow application, or by treating the seed before planting. Seed treatment can be applied to all types of seeds, including those from which plants genetically transformed to express specialized traits will germinate. Representative examples include seeds or plants expressing proteins and/or double stranded RNA toxic to invertebrate pests, such as *Bacillus thuringiensis*, Bt Cry toxins, Bt Vip toxins, RNAi, or other insecticidal toxins, those expressing herbicide resistance, such as "Roundup Ready" seed, or those with "stacked" foreign genes expressing insecticidal toxins, herbicide resistance, nutrition-enhancement or any other beneficial traits. Furthermore, such seed treatments with the invention disclosed in this document can further enhance the ability of a plant to better withstand stressful growing conditions. This results in a healthier, more vigorous plant, which can lead to higher yields at harvest time.

It should be readily apparent that the invention can be used with plants genetically transformed to express specialized traits, such as *Bacillus thuringiensis*, RNAi, or other insecticidal toxins, or those expressing herbicide resistance, or those with "stacked" foreign genes expressing insecticidal toxins, herbicide resistance, nutrition-enhancement or any other beneficial traits.

The invention disclosed in this document is suitable for controlling endoparasites and ectoparasites in the veterinary medicine sector or in the field of animal keeping (which for the avoidance of doubt includes pets, for example, cats, dogs, and birds). Compounds according to the invention are applied here in a known manner, such as by oral administration in the form of, for example, tablets, capsules, drinks, granules, by dermal application in the form of, for example, dipping, spraying, pouring on, spotting on, and dusting, and by parenteral administration in the form of, for example, an injection.

The invention disclosed in this document can also be employed advantageously in livestock keeping, for example, cattle, sheep, pigs, chickens, and geese. Suitable formulations are administered orally to the animals with the drinking water or feed. The dosages and formulations that are suitable depend on the species.

Before a pesticide can be used or sold commercially, such pesticide undergoes lengthy evaluation processes by various governmental authorities (local, regional, state, national, international). Voluminous data requirements are specified by regulatory authorities and must be addressed through data generation and submission by the product registrant or by another on the product registrant's behalf. These governmental authorities then review such data and if a determination of safety is concluded, provide the potential user or seller with product registration approval. Thereafter, in that locality where the product registration is granted and supported, such user or seller may use or sell such pesticide.

The headings in this document are for convenience only and must not be used to interpret any portion thereof.

We claim:

1. A pesticidal composition comprising a compound having the following formula (I)

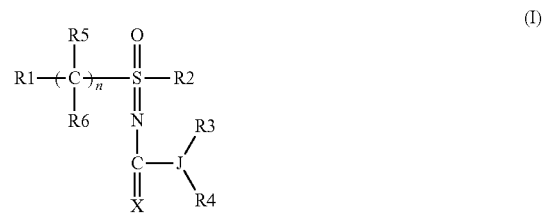

wherein:
(a) R1 is pyridyl, which may be independently substituted with one or more of the following substituents, F, Cl, Br, I, or $C_1$-$C_6$ haloalkyl;
(b) R2 is $C_1$-$C_8$ alkyl;
(c) R3 is F, Cl, Br, I, $C_1$-$C_8$ alkyl, or H;
(d) R4 is $C_1$-$C_8$ alkyl, aryl, $C_3$-$C_8$ cycloalkyl, H, heterocyclyl, C(=O)$C_1$-$C_6$ alkyl, or $C_0$-$C_8$ alkyl-C(=O)OR8, wherein each of which may be independently substituted (except for H) with one or more of the following substituents, F, Cl, Br, I, $C_1$-$C_6$ alkoxy, C(=O)O$C_1$-$C_6$ alkyl, aryl (wherein said aryl may be substituted with one or more substituents selected from F, Cl, Br, I, or $C_1$-$C_8$ alkoxy) and heterocyclyl;

(e) R5 is $C_2$-$C_8$ alkenyl, $C_1$-$C_8$ alkyl, or H, wherein each of which may be independently substituted (except for H) with one or more of the following substituents, F, Cl, Br, I, and $C_3$-$C_8$ cycloalkyl;
(f) R6 is H;
(g) n is 1;
(h) X is NR8;
(i) J is N or CR7;
(j) R7 is H, F, Cl, Br, I, or $C_1$-$C_8$ alkyl;
(k) R8 is H, OH, OC(=O)$C_1$-$C_6$ alkyl, $C_2$-$C_8$ alkenyloxy, $C_1$-$C_8$ alkoxy, $C_1$-$C_8$ alkyl, wherein each of which may be independently substituted (except H) with one or more of the following substituents, F, Cl, Br, I, $C_1$-$C_6$ alkoxy, $C_3$-$C_8$ cycloalkyl, $C_3$-$C_8$ halocycloalkyl, and aryl (wherein said aryl may be substituted with one or more substituents selected from F, Cl, Br, I, or $C_1$-$C_8$ alkoxy).

2. A compound that is a pesticidally acceptable acid addition salt of a compound of formula (I) according to claim 1.

3. A solvate comprising compound of formula (I) according to claim 1.

4. A pesticidal composition according to claim 1 further comprising at least one other pesticide.

5. A pesticidal composition according to claim 1 further comprising at least one herbicide, at least one fungicide, or at least one herbicide and at least one fungicide.

6. A pesticidal composition according to claim 1 further comprising a compound having one of the following modes of action: acetyl choline esterase inhibitor; sodium channel modulator; chitin biosynthesis inhibitor; GABA-gated chloride channel antagonist; GABA and glutamate-gated chloride channel agonist; acetyl choline receptor agonist; MET I inhibitor; Mg-stimulated ATPase inhibitor; Midgut membrane disrupter; or oxidative phosphorylation disrupter.

7. A pesticidal composition according to claim 1 wherein R1 is substituted with one or more of the following substituents Cl, or $CF_3$.

* * * * *